(12) United States Patent
Tracey, Jr. et al.

(10) Patent No.: US 7,018,617 B1
(45) Date of Patent: Mar. 28, 2006

(54) METHODS AND COMPOSITIONS ASSOCIATED WITH NOCICEPTIVE PAIN

(75) Inventors: William Daniel Tracey, Jr., Pasadena, CA (US); Seymour Benzer, San Marino, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/907,155

(22) Filed: Jul. 16, 2001

Related U.S. Application Data

(60) Provisional application No. 60/286,726, filed on Apr. 25, 2001, provisional application No. 60/218,319, filed on Jul. 14, 2000.

(51) Int. Cl.
*A61K 49/00* (2006.01)
*A01K 67/00* (2006.01)
*A01K 67/033* (2006.01)

(52) U.S. Cl. .............................. 424/9.2; 800/8; 800/9; 800/13

(58) Field of Classification Search ................ 800/3, 800/8, 13, 14; 435/325, 6; 536/23.1
See application file for complete search history.

(56) References Cited

U.S. PATENT DOCUMENTS 6,291,739 B1 * 9/2001 Sharma et al. ................. 800/3

OTHER PUBLICATIONS

Overbeek, 1994, "Factors affecting transgenic animal production," Transgenic animal technology, pp. 96-98).*
Wall, 1996, Theriogenology, vol. 45, pp. 57-68.*
Kappell, 1992, Current Opionions in Biotechnology, vol. 3, pp. 548-553.*
Houdebine, 1994, J. Biotech. vol. 34, pp. 269-287.*
Cameron, 1997, Molec. Biotech. vol. 7, pp. 253-265.*
Sigmund, 2000, Artheroscler. Thromb. Vasc. Biol., vol. 20, pp. 1425-1429.*
Atta, 1998, Jour. Enteropharmacol., vol. 60, pp. 117-124.*
Mullins, 1993, Hypertension, vol. 22, pp. 630-633.*
Hammer, 1990, Cell, vol. 63, pp. 1099-1112.*
Mullins, 1989, EMBO J. vol. 8, pp. 4065-4072.*
Taurog, 1988, Jour. Immunol. vol. 141, pp. 4020-4023.*
Campbell, 1994, PNAS, vol. 91, pp. 2135-2139.*
Jaquemar, et al. "An Ankyrin-like Protein with Transmembrane Domains Is Specifically Lost After Oncogenic Transformation of Human Fibroblasts" *J. of Biological Chemistry*, 274(11):7325-7333 (1999).
Story, et al., "ANKTM1, A TRP-Like Channel Expressed in Nociceptive Neurons, Is Activated by Cold Temperature", *Cell*, 112:819-829 (Mar. 2003).

* cited by examiner

*Primary Examiner*—Scott D. Priebe
*Assistant Examiner*—Valarie Bertoglio
(74) *Attorney, Agent, or Firm*—DLA Piper Rudnick Gray Cary US LLP

(57) ABSTRACT

Provided are methods and compositions corresponding to a genetic locus associated with nociceptive pain. In addition, method of identifying or modulating nociceptive pain and associated disorders is also provided.

5 Claims, 26 Drawing Sheets

Fig. 1A
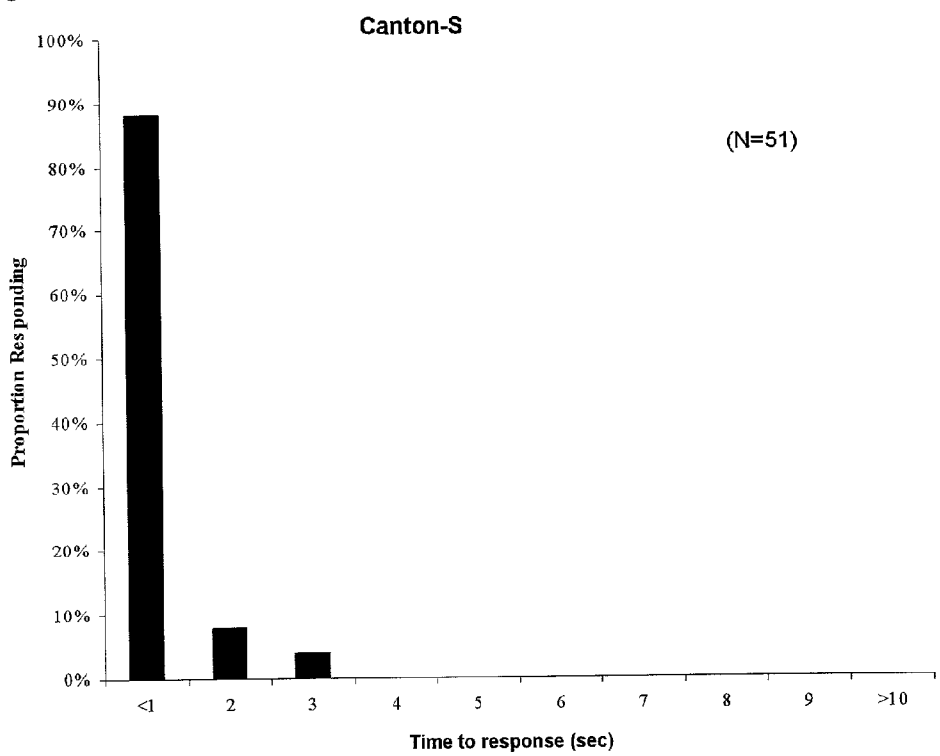
Fig. 1B
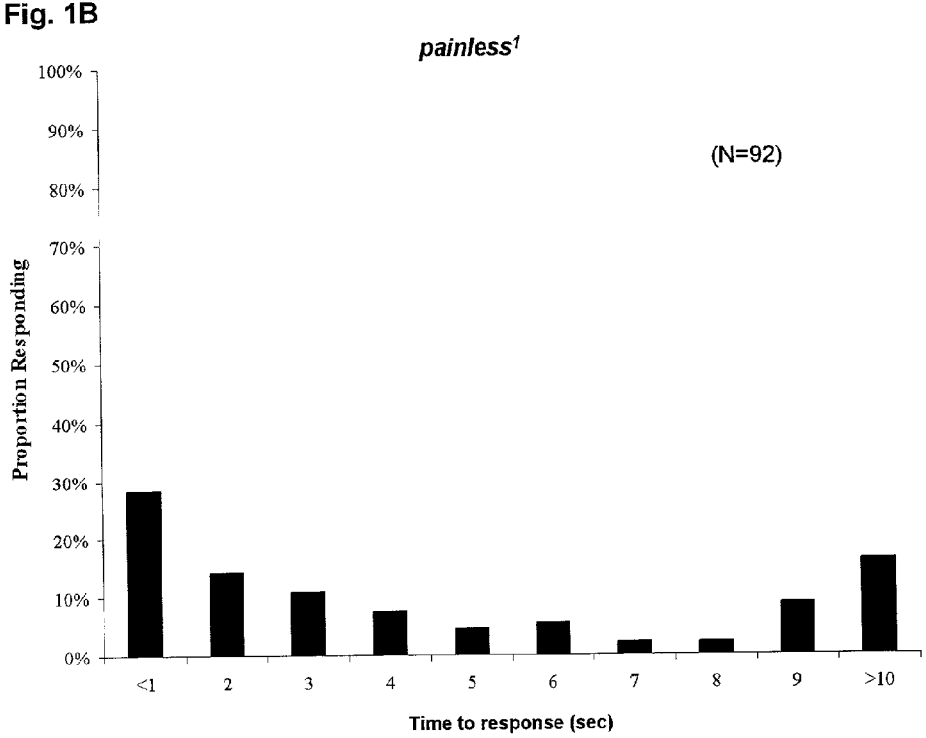
Figure 1

Fig. 1C
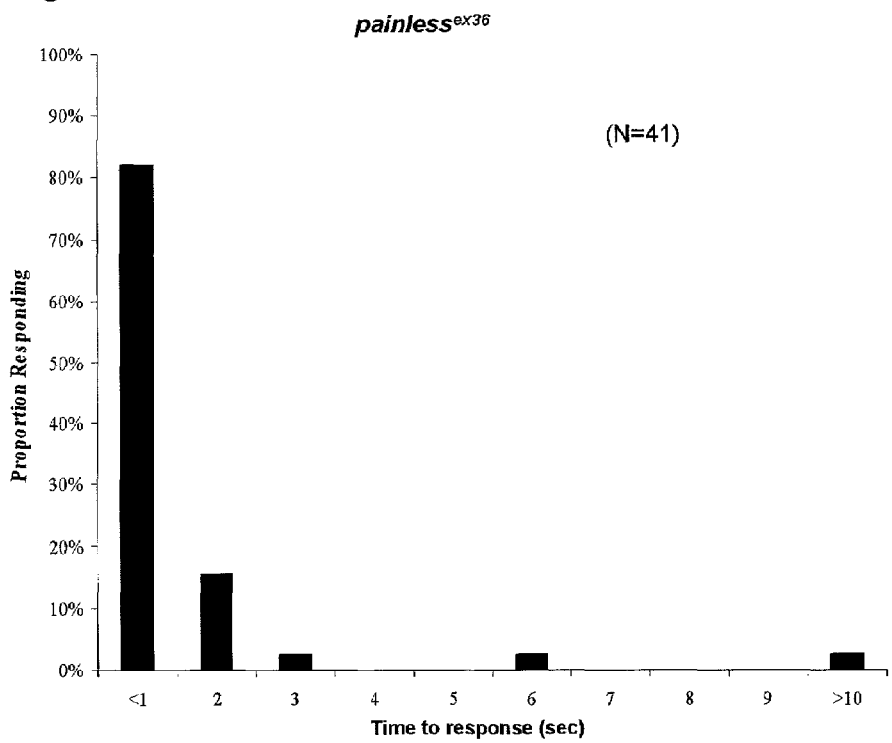
Fig. 1D
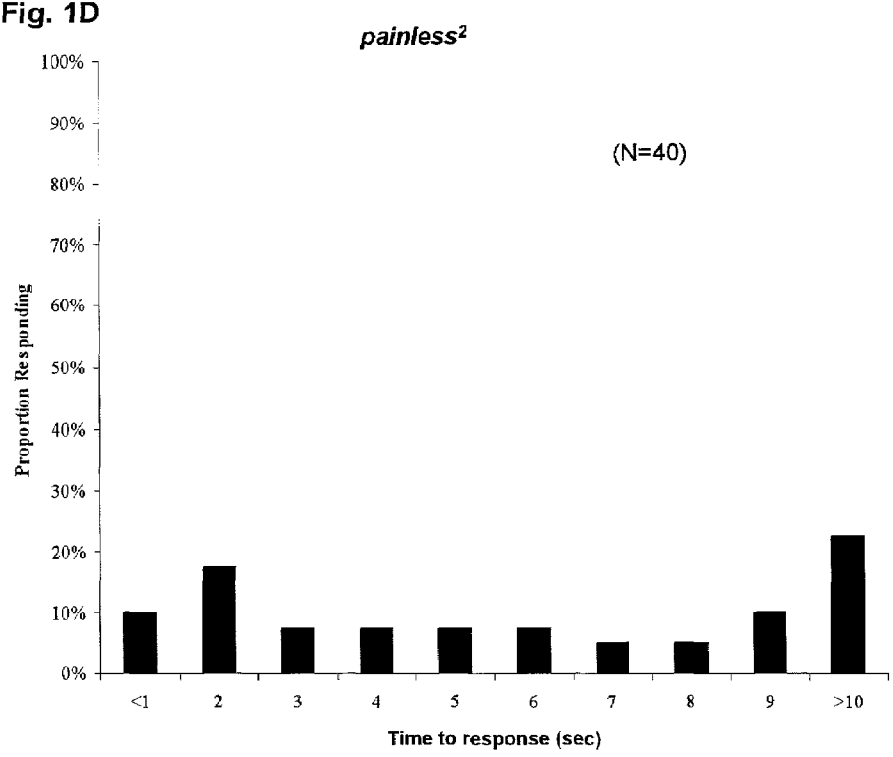
Figure 1

Fig. 4C
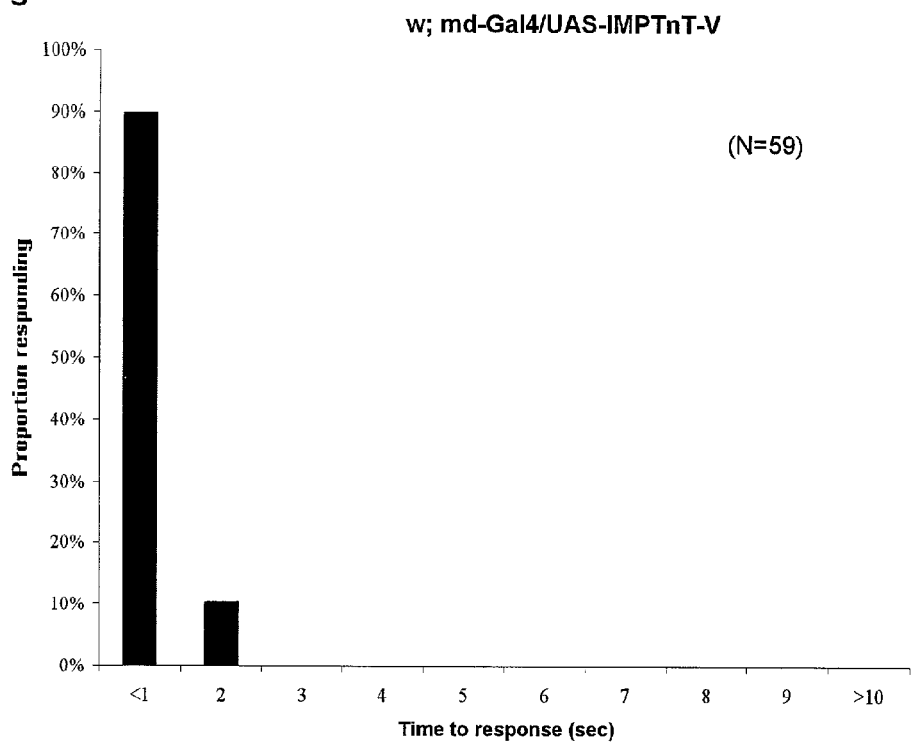
Fig. 4D
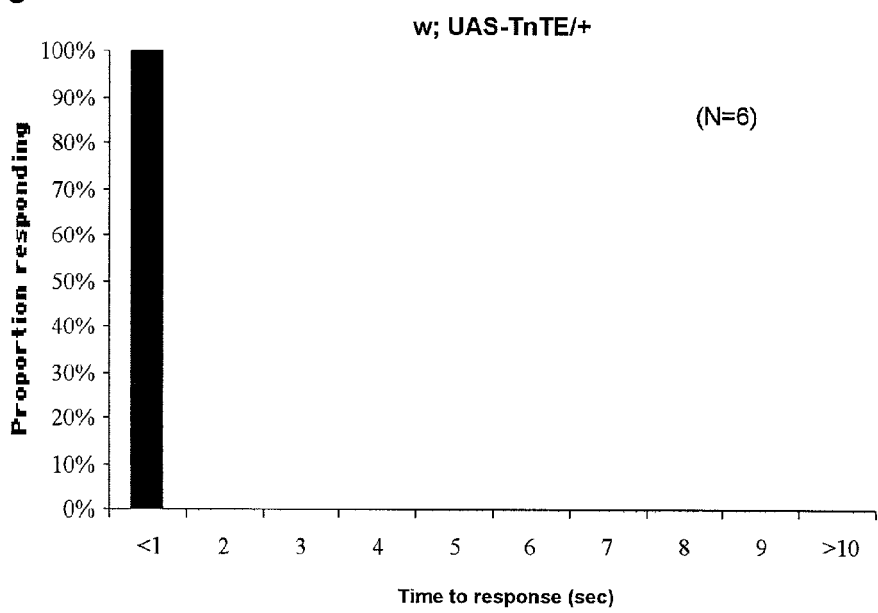
Figure 4

Fig. 4E
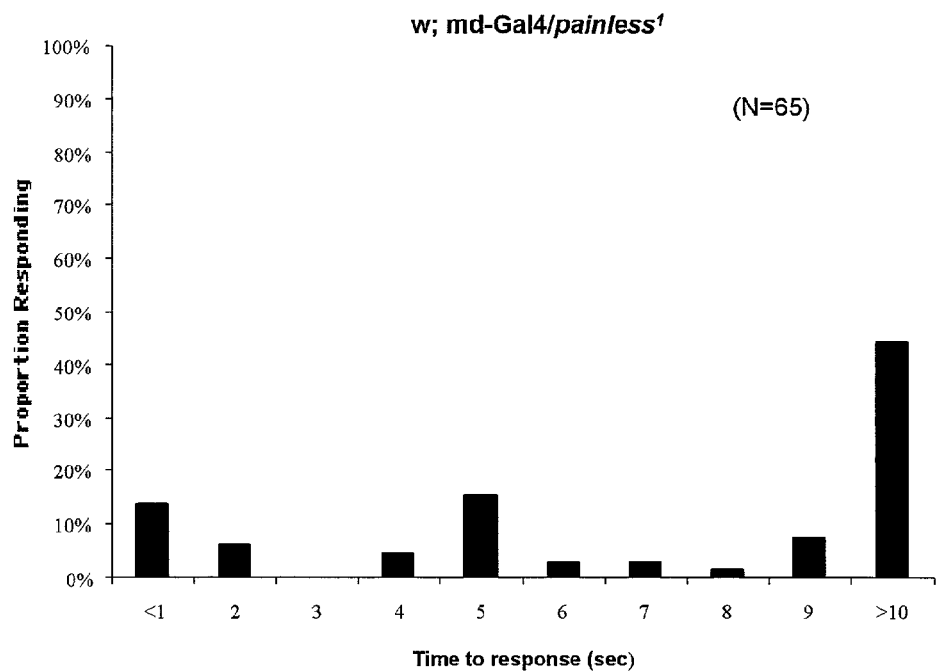
Fig. 4F
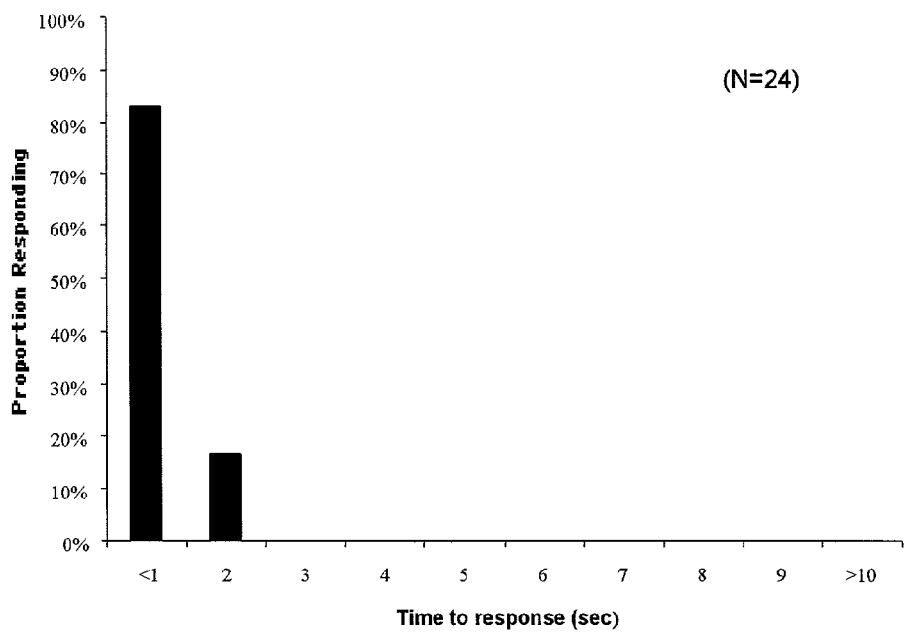
Figure 4

Fig. 4G
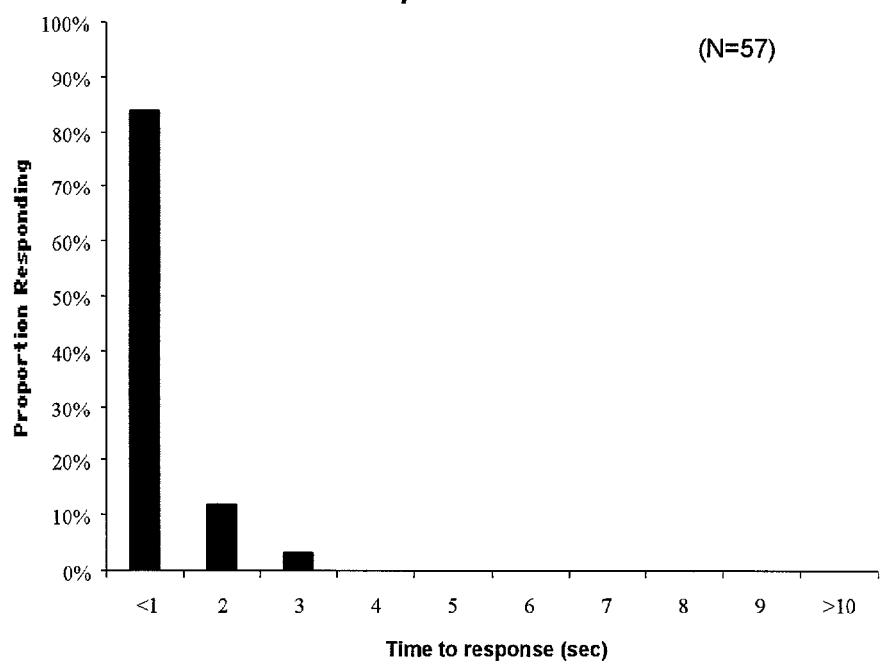
Fig. 4H
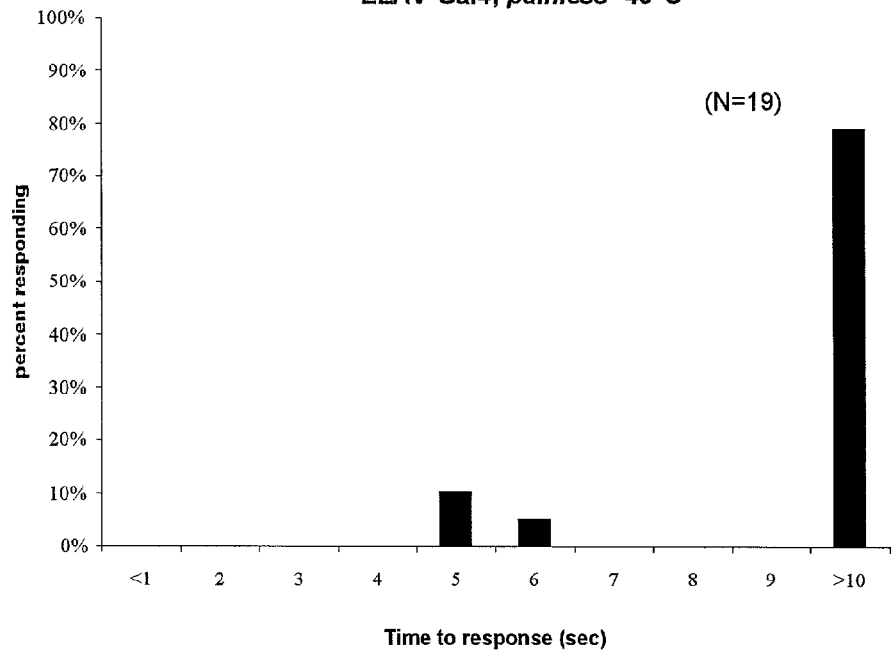
Figure 4

Fig. 4I
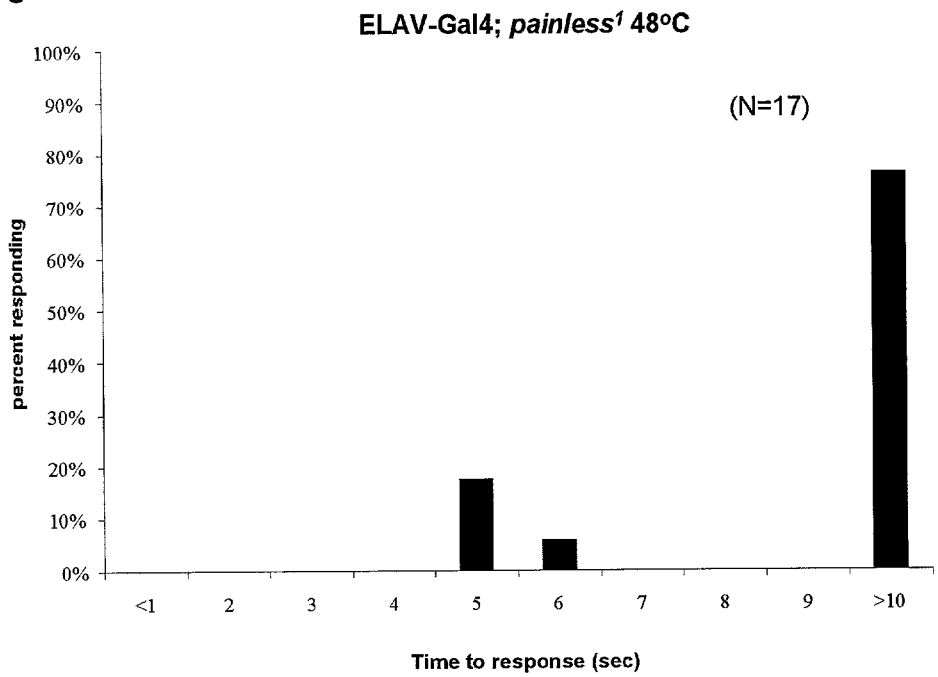
Fig. 4J
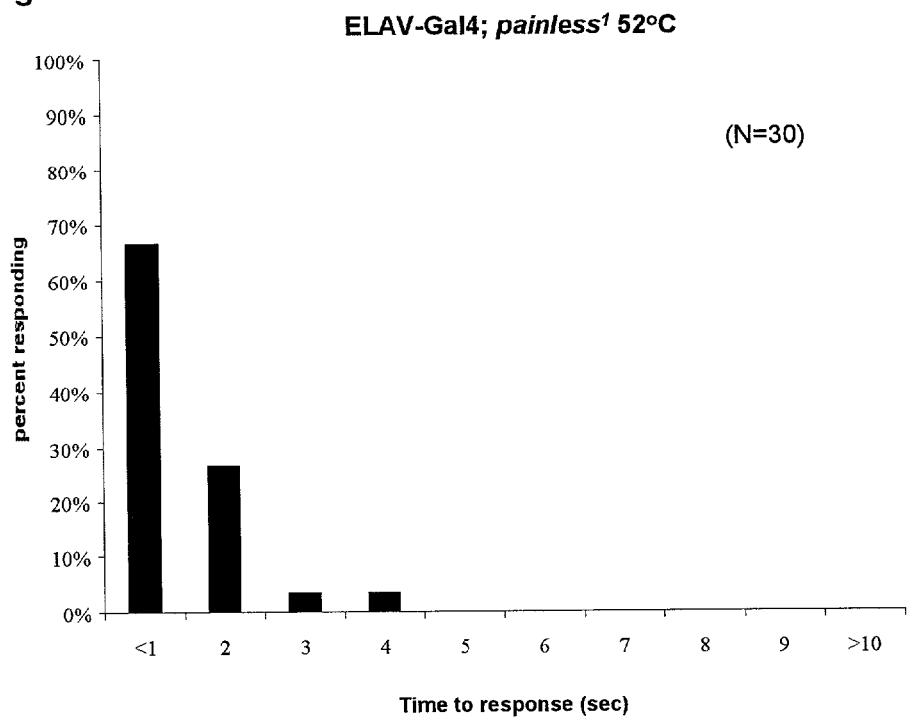
Figure 4

FIGURE 5

```
MDFNNCGFID PQAQLAGALA KQDIRQFVAA LDSGALADLQ DDRHTSIYEK ALSTPGCRDF  61
IEACIDHGSQ VNYINKKLDK AAISYAADSR DPGNLAALLK YRPGNKVQVD RKYGQLTPLN 121
SLAKNLTDEN APDVYSCMQL LLDYGASPNI VDQGEFTPLH HVLRKSKVKA GKKELIQLFL 181
DHPELDIDSY RNGEVRRLLQ AQFPELKLPE ERHTGPEIDI QTLQRTLRDG DETLFEQQFA 241
EYLQNLKGGA DNQLNAHQEE YFGLLQESIK RGRQRAFDVI LSTGMDINSR PGRANEANLV 301
ETAVIYGNWQ ALERLLKEPN LRLTPDSKLL NAVIGRLDEP PYDGSSHQRC FELLINSDRV 361
DINEADSGRL VPLFFAVKYR NTSAMQKLLK NGAYIGSKSA FGTLPIKDMP PEVLEEHFDS 421
CITTNGERPG DQNFEIIIDY KNLMRQERDS GLNQLQDEMA PIAFIAESKE MRHLLQHPLI 481
SSFLFLKWHR LSVIFYLNFL IYSLFTASII TYTLLKFHES DQRALTAFFG LLSWLGISYL 541
ILRECIQWIM SPVRYFWSIT NIMEVALITL SIFTCMESSF DKETQRVLAV FTILLVSMEF 601
CLLVGSLPVL SISTHMLMLR EVSNSFLKSF TLYSIFVLTF SLCFYILFGK SVEEDQSKSA 661
TPCPPLGKKE GKDEEQGFNT FTKPIEAVIK TIVMLTGEFD AGSIQFTSIY TYLIFLLFVI 721
FMTIVLFNLL NGLAVSDTQV IKAQAELNGA ICRTNVLSRY EQVLTGHGRA GFLLGNHLFR 781
SICQRLMNIY PNYLSLRQIS VLPNDGNKVL IPMSDPFEMR TLKKASFQQL PLSAAVPQKK 841
LLDPPLRLLP CCCSLLTGKC SQMSGRVVKR ALEVIDQKNA AEQRRKQEQI NDSRLKLIEY 901
KLEQLIQLVQ DRK
```

FIGURE 6

```
atggacttta acaactgcgg cttcattgat ccgcaggccc agctagctgg agctttggcc 61
aagcaggaca tccgacagtt cgttgctgcc ctggacagcg gtgccctggc cgatctacaa 121
gacgaccgcc ataccagtat ctacgagaag gcactctcaa caccaggttg tcgtgacttc 181
attgaagcct gcatcgacca cggcagccag gtgaactaca tcaacaagaa gctggacaag 241
gccgcaatca gctatgcggc tgactctagg gatccaggaa acctggcggc tctccttaag 301
taccgccccg gaaacaaagt ccaggttgat agaaaatatg ggcagcttac tccacttaac 361
tcacttgcca agaatctcac ggatgaaaat gccccagacg tgtactcctg catgcaactc 421
ttgctggact acggcgcctc gccgaatatc gtagaccagg gcgagttcac acccttgcac 481
catgtgctga gaaagagcaa ggtgaaggct gggaagaagg aactgattca gctctttctg 541
gaccatccgg agctggatat cgatagttac cgaaacgggg aggtgcgcag actgctgcag 601
gcgcaatttc cggagcttaa gctgccggaa gagcgtcata ccgggccgga gattgacatc 661
caaactcttc aaaggactct acgggacggg acgaaacac tgtttgagca gcagttcgct 721
gagtacttgc agaatctcaa aggcggagcg gataaccaac taaatgccca ccaggaggaa 781
tacttcggac tgctgcagga gagcatcaag aggggcaggc agcgagcctt cgatgtcatt 841
ttgtccactg gcatggatat caactcgaga ccaggcaggg ccaacgaggc caatctcgta 901
gagacggccg tgatatacgg taactggcag gcgttggagc gactgcttaa ggagccaaac 961
ctgcgactta ctccagactc caagctacta aatgcagtaa tcggccgtct ggatgagcca 1021
ccgtatgatg gctccagcca ccagcgctgc tttgaattgc tcattaacag cgatcgcgta 1081
gacatcaacg aagctgattc cggacgcctg gtgcctctgt tcttcgctgt aagtaccgc 1141
aacacgagtg cgatgcaaaa actcctgaag aacggtgcct acattggttc taagagcgca 1201
tttggcacac tacccatcaa ggacatgcca cccgaggttc tcgaagagca cttcgactcg 1261
tgtatcacca caaacggaga gaggcctggt gaccagaact ttgagatcat catcgattat 1321
aagaacctaa tgcgccagga gagagactcc ggactcaacc agctgcaaga cgaaatggcc 1381
ccgatcgcat tcatcgccga gtcgaaggag atgcgccacc tgctccagca cccgctgatc 1441
tcgagctttc tattcctcaa gtggaccga ctttccgtga tattctacct gaacttcctg 1501
atatactcgc tttttaccgc ctccataatt acctacgc tcctcaagtt ccacgaaagc 1561
gatcaaaggg ctcttactgc attttcgga ttgctttcct ggctgggaat cagctacctt 1621
atattacggg agtgcatcca gtggataatg tctccagttc ggtactttg gtctataacg 1681
aatattatgg aggtggctct tattacacta tctatcttta cctgcatgga atccagcttc 1741
gacaaggaga cgcagcgcgt cttagccgta tttaccatcc tactcgtctc catggagttt 1801
tgtttactag tgggctccct gccagtgctc tcaatttcga cgcacatgct gatgctgcga 1861
gaggtgtcaa acagcttctt aaagagcttt accctctact cgatcttcgt gctcaccttc 1921
agcctgtgtt tctatatcct cttcggcaag tcagtggagg aagaccagtc taaaagcgct 1981
acgccatgtc cacctctggg gaagaaggag gggaaggacg aggaacaggg cttcaacaca 2041
tttaccaagc ctatcgaggc cgtgatcaag accattgtga tgctgacagg cgagtttgac 2101
gccggaagca tccagtttac cagcatctac acctacctga ttttcctgct cttcgtgatc 2161
tttatgacga tagtgctgtt caacctttg aacggtcttg cagtgagcga cacccaagtt 2221
attaaggctc aggcggaact gaacggagcc atttgcagaa ccaacgtcct tagtcggtac 2281
gagcaggttc tcactggcca cggacgcgct gggttttgt tgggcaacca tctcttccgc 2341
agcatctgcc aacgtttgat gaacatctac ccgaactact taagtctgcg tcagatttcc 2401
gtgctgccga acgatggaaa caaagtgctt attccaatga gcgatccctt cgaaatgagg 2461
acccttaaga aggctagctt tcagcaattg ccctgagtg ctgcagtgcc ccagaagaag 2521
ctgttggatc caccgcttag acttctgccc tgctgctgtt ccctgctcac cggaaagtgc 2581
tcccagatga gcggccgggt ggtcaaacgg ccctcgagg taatcgatca gaagaacgcg 2641
cggagcaga ggcggaaaca ggaacagatc aacgacagtc gactgaagct gatcgagtac 2701
aagctggagc aattaataca gctggtccag gaccggaagt ga
```

FIGURE 7

```
TGCGGTCGCTTTCACGGATCAGATTAGTCGTTGTCTGGATATTAACGAGGAAGACCAAACCAATGGACTT
TAACAACTGCGGCTTCATTGATCCGCAGGCCCAGCTAGCTGGAGCTTTGGCCAAGCAGGACATCCGACAG
TTCGTTGCTGCCCTGGACAGCGGTGCCCTGGCCGATCTACAAGACGACCGCCATACCAGTATCTACGAGA
AGGCACTCTCAACACCAGGTTGTCGTGACTTCATTGAAGCCTGCATCGACCACGGCAGCCAGGTGAACTA
CATCAACAAGAAGCTGGACAAGGCCGCAATCAGCTATGCGGCTGACTCTAGGGATCCAGGAAACCTGGCG
GCTCTCCTTAAGTACCGCCCCGGAAACAAAGTCCAGGTTGATAGAAAATATGGGCAGCTTACTCCACTTA
ACTCACTTGCCAAGAATCTCACGGATGAAAATGCCCCAGACGTGTACTCCTGCATGCAACTCTTGCTGGA
CTACGGCGCCTCGCCGAATATCGTAGACCAGGGCGAGTTCACACCCTTGCACCATGTGCTGAGAAAGAGC
AAGGTGAAGGCTGGGAAGAAGGAACTGATTCAGCTCTTTCTGGACCATCCGGAGCTGGATATCGATAGTT
ACCGAAACGGGGAGGTGCGCAGACTGCTGCAGGCGCAATTTCCGGAGCTTAAGCTGCCGGAAGAGCGTCA
TACCGGGCCGGAGATTGACATCCAAACTCTTCAAAGGACTCTACGGGACGGGGACGAAACACTGTTTGAG
CAGCAGTTCGCTGAGTACTTGCAGAATCTCAAAGGCGGAGCGGATAACCAACTAAATGCCCACCAGGAGG
AATACTTCGGACTGCTGCAGGAGAGCATCAAGAGGGGCAGGCAGCGAGCCTTCGATGTCATTTTGTCCAC
TGGCATGGATATCAACTCGAGACCAGGCAGGGCCAACGAGGCCAATCTCGTAGAGACGGCCGTGATATAC
GGTAACTGGCAGGCGTTGGAGCGACTGCTTAAGGAGCCAAACCTGCGACTTACTCCAGACTCCAAGCTAC
TAAATGCAGTAATCGGCCGTCTGGATGAGCCACCGTATGATGGCTCCAGCCACCAGCGCTGCTTTGAATT
GCTCATTAACAGCGATCGCGTAGACATCAACGAAGCTGATTCCGGACGCCTGGTGCCTCTGTTCTTCGCT
GTTAAGTACCGCAACACGAGTGCGATGCAAAAACTCCTGAAGAACGGTGCCTACATTGGTTCTAAGAGCG
CATTTGGCACACTACCCATCAAGGACATGCCACCCGAGGTTCTCGAAGAGCACTTCGACTCGTGTATCAC
CACAAACGGAGAGAGGCCTGGTGACCAGAACTTTGAGATCATCATCGATTATAAGAACCTAATGCGCCAG
GAGAGAGACTCCGGACTCAACCAGCTGCAAGACGAAATGGCCCCGATCGCATTCATCGCCGAGTCGAAGG
AGATGCGCCACCTGCTCCAGCACCCGCTGATCTCGAGCTTTCTATTCCTCAAGTGGCACCGACTTTCCGT
GATATTCTACCTGAACTTCCTGATATACTCGCTTTTTACCGCCTCCATAATTACCTACACGCTCCTCAAG
TTCCACGAAAGCGATCAAAGGGCTCTTACTGCATTTTTCGGATTGCTTTCCTGGCTGGGAATCAGCTACC
TTATATTACGGGAGTGCATCCAGTGGATAATGTCTCCAGTTCGGTACTTTTGGTCTATAACGAATATTAT
GGAGGTGGCTCTTATTACACTATCTATCTTTACCTGCATGGAATCCAGCTTCGACAAGGAGACGCAGCGC
GTCTTAGCCGTATTTACCATCCTACTCGTCTCCATGGAGTTTTGTTTACTAGTGGGCTCCCTGCCAGTGC
TCTCAATTTCGACGCACATGCTGATGCTGCGAGAGGTGTCAAACAGCTTCTTAAAGAGCTTTACCCTCTA
CTCGATCTTCGTGCTCACCTTCAGCCTGTGTTTCTATATCCTCTTCGGCAAGTCAGTGGAGGAAGACCAG
TCTAAAAGCGCTACGCCATGTCCACCTCTGGGGAAGAAGGAGGGGAAGGACGAGGAACAGGGCTTCAACA
CATTTACCAAGCCTATCGAGGCCGTGATCAAGACCATTGTGATGCTGACAGGCGAGTTTGACGCCGGAAG
CATCCAGTTTACCAGCATCTACACCTACCTGATTTCCTGCTCTTCGTGATCTTTATGACGATAGTGCTG
TTCAACCTTTTGAACGGTCTTGCAGTGAGCGACACCCAAGTTATTAAGGCTCAGGCGGAACTGAACGGAG
CCATTTGCAGAACCAACGTCCTTAGTCGGTACGAGCAGGTTCTCACTGGCCACGGACGCGCTGGGTTTTT
GTTGGGCAACCATCTCTTCCGCAGCATCTGCCAACGTTTGATGAACATCTACCCGAACTACTTAAGTCTG
CGTCAGATTTCCGTGCTGCCGAACGATGGAAACAAAGTGCTTATTCCAATGAGCGATCCCTTCGAAATGA
GGACCCTTAAGAAGGCTAGCTTTCAGCAATTGCCCCTGAGTGCTGCAGTGCCCAGAAGAAGCTGTTGGA
TCCACCGCTTAGACTTCTGCCCTGCTGCTGTTCCCTGCTCACCGGAAAGTGCTCCCAGATGAGCGGCCGG
GTGGTCAAACGGGCCCTCGAGGTAATCGATCAGAAGAACGCGGCGGAGCAGAGGCGGAAACAGGAACAGA
TCAACGACAGTCGACTGAAGCTGATCGAGTACAAGCTGGAGCAATTAATACAGCTGGTCCAGGACCGGAA
GTGAGGAGAATGTATTTTGGTAGCTTTAGTATTTATGAGACTAATCAGCCTTTTAGAACGATTTGCATTT
AACATTCAGTTTAAAGAGCCGAGTTAGTCGGAAATTGTTTTTATTAACATACGAGTAATGAAATTGAACA
AAACCCTTAATAATTGTCAGTAAGTAAGTAGTATATAATGGTTATATAGACAGTAAATATTGTATAAACG
AATATCATTACTGTACTATTTGTACCCGAGTAAATATTTAATTTCAAATGTTAAAAAAAAAAAAAAAAA
```

FIGURE 8A

```
TCGAGGTGCTGCAGTTCTTCACGATGCGCGCCTGGTTCTTTAAGTCGGATGCCTATTC
CTCGCTGTGGGCCATGCTAAACGAGTCGGACAGGAAAAAGTACGTAGCGCGAGCGTAG
AAGGGTACTGAGTTCACTTAATCCGAAACACCTGATCCCACCCAAAAGCTTCAATATG
GACATGGATCCCGAGGAGACTGTCCCCATGTACATTGAGTCGTGTGTCCAGGGAGGGC
GACAGTACCTGATGAAGGAGTCGCCCGATAGTTTGCCCCGCGCCCGGCTCCAGCTGAA
GCTGTAAGCGAGACTCGCCCACAGGGACATAAGCCCTGAGCCCGATCTCTAAGCACGG
TCTTCCTTTCATTTATAGAATGTACATCCTGGACCGCGCTTGCAAGACGCTCATCGTG
GGCACCCTGTGCTACTGGACCTACGGTTTGGTGGCACGCCTGCTCGGCGTCTAATACG
ACGGCCACCCGGGACATTTTCAATCCATTCGCGCGCTTTTCTCAATCAATCTCTGCTT
AGGTTCGCTTGGGGGCATAACTTCGAGCCACTCGACGAGTGGCCTCGAATCTGGTTTT
CATTTCTACTTTAAGTGATTATCTATGTTTCGTGTCAAAATAAAAAATCTGTGTACTG
AGTTTATGTGTCTGTGCTTCAAGTGTACAAGTGTTGATCCAGAGGACTCGCGCGACAA
CACGAACAACACAAACAAAACCCACAAAACCCACTGAACACACAGATCACACAGGACA
AAGAGCACAATGATATTTTCCCCGATTGCGCACTATTTCCCACCTTCTAAATTCCCAC
ACTTATCCTTGGCGGAAACATAGTCCAAAACATACAACTACACTACTCACACCCACAC
CATACACACATTCACACATTCACACATAATACGGCTTCGGTGACCATCATCTTGGGCT
CGTGGTATGTAGACTGGTTTCATGCGCTGAGCAGATTAGACGCCCCTTAGTAAACATC
TATTCCTTCCGCCCTGTAGTGTCGCCGGCTGCCTACGAGCCGTTGCCCGGATGGGTGG
ACAACCTGAATGGACCGACTGGCCTGATGATCGGATGCGGCAAGGGCGTGATCCGGTC
CGTTCTGGTGAATCAGCAGAACAAGGCCGAGGTGATTCCCGTCGACTACGCTATCAAC
GGGCTGATCGTCATTCCCTACGAGTTCAACAAGCAGGCCAAGCGGCCTACCAATGTGC
CCGTTTATAATATAACCAATGCGGACCACAGGAAGATGACCATGGGCACCGTTGTGGA
GATGAGCAAACGCATCAACAAGCAGTTCCCATTTAACGCGGGTCTATGGTACCCGGAC
CCTTGCGTTACCACCAACCAATTATACCACAACTTCAACGTGGCTCTGTTTCATTGGT
TGCCCGCTTACTTCCTGGACTTCCTGATGCTGATATTAGGTCAGAAGCGATTGTAAGT
TGCCCCGCACTGAATTACCCCAAATGGAGCTTATGTGCCATTTCCCTCCCTAGCATGT
TGAGAGTTCAGGAGAAGATATCCACAGGTCTGGGCGTCCTCCAGTTCTTTACCCTCAA
TGCCTGGTGCTTCCGATCTGATAACTACGCCTCCCTCTGGAACAAACTCAACGAGGAA
GACAAGGCGATGTAAGTGCTGCTATTGAATATTAACATATTAACATATCAATATCAAT
TTCCCATTCAGTTTTAACATGAACATGAACACGGAGAACACCGAGGAGGAGTACATGA
TTGAGTGTGCTAAGGGCGCTCGAAAGTTTATCCTCAAGGAAAAGGAGGAGGATCTGCC
CACTGCGCGCGTGCACATGAAGATGTAAGTTAGGCAAGAGCCTGTGCTACCCACTATG
ACTCACTCATCTTCACTTCCAGCCAACGAGTCGTAGACGTTGTGTGCAAGACGGTGAT
TGTGGGACTGTTCTTCTACTACCTCCTTAAGTGGACGGGGGTGCTGGCTATATTCTGA
TTCTAGTTCTCCGTGGACTTGCATTGGTTTGGTGGTCACAGGCATTTATTTAGTCAAT
TAGCTTAGTTGTAGTTACGCATATTCGAGGTTTTGAATCCAAATAAATATGATTGTAG
GTTGTTGAATATACACATTTCGCCAACTGCGCCGTGTTTCTCTTTCCCAATCCAGTCA
CTAAAGCAGACTTTGTGTCTAACCATACTGACCTGTACTTTGTTCTCCAGTAACTCCA
GCTGTCGCTGAGCCTCTGCCAGGTTGGGTGGACAATATGAACGGACCTACGGGAGTTC
TCATTGGCGCCGGCAAAGGAGTTATCCGATCCATGATCTGCAACGGGGAGCTAAAATC
TGAAGTGATACCTGTGGACATCGCCATTAACGGTCTTATCTTATTACCATATCATAAC
AGTCTTGCGGAGAAGAGGTAAATTTTCAGACGCCTCCCATGTCAATGTGATGTATAA
CTTCTGCCACAGACCTCTTCAGATCCCAGTCTACAACTTGACCGTGGACGATGCCAAA
AAGCGCACATGGAAATGGATAATGGATGTGGGTCGCGACTTGGGCATTAAGTACCCCT
TCGAAGTGGGACTCTGGTATCCCGACGGCAACATGACGTCCAGCAAATTCTATCACAC
CATCTGTACCATT
```

FIGURE 8B

```
CTGTTTATGTGGCTGCCAGCCTACCTTATCGACTTCCTACTCCTGATCTTTGGACAAC
GTCGCTTGTAAAACCTTCAAAAGAATTTGTCAGTTCCGAATAAGAATCTAACCCAAAA
CTTTTCTGTTTGTCTAGCATGATTCGGGTTCAAACCAAAATCGCTGTGGGTTTGGAAG
TTTTGCAGTTCTTTACCACGCGAAGCTGGGACTTTAAATCCACACACTTCGAGCAGAT
CTACAAGGAATTAGGATCCACAGATCGGAGGATGTAAGCAATATATATCATATGCATT
CAATAGATGAATTCATGCATTAAATGGATTTATAACGTAACTTTATTTACGACAGATT
TAAGATTAACACCGACGATGTCGACGATTATGAGTACATGAAAGTCAGTATTTTGGGT
GGCCGTCAGTATGTGATGAAGGAACCTTTAACTTCGTTGCCGAAATCACGCATACAAT
TGAGATTGTAAGTAATTTGTTATTTCCATCTATAGTGTTTAACCAATGCTCTTGTTTT
CCAGCATGTATGTCCTGGACCGTATTTGCAAACGATGATAATTTCAGGCCTTCTATA
TTGGGTTTCCCAAAAACTGAGAGTAGTTGACCTATTTAGAAGCGTATTCCATTCTAGT
ACATAACATTCTTCTTCAGTTGCTTTTTTAACATTTTGTACCTTTTATTTCATGTGCC
TTTGAAAGGGTTTGTAAGAAAATCTTGTTAAAAATATTCAGGTGTTTTGTATACGTAA
ACTTGTTATTGCAAGTCGTTGATAATAAAAATTTTTAAACATTAGGCTATTTGATTTC
AATTTACTGTTACTGTGAGTTACTGTTGTATAGGTTATTTTTATTAGCACTATCTTGA
AGTTATACAAATTTGTAAAAATACAGATGAGACGAGGAATCCAACTCGAGTCCCAAAC
TCTACAGATCTGAATCGGTTTTGTACCAAATTAAGGATGATGTTCCATTGCCGACAGA
TGTAGTGGAATGAATAGAATATTTAGTATCTTAAATCACTTGTAGCCGTTTGTTATTA
GTTGGCTATTCGGCACACATTTAACTGCGAAAAATTTACCATTATTTTTAATGCGCC
CGGAGAGTCTCCACAAGTGTGCCCATATATCTGCCATTCAAATTCTAAGCTCACGAGA
CAAAAGAGTTATCGATCGATATGCAGGCTCTGTGTGGCCCCTGTTAGCTTTCTGTTAA
ATTTAAATTTCTGTAAAGTGCCCGCCACTGCGGTCGCTTTCACGGATCAGATTAGTCG
TTGTCTGGATATTAACGAGGAAGGTAGTGATCGCGCATTAGTGTCATGCGTTATTTGC
TTCGGCGCTGAGAAGTGTTTTGAAAACAGTTTTTGAAAGCCCGAGGAAGATCTCAATG
GGTCAATGAGTCATCTCATTCACTATGCAAATAAGACCGGGGTTGCGCCAAACCTTTA
CTTAAAGACGATGACTCGCGGGGAAGTTAAGACGTTTTATTAGTTACTGCAATGAAT
CATGTGTAATGCAGATCTGAAACCGCAGTTGCAAAGTGATCTCGACATCAACCCACAC
AACAAAAACATAAGCAGTGAAAACAAGTTTTAAAACATTTAACGAAGCAAGGTTAAGA
AACTGCAGAAAACGGCGCCCACGGCGCAATCGAAAAAAAATTTAAAAAAAAGCTTTGT
TTTAATGACGCCAGAACAGCTAATAAATTGATTGAATTGCATTTGACAAATGATTAAT
TTGAAATCTACATATATGCGACCTGTGACGTCATCGAAGTTTTTAAAAAAACTATTTT
AAAATGCCTGGTGGGCAGATAATGAATATGCCCTAAAAGGCAACTCCCGCCGTGTCCA
CTTTTCTGTGAAGTGCTCGGATTGTGATACCATTCCCAAATACGAATTAAACGTATAG
TTTTATTGCTGACCCGGCGAGTTTAGAAAATGTCGTGTAAGACGAGCCGATAGAGGCC
CATGTTTACCCAACTCGGAACTGGGTTGGCGACAGTTTCCCCCAAGCACAGACATTTG
CATCGAATTTAGGCGTACAGGGCTTCCGTTCCCTCCAGAAGCGCTTAATATGCGTTT
TTTATTGCCAATTACAATTAAGTAATCCATCGATTAGGCGTTATGCGGCATGTTAGGA
CCCTCCTCTGGAGCCCGCGCTCCAGCCTACTTACGACTGCAAAAACCGTGCGGCTGAA
TTCATTCGCTCGCTGATTTGGCTCCGCCCATCTAATTTTGTATTCGTTTTCTACTGT
TCGTGGGACACAGGGGCGTGGGCGCAGAGGGGCTTGAGTTGCTTGGACCGATTGGTAG
GTGGTGATTCCTTCGGTTCAGGAATCCGTCCATCTAGCACACGAATTAGCTTTCGTGT
GTGTTTCTGAGTTGATCTCACACATGTACTACGTACGTCCGAGTGTGTTTAATTAAAT
TATTTGAAATTACTGAATCGTGCGGAGCGGAGACTCTGTCTCCCCACTCCGGACACCC
CTCCCAAATCTTTTGTTGTGCACACGATGTGGGCCAGTCAATTGTTTATGAAGTGCAC
AGTGGGTATA
```

FIGURE 8C

```
TAGAGCACTGATCTCCATGTGGCAGGGGTATCCACTTTCGTGTTTTCGCTATTGCTCA
TGTGTCTGTGGGCTGTTCGCTTAAACATTTTTTCCGAATACAACTAAATTCTGGCGCT
GTTGTTTTTTCGCGGATGCTTCACAAGCTCACTTCACCATGAAGTCAGCCCCCATCCA
CATCTATATCCACATCTGCAGACCCATCTCCGCACGCATCCATCTTAATTATGACTTT
TTTACGATGACAATTTCGGGCTGAGCTTTGCAAGTTGATTACACAAAAAAAACTTC
AGTTGTGGACTGTTGTCCCCAATCACGATCGCTGTTTTCTGCCACTCCTAAGCATTT
TCAAAGAATTTGTGTTTCTGGCTATTTCCCTTGTTTTCCAGCCTCCAATTCAAGTGT
AAACACAGCCGAACGATCGTCTGTTATTCATTAAGTGCAGAGAGCATTAAATTTAG
CGAACAAAGTCTTTCGTTGCCAATAAACGGACTTTATGGACAAGTAAATTAGTTTATT
GTATTTCAAAATCGCCCACTCCATGAAAATCTATAAGGTCACTATATAGCCGAAATGT
TGGCACTCCATTCGTTCTGGCACGTACGTATACAACATGATAAACAAGGAACACGCGA
TTTTAATATTCCTCAGATATTTGTTTGAATCCGAAGCGACTATAATTATCTGCGCTGT
TGCATATCCAGCTGTCGGTGTCGCGAACTCCCTTCTTTCCGACATTTTCCAGACTATC
CCTCCGATCCCCTCTTGTTGGGTTTAATTTGGATTAAGTGACAGGCAGAAGAGAAAGC
GAGAAAGAATGTTATCGGCGAGCCGAAGTTTATCTACCCTCTTGTGAAAATCAGAATA
TATTCTCGACTAATATTTGACTGGCATGTCAATTGTAAGCTGAAGCTCTGTAACTTCT
CTATTCTATTGTGTTGTATTGAGTTATATATTGAGTTGTATGAACCCAATATGGTATT
TTTCATTTATACCATTTTAACATTTTTGCTAAGAGCTGTGCACTTCTTCCGTTAAATG
TTAGTCTTTGCTTGCTTGTTGTTTTCCTGTGCAAACCTGATCGACGGGTTTTCTTTT
GGCAGTCTCTAAGTGCATTCCACATCCCGGGGACATCGGTCCCCGGTTCACTCGGCT
CTTTCTGAATGGCGGTTCTGCTAAGTTTGATTACGCCATTCTGTCAACTGTCGCCTAA
GACTTTGGGCCTGAGCAGGGCAAACAATAAAGTTGTTTGTCAATTGGTTTTACAAATA
GCCTAGTGGCCAAATACGCAACACAAACAGAGGGGCCAAACAGTAAGCCAATTAGAGA
AGATGATTGTGCGATTCTGTTTATCTTATCAGGCCGACCTTCCCACCTGGGGGGGGTC
ATTTACAAAACCCAATTTTTTGCCAAGCCAAAAACTTGGACTGATTAGCCGTTTTCA
ACGGATGGGTCGGGTATATGTTTCCTGAATACCAATTCTTCGGCTGTTGATAAATAAT
CAGAAGTGGCGTATTCAAATTAGCCAGGTCTTGAGTGTGATTAGCAGATTTCTCACAC
ATTTCAAGTATCACAGCGGTCAGTATCACTGTGGAAACGAGAATCCCCCAGAAGAAGC
CGCCTTGAAATTTACGAACAAAGCCGCCTATAAATCTCACAATTTCGGCGCCCCCATT
GCCTGAGTCGCCCCCAGGCTCCATTCGAGCCCCATCTAGAAGAGTTATCAAAGCGTAA
AGCGCAACAAATTGATTGCTAATTGATACTGATGTGTCGATTATTTTATGATTATTCT
TTATGATCGTTAGACGTTGATACCCGCACCAAACCTGATTCAAATTTAGTGGATCACT
CCGACCGCCGCCACTGCTGGTACTGGGGGCTCCAGTACCCACGTCCACCGCCGACCTT
GTCTTGTCTTCGCATGGATTGTAATAATTTAATAACTACACGGAGGAGCAAATTAAGA
CCGAATTCGGTACCACAGAAACCACTTAAGACGCTTTCTTTAATTGCCCCAAAACGG
AGATTTGGCTGTGAAGAAACCTGTAGGGCAGCTTTTTTCTCGCTCCGTTCCAGCCT
CATGTCCACTCCATGTGAAAACCATCGTAGCATGAAGCGATGTCAAATGCCGTTTTC
GAGAGCTTCCAATTCCAACCTATTGTTTTGACTTCCAAGGCCCTAAGGTCTAGTGGG
GTCACAAAGTGGCCTGAGTGAGCAATGCGGGTTCTTGCTTCATTTTCAGCTTACGTTA
CTCATTCGACGCGAATTACCTGAAGTCCAGCCCACATAGACATTGCTCATCCGATCCG
TGGCTGCTCTTTCTTTGCAGACCAAACCAATGGACTTTAACAACTGCGGCTTCATTGA
TCCGCAGGCCCAGCTAGCTGGAGCTTTGGCCAAGCAGGACATCCGACAGTTCGTTGCT
GCCCTGGACAGCGGTGCCCTGGCCGATCTACAAGACGACCGCCATACCAGTATCTACG
AGAAGGC
```

FIGURE 8D

```
ACTCTCAACACCAGGTTGTCGTGACTTCATTGAAGCCTGCATCGACCACGGCAGCCAG
GTGAACTACGTGAGTAGAGCAACAAGGAGTAGAGGTCGGACACCATCTAACCACAGTT
CATCTTCACAGATCAACAAGAAGCTGGACAAGGCCGCAATCAGCTATGCGGCTGACTC
TAGGGATCCAGGAAACCTGGCGGCTCTCCTTAAGTACCGCCCCGGAAACAAAGTCCAG
GTTGATAGAAATATGGGCAGCTTACTCCACTTAACTCACTTGCCAAGAATCTCACGG
ATGAAAATGCCCCAGACGTGTACTCCTGCATGCAACTCTTGCTGGACTACGGCGCCTC
GCCGAATATCGTAGACCAGGGCGAGTTCACACCCTTGCACCATGTGCTGAGAAAGAGC
AAGGTGAAGGCTGGGAAGAAGGAACTGATTCAGCTCTTTCTGGACCATCCGGAGCTGG
ATATCGATAGTTACCGAAACGGGGAGGTGCGCAGACTGCTGCAGGCGCAATTTCCGGA
GCTTAAGCTGCCGGAAGAGCGTCATACCGGGCCGGAGATTGACATCCAAACTCTTCAA
AGGACTCTACGGGACGGGGACGAAACACTGTTTGAGCAGCAGTTCGCTGAGTACTTGC
AGAATCTCAAAGGCGGAGCGGATAACCAACTAAATGCCCACCAGGAGGAATACTTCGG
ACTGCTGCAGGAGAGCATCAAGAGGGGCAGGCAGCGAGCCTTCGATGTCATTTTGTCC
ACTGGCATGGATATCAACTCGAGACCAGGCAGGGCCAACGAGGCCAATCTCGTAGAGA
CGGCCGTGATATACGGTAACTGGCAGGCGTTGGAGCGACTGCTTAAGGAGCCAAACCT
GCGACTTACTCCAGACTCCAAGCTACTAAATGCAGTAATCGGCCGTCTGGATGAGCCA
CCGTATGATGGCTCCAGCCACCAGCGCTGCTTTGAATTGCTCATTAACAGCGATCGCG
TAGACATCAACGAAGCTGATTCCGGACGCCTGGTGCCTCTGTTCTTCGCTGTTAAGTA
CCGCAACACGAGTGCGATGCAAAAACTCCTGAAGAACGGTGCCTACATTGGTTCTAAG
AGCGCATTTGGCACACTACCCATCAAGGACATGCCACCCGAGGTTCTCGAAGAGCACT
TCGACTCGTGTATCACCACAAACGGAGAGAGGCCTGGTGACCAGAACTTTGAGATCAT
CATCGATTATAAGAACCTAATGCGCCAGGAGAGAGACTCCGGACTCAACCAGCTGCAA
GACGAAATGGCCCCGATCGCATTCATCGCCGAGTCGAAGGAGATGCGCCACCTGCTCC
AGCACCGCTGATCTCGAGCTTTCTATTCCTCAAGTGGCACCGACTTTCCGTGATATT
CTACCTGAACTTCCTGATATACTCGCTTTTTACCGCCTCCATAATTACCTACACGCTC
CTCAAGTTCCACGAAAGCGATCAAAGGGCTCTTACTGCATTTTTCGGATTGCTTTCCT
GGCTGGGAATCAGCTACCTTATATTACGGGAGTGCATCCAGTGGATAATGTCTCCAGT
TCGGTACTTTTGGTCTATAACGAATATTATGGAGGTGGCTCTTATTACACTATCTATC
TTTACCTGCATGGAATCCAGCTTCGACAAGGAGACGCAGCGCGTCTTAGCCGTATTTA
CCATCCTACTCGTCTCCATGGAGTTTTGTTTACTAGTGGGCTCCCTGCCAGTGCTCTC
AATTTCGACGCACATGCTGATGCTGCGAGAGGTGTCAAACAGCTTCTTAAAGAGCTTT
ACCCTCTACTCGATCTTCGTGCTCACCTTCAGCCTGTGTTTCTATATCCTCTTCGGCA
AGTCAGTGGAGGAAGACCAGTCTAAAAGCGCTACGCCATGTCCACCTCTGGGGAAGAA
GGAGGGGAAGGACGAGGAACAGGGCTTCAACACATTTACCAAGCCTATCGAGGCCGTG
ATCAAGACCATTGTGATGCTGACAGGCGAGTTTGACGCCGGAAGCATCCAGTTTACCA
GCATCTACACCTACCTGATTTTCCTGCTCTTCGTGATCTTTATGACGATAGTGCTGTT
CAACCTTTTGAACGGTCTTGCAGTGAGCGACACCCAAGTAGGTCTATCGCCATTCGTA
TTATTTCCCTTCGCTAATCCCATTTCCGGCGTTATTCATTATCTAGGTTATTAAGGCT
CAGGCGGAACTGAACGGAGCCATTTGCAGAACCAACGTCCTTAGTCGGTACGAGCAGG
TTCTCACTGGCCACGGACGCGCTGGGTTTTGTTGGGCAACCATCTCTTCCGCAGCAT
CTGCCAACGTTTGATGAACATCTACCCGAACTACTTAAGTCTGCGTCAGATTTCCGTG
CTGCCGAACGATGGAAACAAAGTGCTTATTCCAATGAGCGATCCCTTCGAAATGAGGA
CCCTTAAGAAGGCTAGCTTTCAGCAATTGCCCCTGAGTGCTGCAGTGCCCCAGAAGAA
GCTGTTGGATCCACCGCTTAGACTTCTGCCCTGCTGCTGTTCCCTGCTCACCGGAAAG
TGCTCCCAGA
```

FIGURE 8E

```
TGAGCGGCCGGGTGGTCAAACGGGCCCTCGAGGTAATCGATCAGAAGAACGCGGCGGA
GCAGAGGCGGAAACAGGAACAGATCAACGACAGTCGACTGAAGCTGATCGAGTACAAG
CTGGAGCAATTAATACAGCTGGTCCAGGACCGGAAGTGATGGAGAATGTATTTTGGTA
GCTTTAGTATTTATGAGACTAATCAACCTTTTAGAACGATTTGCATTTAACATTCAGT
TTAAAGAGCCGAGTTAGTCGGAAATTGTTTTTATTAACATACGAGTAATGAAATTGAA
CAAAACCCTTAATAATTGTCAGTAAGTAAGTAGTATATAATGGTTATATAGACAGTAA
ATATTGTATAAACGAATATCATTACTGTACTATTTGTACCCGAGTAAATATTTAATTT
CAAATGTTAGATGTACGCTTTTAGAGTTTTCATTTAGTTATTCGCTTTACTTAACCA
TCTTTTATTTTGATTTGATATGATTCGGTTCAAAATGTGTGTTAGTCACATATTATGG
TTAATGAGCTCTTAATCTTTAACTTTTTGTCTTCCTTGTCTGTAATAATTCCTTTGT
TTAAGCCAGAGCTGAACTGAGCGTAGCGGACCAAATCGAATTACACGGGCGTAAAGAG
CTAACGAGGCAATCAATGGCAATGGAAAACCGACTGGAAACTTATGCAAGCTGTGCGG
TCATAATTTGTTAACAATTTTCAGCCTAATTATTTGTTTTTTATGATTTCCGACAGCA
AGGAGTAAAAAGCTTCAGGCCGTTTTATGGAGTGAGTGAAGCGCATGCATCGATTAAG
CTAAGCTAGAATACAAATTACTACTGGGCCTTAGTTTGGTTACTCGACTTGATAACGC
TCTTGATTAGCTGTGGCTGTTATTGTTATTGTTAGAGGACTAGGACTAGGACCTTTAA
AGCGGCAAATCAAAATAATTGACTTAGTTCTTGGAGCGTTTTGGACAATTGTACGACT
TGTTATTCGGTTTAAGTGGTGTTATGCGACTTATTCTGCTTCTAGTAGCGTGGCCGAT
GAAACATTAACTCCTATCTTTCGTATATACTTTAATCTCAACAATGTATATATATAAA
TAAAATCGTGTATTCTGTAAGGCATGCCTAATTAAACCAGCCGTATTGCTAACTATAG
GTGTATATTTGTGTACTTCATGTGGTTTTACTTCCTGCATCCTGCATCCACCTATCTC
TCCCAAGTCCGGGAGATTGTCTTAATGTCTTGTCTGTGTTGCGTGAGCTCTAAATGCA
TAGGATTCGGTTCTGTCTTCGCCTCCAATTCAGGTTCGCTTGCTTCGTACTGCTATCG
ACTTGACTGACTTGAGTGGGACCAAAGCCTCATCTACTGCGATTACGATTATCTAAGA
GTTAAGTTTGTCCTTGTATTCCCAGATTCTGTGTGAGTGGCCTGCCTGCTGTTATTTT
GAGTATTGGTTTCGGTAACGATGACTCGAACTTGCGTCTCTATAATTGAATATGCATC
ATTTTTTTATTGTCGTTATACTCTATGACTAAATTAAACATCCCACATCATAGCATC
GCTCCGACTGGTCTCGCCTCGCTCTGTAATCTGGTTAATCGATTTCTGTTGAAGAAAA
CTAAAATAAAAGCATTTCTCTTTTTTTTTGAGCTTTTAGTTTTTTTGTGGTTGGAATC
AGGTTCTATTGCTATTTCGTTACCATTATCATAATCGTTTTTCGTTTATGTACAATCG
AATACGAGTACGTACCAATATTAAATATCACTTAATTGACGAGTGTTTGGTTTCTGTC
TGTTTTTGGTTTTGTTTCCTTGTTAACAATTCTAATTAAAATTATGACCTTATTTTTT
GTATTTTCTGTGTAAAAATTGCAGTTAAAATCACAATTAAGTTGTTGTGTGTTCATTT
GGTTGTTTGTTTCTGGAAAAAACGTTTTAGTTGGTACCATAGAATTTCAACTTACTAT
CAATCGCTGTCTGATTGTCTGTTGTTAAGTTATGAAAGTAGAGTTAGAGTAGCAAAGT
GCCCTGAATGGCGCGGGGGTGCATAAGTTATTCGGGATTTGTTAATATTTTCCCACTC
GGAGTGTACGTTATTCACTTCTTAACTTTTTTCCTGTTCGATGTTTTAACTTAATGCG
ATCACAATGGAGACTTAAAAGAGAGAACAACACTTAAAAAGTAACAAAACAAGGCGAG
TTTCTTGGAAACTTGGCCCGTCCTAACCATTCTTAGTCGTACAATAAAGTGAGTGTAA
ATTGTAAATTATTTTGCTAAAATAGAGTTCATGTGGAAGCTTGTTGGTTGTTCATTGT
ATAGGAGACCAAAATTGTTACGTCCTGCTTTTGATTTGCTATTTTCGACTGTACTTAT
CGAAAATAAACTTAAAAACTTCATCTTCGTAAACTTCTTCTGACTGGTACTTATGTGG
ACTGCTGATTGATTACGGATTAATTTGGGTCTCGATAAGAGTGCAGTGTAGTGTGTTA
ATCCCGACTGGGATTAGGATTGATATAAATATGTAAGTGCGTTGAGTACAAAATCACT
TGACATTGTTTTTGGCTTAGTTATTACCAAAGACCAATATAATCTCTAAGATGCGTAT
CGGCCATGCATTG
```

FIGURE 8F

```
GGGATGCAAAAAAAAAAAAAAAAAAATGGTATGGCGCTACGCATCTTCGTATTTTAACG
TCTTTGTTATTACCGTTGGATGCACACGAGAAAGGGAGATGTGGATGAGGGAGGAGCC
ATAAGATATGTACAATACAATATAATAATAATCAAATCTACTAATACTTCGCTTTTGT
ACTTCGAACAATCGGTAATGGATAATATTCGCTATCGTAATCGCATTTGTAATCGGCA
ATCTTTGCGCTATCGTAACGAAAAACCTTTATAATTACTTCAATAAATTGTATCTAAC
TAACGTCATAGTCTGTAACTATAGTATTAGCTCATTAATTTAAAATACTTCCTTTGGC
ATATGTACAAATGTATTTAGATACTATTCACATATACCTTCCGTATATGCAAGTCGA
TAATTACGAAACAAACACTACAGTTATGAGCCTAGATCTAACCGCGATAGTTAGTTAC
ACATGTAATGTATGCATGTGATGCAAACCTCTACGTATTGTATAGTTCAAAAACAACC
TTCGAAAATGTGGCAGAAAGTTGGCCCACGGCAGGAGAATAGAAGGCCGTGCCTTGCC
TTCATTGCCTCACTTGTGGGTCAGGCATTCT
```

ATGCAGAATTCTCCGGCTCCGTGTGCCTGGTACTTGCCCTGGTCCCTGGCCGCCCAGC
AGCACCAGCAAAAGATGCTGCAAATGCAGTCGCCGTTTCTGGACAAGATGGGCGCCAC
ATCGGTGGGCGGCATCTTCGCTGGCCAGCCGCAGATGCAGCAACAATTGTCGCCCAAT
ACGGCAGCAGCACCGCCGGCAAACTATCAGCAGCCCGCTTTGCATCCAAGCGCCGCAC
CAGGCGCACCACACTTCCACATGGGATCCCCGTATAGCCATCTGGCACCGCAGCTCCT
CAACGCCGGACAGCTGAACCAGAACGCACTGATGCACTCCGCCATGTTCTCTTCCCTG
CCACTTGGTGCGTACTATGCACCCGCCGCCGGCGCAGGTCACTCGGCCTTTGGTGGCG
TTCCCCTGACCACGGCTGCCCAGCAATCTCTATTGGCCGCCACCGGAGGAGCAACTGC
TGGCCATTTGGCCAACCAGCAGACGACGGCTCAAGTGCCCGTCCAGGTGCCCGTGCAA
ATGGCCCAACGGACAGCTCCGGCCGCCTGCTCCATGGTCCAGCCACTTAACTGCCTGC
CGCACCAGGAACTGAATCACCTGTCGTCCATCAATCTCAACCTGCTGCGCAGTCCGGC
GCCTCCGCTCCCAGCCATTCAGGTCTTGCCAAGTGCCGAGGTGCCGATTAATAAGAAG
GTGAGTTGCAGTTTGCTTAGTACTTGTAATGATAGGCACTATTCGTACTTGAGCGAAG
GCTAG

FIGURE 10B

MQNSPAPCAWYLPWSLAAQQHQQKMLQMQSPFLDKMGATSVGGIFAGQPQMQQQLSPN
TAAAPPANYQQPALHPSAAPGAPHFHMGSPYSHLAPQLLNAGQLNQNALMHSAMFSSL
PLGAYYAPAAGAGHSAFGGVPLTTAAQQSLLAATGGATAGHLANQQTTAQVPVQVPVQ
MAQRTAPAACSMVQPLNCLPHQELNHLSSINLNLLRSPAPPLPAIQVLPSAEVPINKK
VSCSLLSTCNDRHYSYLSEG

FIGURE 11A

Upstream non coding exon

*TGCGGTCGCTTTCACGGATCAGATTAGTCGTTGTCTGGATATTAACGAGG*

FIGURE 11B

Exon 2

*AAGACCAAACCA*ATGGACTTTAACAACTGCGGCTTCATTGATCCGCAGGCCCAGCT
AGCTGGAGCTTTGGCCAAGCAGGACATCCGACAGTTCGTTGCTGCCCTGGACAGC
GGTGCCCTGGCCGATCTACAAGACGACCGCCATACCAGTATCTACGAGAAGGCA
CTCTCAACACCAGGTTGTCGTGACTTCATTGAAGCCTGCATCGACCACGGCAGCC
AGGTGAACTAC

FIGURE 11C

Exon 3

ATCAACAAGAAGCTGGACAAGGCCGCAATCAGCTATGCGGCTGACTCTAGGGAT
CCAGGAAACCTGGCGGCTCTCCTTAAGTACCGCCCCGGAAACAAAGTCCAGGTT
GATAGAAAATATGGGCAGCTTACTCCACTTAACTCACTTGCCAAGAATCTCACGG
ATGAAAATGCCCCAGACGTGTACTCCTGCATGCAACTCTTGCTGGACTACGGCGC
CTCGCCGAATATCGTAGACCAGGGCGAGTTCACACCCTTGCACCATGTGCTGAGA
AGAGCAAGGTGAAGGCTGGGAAGAAGGAACTGATTCAGCTCTTTCTGGACCAT
CCGGAGCTGGATATCGATAGTTACCGAAACGGGGAGGTGCGCAGACTGCTGCAG
GCGCAATTTCCGGAGCTTAAGCTGCCGGAAGAGCGTCATACCGGGCCGGAGATT
GACATCCAAACTCTTCAAAGGACTCTACGGGACGGGGACGAAACACTGTTTGAG
CAGCAGTTCGCTGAGTACTTGCAGAATCTCAAAGGCGGAGCGGATAACCAACTA
AATGCCCACCAGGAGGAATACTTCGGACTGCTGCAGGAGAGCATCAAGAGGGGC
AGGCAGCGAGCCTTCGATGTCATTTTGTCCACTGGCATGGATATCAACTCGAGAC
CAGGCAGGGCCAACGAGGCCAATCTCGTAGAGACGGCCGTGATATACGGTAACT
GGCAGGCGTTGGAGCGACTGCTTAAGGAGCCAAACCTGCGACTTACTCCAGACT
CCAAGCTACTAAATGCAGTAATCGGCCGTCTGGATGAGCCACCGTATGATGGCTC
CAGCCACCAGCGCTGCTTTGAATTGCTCATTAACAGCGATCGCGTAGACATCAAC
GAAGCTGATTCCGGACGCCTGGTGCCTCTGTTCTTCGCTGTTAAGTACCGCAACA
CGAGTGCGATGCAAAAACTCCTGAAGAACGGTGCCTACATTGGTTCTAAGAGCG
CATTTGGCACACTACCCATCAAGGACATGCCACCCGAGGTTCTCGAAGAGCACTT
CGACTCGTGTATCACCACAAACGGAGAGAGGCCTGGTGACCAGAACTTTGAGAT
CATCATCGATTATAAGAACCTAATGCGCCAGGAGAGAGACTCCGGACTCAACCA
GCTGCAAGACGAAATGGCCCCGATCGCATTCATCGCCGAGTCGAAGGAGATGCG
CCACCTGCTCCAGCACCCGCTGATCTCGAGCTTTCTATTCCTCAAGTGGCACCGA
CTTTCCGTGATATTCTACCTGAACTTCCTGATATACTCGCTTTTACCGCCTCCAT
AATTACCTACACGCTCCTCAAGTTCCACGAAAGCGATCAAAGGGCTCTTACTGCA
TTTTTCGGATTGCTTTCCTGGCTGGGAATCAGCTACCTTATATTACGGGAGTGCAT
CCAGTGGATAATGTCTCCAGTTCGGTACTTTTGGTCTATAACGAATATTATGGAG
GTGGCTCTTATTACACTATCTATCTTTACCTGCATGGAATCCAGCTTCGACAAGG
AGACGCAGCGCGTCTTAGCCGTATTTACCATCCTACTCGTCTCCATGGAGTTTTGT
TTACTAGTGGGCTCCCTGCCAGTGCTCTCAATTTCGACGCACATGCTGATGCTGC
GAGAGGTGTCAAACAGCTTCTTAAAGAGCTTTACCCTCTACTCGATCTTCGTGCT
CACCTTCAGCCTGTGTTTCTATATCCTCTTCGGCAAGTCAGTGGAGGAAGACCAG
TCTAAAAGCGCTACGCCATGTCCACCTCTGGGGAAGAAGGAGGGGAAGGACGAG
GAACAGGGCTTCAACACATTTACCAAGCCTATCGAGGCCGTGATCAAGACCATT
GTGATGCTGACAGGCGAGTTTGACGCCGGAAGCATCCAGTTTACCAGCATCTACA
CCTACCTGATTTTCCTGCTCTTCGTGATCTTTATGACGATAGTGCTGTTCAACCTT
TTGAACGGTCTTGCAGTGAGCGACACCCAAG

FIGURE 11D

Exon 4 with poly A tail:

```
TTATTAAGGCTCAGGCGGAACTGAACGGAGCCATTTGCAGAACCAACGTCCTTAGTCGGTACGAGCAGGT
TCTCACTGGCCACGGACGCGCTGGGTTTTTGTTGGGCAACCATCTCTTCCGCAGCATCTGCCAACGTTTG
ATGAACATCTACCCGAACTACTTAAGTCTGCGTCAGATTTCCGTGCTGCCGAACGATGGAAACAAAGTGC
TTATTCCAATGAGCGATCCCTTCGAAATGAGGACCCTTAAGAAGGCTAGCTTTCAGCAATTGCCCCTGAG
TGCTGCAGTGCCCCAGAAGAAGCTGTTGGATCCACCGCTTAGACTTCTGCCCTGCTGCTGTTCCCTGCTC
ACCGGAAAGTGCTCCCAGATGAGCGGCCGGGTGGTCAAACGGGCCCTCGAGGTAATCGATCAGAAGAACG
CGGCGGAGCAGAGGCGGAAACAGGAACAGATCAACGACAGTCGACTGAAGCTGATCGAGTACAAGCTGGA
GCAATTAATACAGCTGGTCCAGGACCGGAAGTGAGGAGAATGTATTTTGGTAGCTTTAGTATTTATGAGA
CTAATCAGCCTTTTAGAACGATTTGCATTTAACATTCAGTTTAAAGAGCCGAGTTAGTCGGAAATTGTTT
TTATTAACATACGAGTAATGAAATTGAACAAAACCCTTAATAATTGTCAGTAAGTAAGTAGTATATAATG
GTTATATAGACAGTAAATATTGTATAAACGAATATCATTACTGTACTATTTGTACCCGAGTAAATATTTA
ATTTCAAATGTTAAAAAAAAAAAAAAAA
```

METHODS AND COMPOSITIONS ASSOCIATED WITH NOCICEPTIVE PAIN

RELATED APPLICATIONS

This application claims the benefit of priority under 35 U.S.C. § 119(e) to U.S. Provisional Application 60/218,319, filed Jul. 14, 2000 and U.S. Provisional Application 60/286,726, filed Apr. 25, 2001, the entire contents of each of which is incorporated herein by reference.

ACKNOWLEDGMENT OF GOVERNMENT SUPPORT

This invention was made in part with government support under Grant No. MCB9907939 awarded by the National Science Foundation. The federal government may have certain rights in this invention.

FIELD OF THE INVENTION

The invention relates generally to nociceptive pain and disorders associated with pain and more specifically to polynucleotides that encodes polypeptides that affect nociceptive pain and methods of use therefor.

BACKGROUND

Pain has been defined in a variety of ways. For example, pain can be defined as the perception by a subject of noxious stimuli that produces a withdrawal reaction by the subject. The most commonly experienced form of pain may be defined as the effect of a stimulus on nerve endings, which results in the transmission of impulses to the cerebrum. This somatic sensation and normal function of pain, referred to as nociception or nociceptive pain, informs the organism of impending tissue damage. Somatic and visceral free nerve endings, termed nociceptors, initially process such pain signals.

Pain is a subjective experience related to perception of inputs to the central nervous system by a specific class of sensory receptors known as nociceptors. Nociceptors fire in response to noxious thermal, mechanical and chemical stimuli. Coding of a stimulus as painful occurs at several levels in the nervous system. The first is at the level of transduction of the noxious stimulus in the peripheral nerve terminals of the nociceptors. During the transduction step, the noxious stimulus is converted to an electrical stimulus in the form of an action potential. In mammals the vanilloid receptors (VR-1 and VRL-1) are proposed to function during transduction of a noxious heat stimulus. Candidate molecules for transducing noxious mechanical stimuli have yet to be identified.

The second level of coding occurs in the dorsal horn of the spinal cord. The cell bodies of nociceptive neurons are found in the dorsal root ganglia and send projections both to the periphery and to the dorsal horn. Upon stimulation nociceptors release the excitatory neurotransmitter glutamate which produces action potential sin post-synaptic cells of the dorsal horn, which project to the brain where pain is perceived. The higher level processing involved in pain perception are poorly understood. High intensity pain is signaled through increased release of substance P by the afferent nociceptive terminals in the dorsal horn. This peptide function through the G-protein couples substance P receptor, NK-1.

In general, while brain pathways governing the perception of pain are still incompletely understood, sensory afferent synaptic connections to the spinal cord, termed "nociceptive pathways" have been studied. The nociceptive pathway, which exists for protection of the organism (such as the pain experienced in response to a burn), is inactive. Activity is initiated by the application of a high intensity, potentially damaging stimulus. This stimulus serves to depolarize certain classes of afferent (sensory) axons of the small unmyelinated category, designed C fibers.

The signal carried by the C fibers travels up the peripheral nerve and into the spinal cord where synapses are made on second order and higher order neurons, which then transmit the pain signal up the spinal cord in the spinothalamic tract ending in the thalamus. Polysynaptic junctions in the dorsal horn of the spinal cord are involved in the relay and modulation of sensations of pain to various regions of the brain, including the periaqueductal grey region. The ventrolateral and ventromedial thalamic nuclei project to the cortex where the pain is then processed with regard to localization and other integrative characteristics.

Analgesia, or the reduction of pain perception, can be affected directly by decreasing transmission along such nociceptive pathways. Analgesic opiates are thought to act by mimicking the effects of endorphin or enkephalin peptide-containing neurons, which synapse presynaptically at the C-fiber terminal and which, when they fire, inhibit release of substance P from the C-fiber. Descending pathways from the brain are also inhibitory to C-fiber firing. Thus, CNS-mediated analgesia leads to an overall inhibition of the pain transmission.

While neuropathic pain is known to have a number of underlying etiologies, it is characterized by a distinct set of symptoms. As described in greater detail below, these can include enhanced sensitivity to innocuous thermal-mechanical stimuli, abnormal sensitivity to noxious stimuli, tenderness, and spontaneous burning pain. Neuropathic pain is also progressive in nature, in that it generally worsens over time. Known treatment methods treat the symptoms without necessarily lessening the underlying pathology.

Typically, chronic nociceptive pain results from changes in the peripheral sensory terminal secondary to local tissue damage. Mild damage, such as abrasions or burns, and inflammation in the cutaneous receptive fields or joints will produce significant increases in the excitability of polymodal nociceptors (C fibers) and high threshold mechanoreceptors. This increased excitability leads to increased spontaneous activity and an exaggerated response to otherwise minimal stimuli.

These events have several consequences. First, the magnitude of the pain state in humans and animals is proportional to the discharge rate in such sensory afferent. The facilitated response secondary to the local peripheral injury may lead to an exaggerated pain state simply because of the increased afferent activity. Secondly, spontaneous activity in small sensory afferent causes central neurons in the spinal cord to develop an exaggerated response to subsequent input. Both of these events, secondary to the increased spontaneous activity and reactivity in small sensory afferent generated by the peripheral injury leads to a behavioral state referred to as hyperalgesia. Thus, where the pain response is the result of an exaggerated response to a given stimulus, the organism is hyperalgesic. The importance of the hyperalgesic state in the post injury pain state has been repeatedly demonstrated and this facilitated processing appears to account for a major proportion of the post-injury/inflammatory pain state.

Despite numerous definitions, the brain pathways, mechanisms and intermediates governing the perception of pain are not completely understood. A number of analgesics and opiates are currently on the market to address the discomforts associated with pain. However, many of these agents are addictive or have side effects that often provide additional discomforts to a subject when taken over a long period of time. For example, side effects associated with a number of opiates include sedation, depression of respiration, constipation, nausea and emesis, abuse liability and the development of addiction. These effects serve to limit the utility of opiates for controlling post injury pain. Addiction liability can occur secondary to medical uses of the drug where the central effects lead to an addicted and dependent state.

Pain is a major problem for the individual sufferer and for society because of the high costs involved in managing pain. Pain is often a part of numerous disorders or diseases including, for example, cancer pathology. Terminally ill subjects often suffer immensely because our ability to effectively manage pain is inadequate. Therefore, strategies to identify molecules that function in pain sensation are needed.

SUMMARY OF THE INVENTION

In one embodiment, the invention provides an isolated nucleic acid sequence corresponding to a nociceptive pain associated locus, characterized as being inactivated by insertion of a heterologous sequence 3.6 kilobases upstream of the nucleotide sequence set forth in SEQ ID NO:1.

In another embodiment, the invention provides a method of identifying an agent that modulates nociceptive pain. The method includes contacting an organism containing a polypeptide encoded by the sequence set forth in SEQ ID NO: 2 with an agent suspected of having nociceptive pain modulating activity under conditions that allow the agent and the polypeptide to interact, measuring a nociceptive reflex response to administration of a nociceptive stimulus to the organism, and comparing the nociceptive reflex response to a nociceptive reflex response in an organism not administered the agent, wherein a change in the nociceptive reflex response is indicative of an agent that modulates nociceptive pain.

In yet another embodiment, the invention provides a method of modulating nociceptive pain in an organism. The method comprises contacting an organism containing the polypeptide encoded by the amino acid sequence set forth in SEQ ID NO:2 with a nociceptive modulating amount of an agent under conditions that allow the agent and the polypeptide to interact.

In still another embodiment, the invention provides a method of identifying an agent that modulates nociceptive pain. The method comprises contacting an organism containing a nociceptive polynucleotide sequence with a candidate agent under conditions that allow the agent and the polynucleotide to interact; measuring a nociceptive reflex response to administration of a nociceptive stimulus to the organism; and comparing the nociceptive reflex response to a nociceptive reflex response in an organism not administered a nociceptive stimulus. A change in the nociceptive reflex response is indicative of an agent that modulates nociceptive pain.

Further provided by the invention is a method of modulating nociceptive pain in an organism. The method comprises contacting an organism containing a nociceptive polynucleotide sequence with a nociceptive modulating amount of an agent under conditions that allow the agent and the polynucleotide to interact.

The invention also provides a transgenic non-human organism having a transgene disrupting expression of a polynucleotide sequence within the nociceptive pain associated locus, wherein the transgene is chromosomally integrated into the germ cells of the organism.

In yet a further embodiment, the invention provides a nucleic acid construct having a disrupted polynucleotide sequence corresponding to a nociceptive pain associated locus, wherein the polynucleotide sequence is disrupted by integration of nucleic acid sequence which inhibits expression of a functional gene product.

In yet another embodiment, the invention provides a method of producing a transgenic non-human organism. The method includes introducing into the genome of the organism a nucleic acid construct having a disrupted nociceptive pain locus, operably linked to a promoter which functions in the organism to cause the production of an RNA sequence and obtaining a transgenic organism having a disrupted nociceptive pain associated locus.

In still another embodiment, the invention provides isolated polynucleotides comprising the nucleic acid sequence set forth in SEQ ID NO:1 and about 260 base pairs flanking the nucleic acid at the 3' end and about 63 base pairs base pairs flanking the nucleic acid sequence at the 5' end, isolated polynucleotides comprising about 63 base pair non-coding exon located about 3.6 kilobases upstream of the coding region of CG 15860, isolated polynucleotides comprising about 260 base pair untranslated regions located 3' of the coding region of CG15860, and isolated polynucleotides wherein the polynucleotide has the sequence comprising genomic DNA including the coding region of painless.

BRIEF DESCRIPTION OF THE FIGURES

FIG. 4 shows that md-neurons are essential for nociception. Responses to a probe heated to 45° C. of normal larvae and larvae having mutations were assessed. FIG. 4C shows the control for FIG. 3B, inactive tetanus toxin, with a mutation in the catalytic domain, is ineffective. FIG. 4D shows that UAS-tetanus toxin without any driver also has no effect. FIG. 4E shows the response time of painless[1] driven by md-Gal4. FIG. 4F shows the response time of md-gal4/painless[3] larvae are normal. FIG. 4G shows that the effect seen in FIG. 3E is not due to a dominant effect of painless[1]: heterozygotes without the md-gal4 driver are normal. FIG. 4H shows that ELAV-gal4; painless[1] larvae fail to respond to the probe. FIG. 4I shows that ELAV-Gal4; painless[1] larvae also show insensitivity to a 48° C. probe. FIG. 4J shows that the response of ELAV-Gal4; painless[1] larvae to a 52° C. probe resembles that of wild type although slightly delayed.

FIG. 5 shows the amino acid sequence (SEQ ID NO:2) of the CG1580 gene product in Drosophila mealnogaster (Accession Number AAF47293).

FIG. 6 shows the nucleic acid sequence (SEQ ID NO: 1) of mRNA from Drosophil melanogaster genomic scaffold 142000013386038 section 14 of 15 (Accession Number AE003465).

FIG. 7 shows the nucleic acid sequence (SEQ ID NO:3) of the 3.0 kilobase painless transcript with 5' and 3' untranslanted regions (UTR).

FIGS. 8A–F show the genomic sequence (SEQ ID NO:8) of the painless locus.

FIG. 9 shows an amino acid alignment of the painless protein (CG15860) (SEQ ID NO:2) with ankryin-like protein I (SEQ ID NO:12) and VR-1 (SEQ ID NO:13). Putative transmembrane regions are indicated by boxes. A putative hydrophobic ligand binding pocket is indicated by a dashed box. Amino acids conserved between proteins are also boxed.

FIG. 10A shows the nucleotide sequence (SEQ ID NO:9) and FIG. 10B shows the amino acid sequence (SEQ ID NO:10) of a third transcription unit in the vicinity of E7-2-36.

FIG. 11 shows the nucleotide sequences of painless exons. FIG. 11A shows the upstream non-coding exon (SEQ ID NO:4). FIG. 11B shows exon 2 (SEQ ID NO:5). FIG. 11C shows exon 3 (SEQ ID NO:6), FIG. 11D shows exon 4 (SEQ ID NO:7). Sequence not predicted by BDGP shown in italics. The start of translation is shown in bold (ATG).

DETAILED DESCRIPTION OF THE INVENTION

Figure 1E:
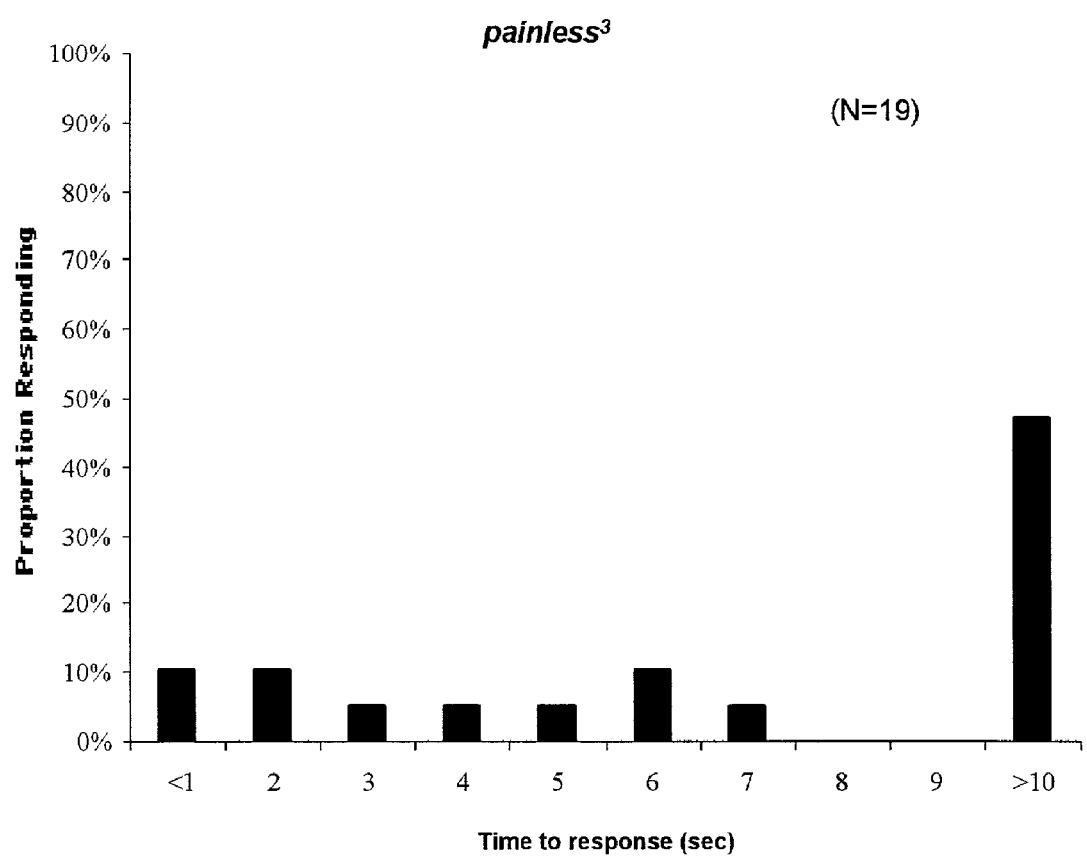
FIG. 1 shows an analysis of videotaped behavior that used to generate frequency distributions of the response times of larvae stimulated with a noxious probe heated to 46° C.
FIG. 1A shows the response time of wild type Canton-S larvae.
FIG. 1B shows the response times of larvae homozygous mutant for painless[1].
FIG. 1C shows that there is reversion of the painless phenotype in the precise excision allele painless$^{ex36}$. FIGS. D and E show that the response time of two independent alleles of painless, painless[2] and painless[3] display the same insensitive phenotype as seen in painless[1].
Figure 2A:
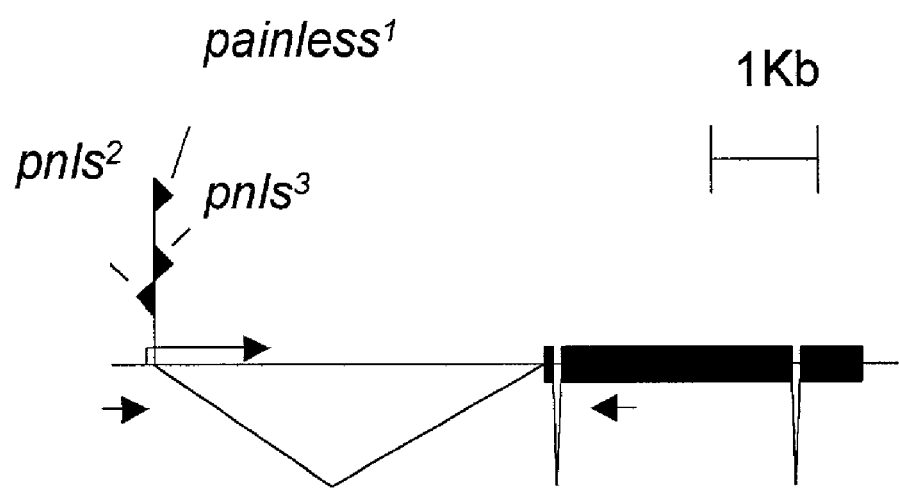
FIG. 2A is a schematic of the genomic structure of the painless locus as determined by comparison of cDNA clones identified herein with the published genomic sequence of the region. Locations of P-element insertions are indicated by flags. Location of PCR primers used in panel D are indicated as arrows.
Figure 2B:
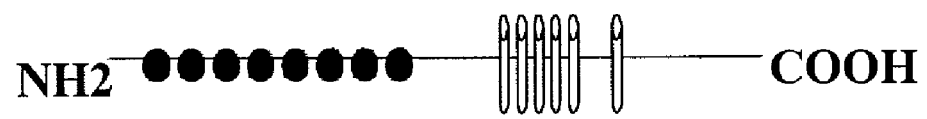
FIG. 2B is a schematic of the predicted painless protein, ankryin repeats are represented by black ovals and predicted transmembrane domains are indicated by cylinders.
Figure 2C:
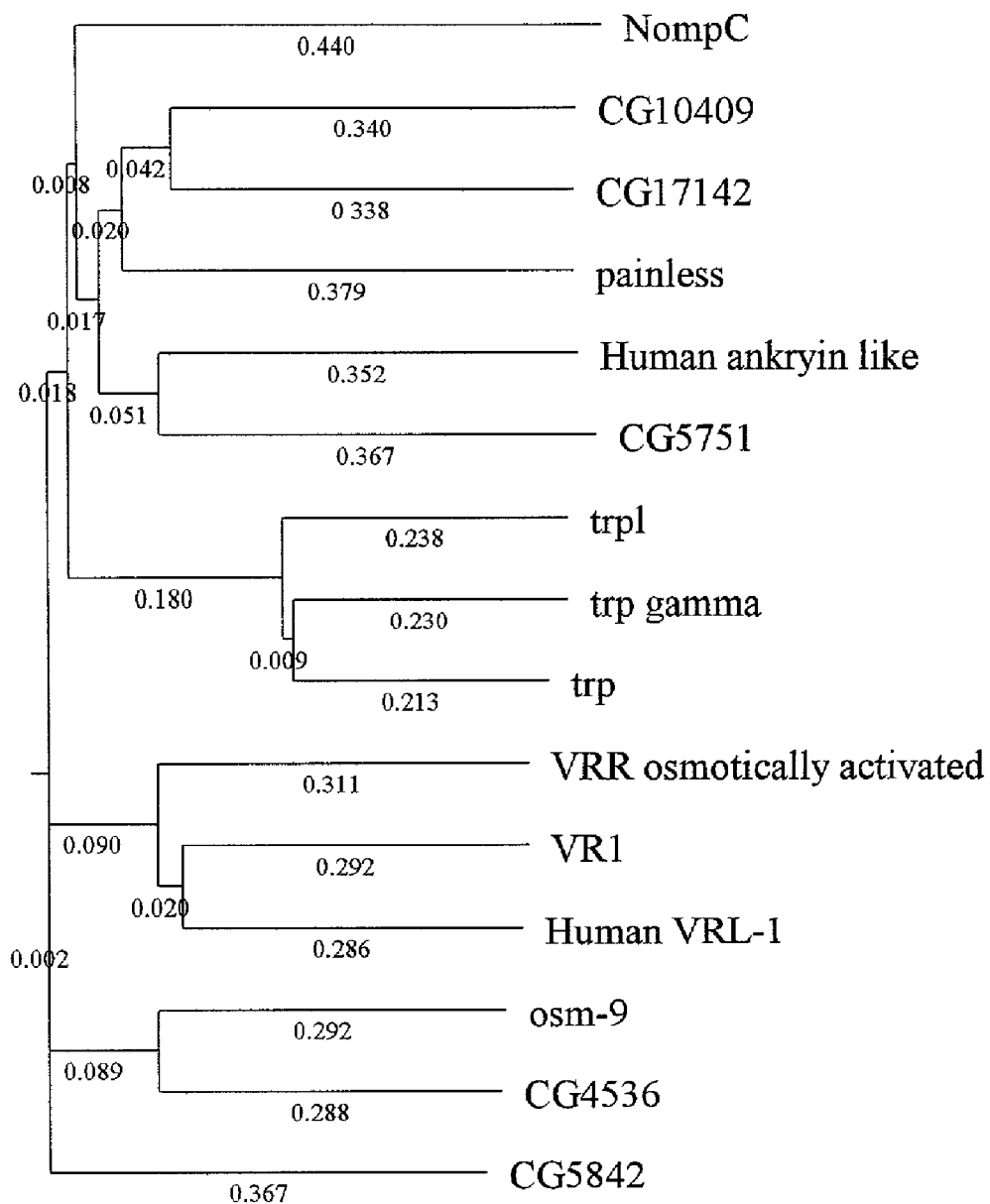
FIG. 2C shows a comparison of the TRP channel region of painless and the *Drosophila* genes: NompC, CG10409, CG17142, CG5751, trp, trpl, trp gamma, CG4536, and CG5842. The non-*Drosophila* genes included in the analysis were the Human ankyrin like, VRL-1, VR-1, VRR, and *C. elegans* osm-9. Note that the human ankyrin-like protein falls within a lade containing painless but that the other human homologues of painless are more closely related to each other, suggesting that they may have originated form gene duplications within the vertebrate lineage. Data analysis was performed using ClustalW identity matrix within the MacVector software package

In humans and other vertebrates, painful stimuli are sensed by specialized neurons known as nociceptors, which fire in response to noxious heat, mechanical, or chemical stimuli which have the potential to cause tissue damage. The signals are in turn processed by the central nervous system and perceived as pain which serves an indispensable protective role. Nociceptors are also involved in pathological pain states caused by inflammation, nerve damage, or cancer. An increased understanding of nociception therefore is of wide interest, and model systems for molecular genetic analysis are desirable. By reverse genetic approaches, several genes thought to be important to pain pathways have been disrupted in the mouse. To identify previously unsuspected genes as candidate regulators of nociception, a forward genetic approach can be useful. Drosophila genetics has facilitated the identification of molecules important to biological processes for which suitable screening paradigms have been developed. Mutations specifically affecting complex systems controlling circadian rhythms, learning and memory, and membrane excitability have been isolated, and many of the gene products involved have been found to function analogously in mammalian models. The present invention provides genomic sequences, gene sequences, and amino acid sequences related to nociception in Drosophila, and methods of using such sequences in assays to identify compounds that modulate nociception.

As used herein, hyperalgesia or a hyperalgesic state refers to a condition in which a warm-blooded animal is extremely sensitive to mechanical, chemical or thermal stimulation that, absent the condition, would be painless. Typical models for such a hyperalgesic state include the inflamed rat paw compression model and the compression of the inflamed knee joint.

Hyperalgesia is known to accompany certain physical injuries to the body, for example the injury inevitably caused by surgery. Hyperalgesia is also known to accompany certain inflammatory conditions in man such as arthritic and rheumatic disease. Hyperalgesia, thus refers to mild to moderate pain to severe pain such as the pain associated with, but not limited to, inflammatory conditions (e.g., such as rheumatoid arthritis and osteoarthritis), postoperative pain, post-partum pain, the pain associated with dental conditions (e.g., dental caries and gingivitis), the pain associated with burns, including but not limited to sunburns, abrasions, contusions and the like, the pain associated with sports injuries and sprains, inflammatory skin conditions, including but not limited to poison ivy, and allergic rashes and dermatitis, and other such pain that increases sensitivity to mild stimuli.

The methods and composition of the invention are based on a method, described herein, to measure nociceptive reflexes in invertebrates such as, for example, Drosophila melanogaster. By using P-element mutational analysis of

*Drosophila* the inventors have identified a genetic locus associated with nociceptive pain. Accordingly, the invention provides isolated polypeptides and polynucleotides associated with nociception as well as methods of identifying or screening agents that modulate nociception.

Described herein is a nocicieptive pain locus associated with the gene product CG15860 (Accession Number AAF47293, which is incorporated by reference herein in its entirety. This nocicieptive pain locus is inactivated by insertion of a P-element about 3.6 kilobases (Kb) upstream of the start codon of CG15860. Also included is a nociceptive pain locus found beginning at base 134,209 of BACR48K04 (GenBank accession # AC007451, which is incorporated herein by reference in its entirety). This nociceptive pain locus is inactivated by insertion of a heterolgous sequence at base 134,209 of BACR48K04 (GenBank Accession #AC007451).

The painless gene locus is consistent with predicted protein CG15860. A BLAST database search reveals that the closes protein relative of known function are ion channels of the transient receptor potential (TRP)/vanilloid receptor family. Like members of the receptor family, the predicted painless protein contains ankryin repeats at its amino terminus and a TRP-like ion channel domain near its carboxyl-terminus.

The nociceptive pain locus beginning at base 134,209 of BACR48K0 is associated with two putative transcription units. The genescan sequence predicts proteins from these transcription units, which are highly similar to each other. Both genes encode proteins with high similarity to the yeast gene RIB2P also known as DRAP deaminase. Yeast mutants in RIB2P are reported to be auxotrophic for riboflavin. However, a direct biochemical demonstration of a role of this protein in riboflavin biosynthesis, per se is lacking. Domains present in these predicted proteins include a double stranded RNA binding domain, a pseudouridine synthase domain, and a deaminase domain. It is thus possible that these proteins play a role in RNA editing.

The insertion is about 900 base pairs from the putative transcriptional start site of a transcript tentatively named DRAP deaminase 1 and approximately 2000 base pairs from a putative transcript named DRAP deaminase 2. Several EST's exist in the region of DRAP deaminase 2, LD40728, GM07410, LD19773 and GM09695, all of which are incorporated herein by reference.

The term "isolated" means altered "by the hand of man" from its natural state; i.e., if it occurs in nature, it has been changed or removed from its original environment, or both. For example, a naturally occurring polynucleotide or a polypeptide naturally present in a living animal in its natural state is not "isolated", but the same polynucleotide or polypeptide separated from the coexisting materials of its natural state is "isolated", as the term is employed herein. As part of or following isolation, a polynucleotide can be joined to other polynucleotides, such as for example DNAs, for mutagenesis studies, to form fusion proteins, and for propagation or expression of the polynucleotide in a host. The isolated polynucleotides, alone or joined to other polynucleotides, such as vectors, can be introduced into host cells, in culture or in whole organisms. Such polynucleotides, when introduced into host cells in culture or in whole organisms, still would be isolated, as the term is used herein, because they would not be in their naturally occurring form or environment. Similarly, the polynucleotides and polypeptides may occur in a composition, such as a media formulation (solutions for introduction of polynucleotides or polypeptides, for example, into cells or compositions or solutions for chemical or enzymatic reactions).

Polynucleotide or nucleic acid sequence refers to a polymeric form of nucleotides. In some instances a polynucleotide refers to a sequence that is not immediately contiguous with either of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the invention can be ribonucleotides, deoxyribonucleotides, or modified forms of either nucleotide. In addition, the polynucleotide sequence involved in producing a polypeptide chain can include regions preceding and following the coding region (leader and trailer) as well as intervening sequences (introns) between individual coding segments (exons) depending upon the source of the polynucleotide sequence.

The term polynucleotide(s) generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

In addition, the polynucleotides or nucleic acid sequences may contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

Nucleic acid sequences can be created which encode a fusion protein and can be operatively linked to expression control sequences. "Operatively linked" refers to a juxtaposition wherein the components so described are in a relationship permitting them to function in their intended manner. For example, a coding sequence is "operably linked" to another coding sequence when RNA polymerase will transcribe the two coding sequences into a single mRNA, which is then translated into a single polypeptide having amino acids derived from both coding sequences. The coding sequences need not be contiguous to one another so long as the expressed sequences ultimately process to produce the desired protein. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked.

Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the of the polynucleotide sequence. Both constitutive and inducible promoters, are included in the invention (see e.g., Bitter et al., Methods in Enzymology 153:516–544, 1987). For example, when cloning in bacterial systems, inducible promoters such as pL of bacteriophage, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

A nucleic acid sequence of the invention including, for example, a polynucleotide encoding a fusion protein, may be inserted into a recombinant expression vector. A recombinant expression vector generally refers to a plasmid, virus or other vehicle known in the art that has been manipulated by insertion or incorporation of a nucleic acid sequences. For example, a recombinant expression vector of the invention includes a polynucleotide sequence encoding a polypeptide involved in nociception or a fragment thereof. The expression vector typically contains an origin of replication, a promoter, as well as specific genes that allow phenotypic selection of the transformed cells. Vectors suitable for use in the invention include, but are not limited to the T7-based expression vector for expression in bacteria (Rosenberg, et al., Gene 56:125, 1987), the pMSXND expression vector for expression in mammalian cells (Lee and Nathans, J. Biol. Chem. 263:3521, 1988), baculovirus-derived vectors for expression in insect cells, cauliflower mosaic virus, CaMV; tobacco mosaic virus, TMV. The nucleic acid sequences of the invention can also include a localization sequence to direct the indicator to particular cellular sites by fusion to appropriate organellar targeting signals or localized host proteins. For example, a polynucleotide encoding a localization sequence, or signal sequence, can be used as a repressor and thus can be ligated or fused at the 5' terminus of a polynucleotide encoding a polypeptide of the invention such that the localization or signal peptide is located at the amino terminal end of a resulting polynucleotide/polypeptide. The construction of expression vectors and the expression of genes in transfected cells involves the use of molecular cloning techniques also well known in the art. (See, for example, Sambrook et al., Molecular Cloning—A Laboratory Manual, Cold Spring Harbor Laboratory, Cold Spring Harbor, N.Y., 1989, and Current Protocols in Molecular Biology, M. Ausubel et al., eds., (Current Protocols, a joint venture between Greene Publishing Associates, Inc. and John Wiley & Sons, Inc., most recent Supplement)). These methods include in vitro recombinant DNA techniques, synthetic techniques and in vivo recombination/genetic recombination. (See also, Maniatis, et al., Molecular Cloning A Laboratory Manual, Cold Spring Harbor Laboratory, N.Y., 1989).

In yeast, a number of vectors containing constitutive or inducible promoters may be used. For a review see, Current Protocols in Molecular Biology, Vol. 2, Ed. Ausubel, et al., Greene Publish. Assoc. & Wiley Interscience, Ch. 13, 1988; Grant, et al., "Expression and Secretion Vectors for Yeast," in Methods in Enzymology, Eds. Wu & Grossman, 1987, Acad. Press, N.Y., Vol. 153, pp. 516–544, 1987; Glover, DNA Cloning, Vol. II, IRL Press, Wash., D.C., Ch. 3, 1986; and Bitter, "Heterologous Gene Expression in Yeast," Methods in Enzymology, Eds. Berger & Kimmel, Acad. Press, N.Y., Vol. 152, pp. 673–684, 1987; and The Molecular Biology of the Yeast *Saccharomyces*, Eds. Strathern et al, Cold Spring Harbor Press, Vols. I and II, 1982. A constitutive yeast promoter such as ADH or LEU2 or an inducible promoter such as GAL may be used ("Cloning in Yeast," Ch. 3, R. Rothstein In: DNA Cloning Vol. 11, A Practical Approach, Ed. DM Glover, IRL Press, Wash., D.C., 1986). Alternatively, vectors may be used which promote integration of foreign DNA sequences into the yeast chromosome.

An alternative expression system which could be used to express a nociception-related polypeptide of the invention is an insect system. In one such system, *Autographa californica* nuclear polyhedrosis virus (AcNPV) is used as a vector to express foreign or mutated polynucleotide sequences. The virus grows in Spodoptera frugiperda cells. The sequence encoding a protein of the invention may be cloned into non-essential regions (for example, the polyhedrin gene) of the virus and placed under control of an AcNPV promoter (for example the polyhedrin promoter). Successful insertion of the sequences coding for a protein of the invention will result in inactivation of the polyhedrin gene and production of non-occluded recombinant virus (i.e., virus lacking the proteinaceous coat coded for by the polyhedrin gene). These recombinant viruses are then used to infect *S. frugiperda* cells in which the inserted gene is expressed, see Smith, et al., J. Viol. 46:584, 1983; Smith, U.S. Pat. No. 4,215,051.

The vectors of the invention can be used to transform a host cell. By transform or transformation is meant a permanent or transient genetic change induced in a cell following incorporation of new DNA (i.e., DNA exogenous to the cell). Where the cell is a mammalian cell, a permanent genetic change is generally achieved by introduction of the DNA into the genome of the cell.

A transformed cell or host cell generally refers to a cell (e.g., prokaryotic or eukaryotic) into which (or into an ancestor of which) has been introduced, by means of recombinant DNA techniques, a DNA molecule encoding a nociception-related polypeptide or a fragment thereof.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbC1 can be used. Transformation can also be performed after forming a protoplast of the host cell or by electroporation.

When the host is a eukaryote, methods of transfection or transformation with DNA include calcium phosphate coprecipitates, conventional mechanical procedures such as microinjection, electroporation, insertion of a plasmid encased in liposomes, or virus vectors, as well as others known in the art, may be used. Eukaryotic cells can also be cotransfected with DNA sequences encoding a nociception-related polypeptide and a second foreign DNA molecule encoding a selectable marker, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982). Typically, a eukaryotic host will be utilized as the host cell. The eukaryotic cell may be a yeast cell (e.g., *Saccharomyces cerevisiae*), an insect cell (e.g., *Drosophila* sp.) or may be a mammalian cell, including a human cell.

Eukaryotic systems, and mammalian expression systems, allow for post-translational modifications of expressed mammalian proteins to occur. Eukaryotic cells which possess the cellular machinery for processing of the primary transcript, glycosylation, phosphorylation, and, advantageously secretion of the gene product should be used. Such host cell lines may include, but are not limited to, CHO, VERO, BHK, HeLa, COS, MDCK, Jurkat, HEK-293, and W138.

Mammalian cell systems which utilize recombinant viruses or viral elements to direct expression may be engineered. For example, when using adenovirus expression vectors, a polynucleotide encoding a nociception-related polypeptide may be ligated to an adenovirus transcription/translation control complex, e.g., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing a nociception-related polypeptide or a fragment thereof in infected hosts (e.g., see Logan & Shenk, Proc. Natl. Acad. Sci. USA, 81:3655–3659, 1984). Alternatively, the vaccinia virus 7.5K promoter may be used. (e.g., see, Mackett, et al., Proc. Natl. Acad. Sci. USA, 79:7415–7419, 1982; Mackett, et al., J. Virol. 49:857–864, 1984; Panicali, et al., Proc. Natl. Acad. Sci. USA 79:4927–4931, 1982). Of particular interest are vectors based on bovine papilloma virus which have the ability to replicate as extrachromosomal elements (Sarver, et al., Mol. Cell. Biol. 1:486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of a nociception-related gene in host cells (Cone & Mulligan, Proc. Natl. Acad. Sci. USA, 81:6349–6353, 1984). High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, host cells can be transformed with the cDNA encoding a nociception-related polypeptide controlled by appropriate expression control elements (e.g., promoter, enhancer, sequences, transcription terminators, polyadenylation sites, etc.), and a selectable marker. The selectable marker in the recombinant vector confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including, but not limited to, the herpes simplex virus thymidine kinase (Wigler, et al., Cell, 11:223, 1977), hypoxanthine-guanine phosphoribosyltransferase (Szybalska & Szybalski, Proc. Natl. Acad. Sci. USA, 48:2026, 1962), and adenine phosphoribosyltransferase (Lowy, et al., Cell, 22:817, 1980) genes can be employed in tk-, hgprt- or aprt-cells respectively. Also, anti-metabolite resistance can be used as the basis of selection for dhfr, which confers resistance to methotrexate (Wigler, et al., Proc. Natl. Acad. Sci. USA, 77:3567, 1980; O'Hare, et al., Proc. Natl. Acad. Sci. USA, 8:1527, 1981); gpt, which confers resistance to mycophenolic acid (Mulligan & Berg, Proc. Natl. Acad. Sci. USA, 78:2072, 1981; neo, which confers resistance to the aminoglycoside G-418 (Colberre-Garapin, et al., J. Mol. Biol. 150:1, 1981); and hygro, which confers resistance to hygromycin (Santerre, et al., Gene 30:147, 1984) genes. Recently, additional selectable genes have been described, namely trpB, which allows cells to utilize indole in place of tryptophan; hisD, which allows cells to utilize histinol in place of histidine (Hartman & Mulligan, Proc. Natl. Acad. Sci. USA 85:8047, 1988); and ODC (ornithine decarboxylase) which confers resistance to the ornithine decarboxylase inhibitor, 2-(difluoromethyl)-DL-ornithine, DFMO (McConlogue L., In: Current Communications in Molecular Biology, Cold Spring Harbor Laboratory, ed., 1987).

The term "primer" as used herein refers to an oligonucleotide, whether natural or synthetic, which is capable of acting as a point of initiation of synthesis when placed under conditions in which primer extension is initiated or possible. Synthesis of a primer extension product which is complementary to a nucleic acid strand is initiated in the presence of nucleoside triphosphates and a polymerase in an appropriate buffer at a suitable temperature. For instance, if a nucleic acid sequence is inferred from a protein sequence, a primer generated to synthesize nucleic acid sequence encoding the protein sequence is actually a collection of primer oligonucleotides containing sequences representing all possible codon variations based on the degeneracy of the genetic code. One or more of the primers in this collection will be homologous with the end of the target sequence. Likewise, if a "conserved" region shows significant levels of polymorphism in a population, mixtures of primers can be prepared that will amplify adjacent sequences.

A polypeptide or protein refers to a polymer in which the monomers are amino acid residues which are joined together through amide bonds. When the amino acids are alpha-amino acids, either the L-optical isomer or the D-optical isomer can be used, the L-isomers being typical. A nociception-related polypeptide is intended to encompass any amino acid sequence and include modified sequences such as glycoproteins, which provides a polypeptide having nociception modulating activity. Accordingly, the polypeptides of the invention are intended to cover naturally occurring proteins, as well as those that are recombinantly or synthetically synthesized. In addition, a nociception-related polypeptide can occur in at least two different conformations wherein both conformations have the same or substantially the same amino acid sequence but have different three dimensional structures so long as the have a biological activity related to nociception. Polypeptide or protein fragments are also encompassed by the invention. Fragments can have the same or substantially the same amino acid sequence as the naturally occurring protein. A polypeptide or peptide having substantially the same sequence means that an amino acid sequence is largely, but not entirely, the same, but retains a functional activity of the sequence to which it is related. In general polypeptides of the invention include peptides, or full length protein, that contains substitutions, deletions, or insertions into the protein backbone, that would still have an approximately 70%–90% homology to the original protein over the corresponding portion. A yet greater degree of departure from homology is allowed if like-amino acids, i.e. conservative amino acid substitutions, do not count as a change in the sequence.

A polypeptide may be substantially related but for a conservative variation, such polypeptides being encompassed by the invention. A conservative variation denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. Other illustrative examples of conservative substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine to leucine. The term "conservative variation" also includes the use of a substituted amino acid in place of an unsubstituted parent amino acid provided that antibodies raised to the substituted polypeptide also immunoreact with the unsubstituted polypeptide.

Modifications and substitutions are not limited to replacement of amino acids. For a variety of purposes, such as increased stability, solubility, or configuration concerns, one skilled in the art will recognize the need to introduce, (by deletion, replacement, or addition) other modifications. Examples of such other modifications include incorporation of rare amino acids, dextra-amino acids, glycosylation sites, cytosine for specific disulfide bridge formation. The modified peptides can be chemically synthesized, or the isolated gene can be site-directed mutagenized, or a synthetic gene can be synthesized and expressed in bacteria, yeast, baculovirus, tissue culture and so on.

In one embodiment, the invention provides an isolated polynucleotide sequence encoding a nociception-related polypeptide. A nociception-related polypeptide can be characterized by its ability to modulate nociceptive reflexes. Polynucleotide sequences of the invention include DNA, cDNA and RNA sequences which encode a nociceptive-related polypeptide of the invention as well as complementary sequences thereof. It is understood that all polynucleotides encoding all or a portion of a nociception-related polypeptide are also included herein, so long as they encode a polypeptide with nociceptive activity (e.g., modulation of nociceptive reflexes). Such polynucleotides include naturally occurring, synthetic, and intentionally manipulated polynucleotides. For example, a nociceptive polynucleotide of the invention may be subjected to site-directed mutagenesis. The polynucleotides of the invention include sequences that are degenerate as a result of the genetic code. There are 20 natural amino acids, most of which are specified by more than one codon. Therefore, all degenerate nucleotide sequences are included in the invention so long as the amino acid sequence of a nociception-related polypeptide of the invention encoded by the nucleotide sequence is functionally unchanged. In addition, polypeptide fragments of a nociception-related polypeptide of the invention, and their corresponding polynucleotide sequences are encompassed by the current invention, so long as the polypeptides retain some biological activity related to nociception. A biological activity related to nociception includes for example, antigenicity or the ability to modulate nociceptive reflexes. Assays described in the examples below are capable of identifying such fragments or modified polypeptides having a biological activity related to nociception. For example, a polypeptide that modulates a nociceptive reflex (e.g., the rolling response of *Drosophila* larvae) is encompassed by the invention whether it is expressed in vivo by the organism or administered to the organism.

The polynucleotides and polypeptides of this invention were originally recovered from *Drosophila melanogaster*. Thus, the present invention provides means for isolating the nucleic acid molecules from other organisms, including humans, encoding the polypeptides of the present invention. For example, one may probe a gene library with a natural or artificially designed probe using art recognized procedures (see, for example: Current Protocols in Molecular Biology, Ausubel F. M. et al. (Eds.) Green Publishing Company Assoc. and John Wiley Interscience, New York, 1989, 1992). It is appreciated by those skilled in the art that probes can be designed based on the degeneracy of the genetic code to a sequences corresponding to a polypeptide or polynucleotide of the invention.

In addition, sequencing algorithms can be used to measure homology or identity between known and unknown sequences. Such methods and algorithms are useful in identifying corresponding sequences present in other organisms. Homology or identity is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated.

Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequence for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of person & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

On example of a useful algorithm is BLAST and BLAST 2.0 algorithms, which are described in Altschul et al., Nuc. Acids Res. 25:3389–3402 (1977) and Altschul et al., J. Mol. Biol. 215:403–410 (1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) or 11, an expectation (E) or 10, M=5, N=−4 and a comparison of both strands. For amino acid sequences, the BLASTP program uses as defaults a wordlength of 3, and expectations (E) of 10, and the BLOSLUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Natl. Acad. Sci. USA 90:5873 (1993)). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project (J. Roach, http://weber.u.Washington.edu/~roach/human_genome_progress2.html) (Gibbs, 1995). At least twenty-one other genomes have already been sequenced, including, for example, *M. genitalium* (Fraser et al., 1995), *M. jannaschii* (Bult et al., 1996), *H. influenzae* (Fleischmann et al., 1995), *E. coli* (Blattner et al., 1997), and yeast (*S. cerevisiae*) (Mewes et al., 1997), and *D. melanogaster* (Adams et al., 2000). Significant progress has also been made in sequencing the genomes of model organism, such as mouse, *C. elegans, Arabadopsis* sp. and *D. melanogaster*. Several databases containing genomic information annotated with some functional information are maintained by different organization, and are accessible via the internet, for example, at the uniform resource locator (url) world wide web.tigr.org/tdb; world wide web.genetics.wisc.edu; genome-world wide web.stanford. edu/~ball; http://hiv-web.lanl.gov; world wide web.ncbi.nlm.nih.gov; http://www.ebi.ac.uk; http://Pasteur.fr/other/biology; and world wide web site genome.wi.mit.edu.

A "substantially pure polypeptide" is typically pure when it is at least 60%, by weight, free from the proteins and naturally-occurring organic molecules with which it is naturally associated. Preferably, the preparation is at least 75%, more preferably at least 90%, and most preferably at least 99%, by weight, a nociception-related polypeptide. A substantially pure nociception-related polypeptide may be obtained, for example, by extraction from a natural source (e.g., an insect cell); by expression of a recombinant nucleic acid encoding an nociception-related polypeptide; or by chemically synthesizing the protein. Purity can be measured by any appropriate method, e.g., by column chromatography, polyacrylamide gel electrophoresis, or by HPLC analysis.

In addition to polypeptides of the invention, specifically disclosed herein is a DNA sequence for a nociception-related polypeptide. DNA sequences of the invention can be obtained by several methods. For example, the DNA can be isolated using hybridization or computer-based techniques which are well known in the art. These include, but are not limited to: 1) hybridization of genomic libraries with probes to detect homologous nucleotide sequences; 2) antibody screening of expression libraries to detect cloned DNA fragments with shared structural features; 3) polymerase chain reaction (PCR) on genomic DNA using primers capable of annealing to the DNA sequence of interest; and 4) computer searches of sequence databases for similar sequences as described above.

The polynucleotide encoding a nociception-related polypeptide include complementary polynucleotide sequences, as well as splice variants thereof. When the sequence is RNA, the deoxyribonucleotides A, G, C, and T are replaced by ribonucleotides A, G, C, and U, respectively. Also included in the invention are fragments (portions) of the above-described nucleic acid sequences that are at least 15 bases in length, which is sufficient to permit the fragment to selectively hybridize to DNA that encodes a polypeptide sequence of the invention. "Selective hybridization" as used herein refers to hybridization under moderately stringent or highly stringent physiological conditions (See, for example, the techniques described in Maniatis et al., 1989 Molecular Cloning A Laboratory Manual, Cold Spring Harbor Laboratory, N.Y., incorporated herein by reference), which distinguishes related from unrelated nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

Oligonucleotides encompassed by the present invention are also useful as primers for nucleic acid amplification reactions. In general, the primers used according to the method of the invention embrace oligonucleotides of sufficient length and appropriate sequence which provides specific initiation of polymerization of a significant number of nucleic acid molecules containing the target nucleic acid under the conditions of stringency for the reaction utilizing the primers. In this manner, it is possible to selectively amplify the specific target nucleic acid sequence containing the nucleic acid of interest.

Amplified products may be detected by Southern blot analysis, without using radioactive probes. In such a process, for example, a small sample of DNA containing a very low level of a nucleotide sequence is amplified and analyzed via a Southern blotting technique known to those of skill in the art. The use of non-radioactive probes or labels is facilitated by the high level of the amplified signal.

The nociception-related polynucleotides of the invention are derived from an insect (e.g., *Drosophila*). Screening procedures which rely on nucleic acid hybridization make it possible to isolate any gene sequence from any organism, provided the appropriate probe is available. For example, it is envisioned that such probes can be used to identify other homologs of the nociception-related polynucleotide family of factors in insects or, alternatively, in other organisms such as mammals, e.g., humans. In accomplishing this, alignment algorithms (as described above) can be used to screen genome databases. Alternatively, oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of DNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., Nucl. Acid Res., 9:879, 1981).

When the entire sequence of amino acid residues of the desired polypeptide is not known, the direct synthesis of DNA sequences is not possible and the method of choice is use of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned.

DNA sequences encoding a nociception-related polypeptide can be expressed in vitro by DNA transfer into a suitable host cell, as described above.

In the invention, the nociception-related polynucleotide sequences may be inserted into a recombinant expression vector. The term "recombinant expression vector" refers to a plasmid, virus or other vehicle known in the art that has been manipulated by insertion or incorporation of the nociception-related genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include those described above.

Polynucleotide sequences encoding a nocicpetion-related polypeptide can be expressed in either prokaryotes or eukaryotes. Hosts can include microbial, yeast, insect and mammalian organisms. Such vectors are used to incorporate DNA sequences of the invention.

Methods which are well known to those skilled in the art can be used to construct expression vectors containing the nociception-related polypeptide coding sequence and appropriate transcriptional/translational control signals. These methods include in vitro recombinant DNA techniques, synthetic techniques, and in vivo recombination/genetic techniques. (See, for example, the techniques described in Maniatis et al., 1989, Molecular Cloning A Laboratory Manual, Cold Spring Harbor Laboratory, N.Y.).

The genetic construct can be designed to provide additional benefits, such as, for example addition of C-terminal or N-terminal amino acid residues that would facilitate purification by trapping on columns or by use of antibodies. All those methodologies are cumulative. For example, a synthetic gene can later be mutagenized. The choice as to the method of producing a particular construct can easily be made by one skilled in the art based on practical considerations: size of the desired peptide, availability and cost of starting materials, etc. All the technologies involved are well established and well known in the art. See, for example, Ausubel et al., Current Protocols in Molecular Biology, Volumes 1 and 2 (1987), with supplements, and Maniatis et al., Molecular Cloning, a Laboratory Manual, Cold Spring Harbor Laboratory (1989). Yet other technical references are known and easily accessible to one skilled in the art.

In another embodiment, the invention provides antibodies that bind to a nociception-related polypeptide of the invention. Such antibodies are useful for research and diagnostics in the study of pain, nociceptive reflexes, central nervous system regulation and modulation of pain, and nociceptive-associated pathologies in general. For exanle, the invention allows for the diagnosis in a subject of hyperalgesia associated with improper nociceptive pain regulation. Preferably the subject is a human.

Such antibodies may be administered alone or contained in a pharmaceutical composition comprising antibodies against a nociception-related polypeptide and other reagents effective as modulators of nociceptive pain and associated pain disorders both in vitro and in vivo.

The term "epitope", as used herein, refers to an antigenic determinant on an antigen, such as a nociception-related polypeptide, to which the paratope of an antibody, such as an antibody that binds to a nociception-related polypeptide of the invention. Antigenic determinants usually consist of chemically active surface groupings of molecules, such as amino acids or sugar side chains, and can have specific three-dimensional structural characteristics, as well as specific charge characteristics.

Antibodies which bind to a polypeptide of the invention can be prepared using an intact polypeptide or fragments containing small peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, Current Protocols in Immunology, Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

Antibodies of the invention include polyclonal antibodies, monoclonal antibodies, and fragments of polyclonal and monoclonal antibodies.

The preparation of polyclonal antibodies is well-known to those skilled in the art. See, for example, Green et al., Production of Polyclonal Antisera, in Immunochemical Protocols (Manson, ed.), pages 1–5 (Humana Press 1992); Coligan et al., Production of Polyclonal Antisera in Rabbits, Rats, Mice and Hamsters, in Current Protocols in Immunology, section 2.4.1 (1992), which are hereby incorporated by reference.

The preparation of monoclonal antibodies likewise is conventional. See, for example, Kohler & Milstein, Nature, 256:495 (1975); Coligan et al., sections 2.5.1–2.6.7; and Harlow et al., Antibodies: A Laboratory Manual, page 726 (Cold Spring Harbor Pub. 1988), which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1–2.7.12 and sections 2.9.1–2.9.3; Barnes et al., Purification of Immunoglobulin G (IgG), in Methods in Molecular Biology, Vol. 10, pages 79–104 (Humana Press 1992). Methods of in vitro and in vivo multiplication of monoclonal antibodies is well-known to those skilled in the art. Multiplication in vitro may be carried out in suitable culture media such as Dulbecco's Modified Eagle Medium or RPMI 1640 medium, optionally replenished by a mammalian serum such as fetal calf serum or trace elements and growth-sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., osyngeneic mice, to cause growth of antibody-producing tumors. Optionally, the animals are primed with a hydrocarbon, especially oils such as pristane tetramethylpentadecane prior to injection. After one to three weeks, the desired monoclonal antibody is recovered from the body fluid of the animal.

Therapeutic applications for antibodies disclosed herein are also part of the present invention. For example, antibodies of the present invention may also be derived from subhuman primate antibody. General techniques for raising therapeutically useful antibodies in baboons can be found, for example, in Goldenberg et al, International Patent Publication WO 91/11465 (1991) and Losman et al., Int. J. Cancer, 46:310 (1990), which are hereby incorporated by reference.

Alternatively, an anti-nociception-related polypeptide antibody may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., Proc. Nat'l Acad. Sci. USA, 86:3833 (1989), which is hereby incorporated in its entirety by reference. Techniques for producing humanized monoclonal antibodies are described, for example, by Jones et al., Nature, 321:522 (1986); Riechmann et al., Nature, 332:323 (1988); Verhoeyen et al., Science, 239:1534 (1988); Carter et al., Proc. Nat'l Acad. Sci. USA, 89:4285 (1992); Sandhu, Crit. Rev. Biotech., 12:437 (1992); and Singer et al., J. Immunol., 150:2844 (1993), which are hereby incorporated by reference.

Antibodies of the invention also may be derived from human antibody fragments isolated from a combinatorial immunoglobulin library. See, for example, Barbas et al., Methods: A Companion to Methods in Enzymology, Vol. 2, page 119 (1991); Winter et al., Ann. Rev. Immunol. 12:433 (1994), which are hereby incorporated by reference. Cloning and expression vectors that are useful for producing a human immunoglobulin phage library can be obtained, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet., 7:13 (1994); Lonberg et al., Nature, 368:856 (1994); and Taylor et al., Int. Immunol., 6:579 (1994), which are hereby incorporated by reference.

Antibody fragments of the invention can be prepared by proteolytic hydrolysis of the antibody or by expression in $E$ $coli$ of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg in U.S. Pat. No. 4,036,945 and No. 4,331,647, and references contained therein. These patents are hereby incorporated in their entireties by reference. See also Nisonhoff et al., Arch. Biochem. Biophys,. 89:230 (1960); Porter, Biochem. J., 73:119 (1959); Edelman et al., Methods in Enzymology, Vol. 1, page 422 (Academic Press 1967); and Coligan et al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent, as described in Inbar et al., Proc. Nat'l Acad. Sci. USA, 69:2659 (1972). Alternatively, the variable chains can be linked by an intermolecular disulfide bond or cross-linked by chemicals such as glutaraldehyde. See, e.g., Sandhu, supra. Preferably, the $F_v$ fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as $E. Coli$. The recombinant host cells synthesize a single polypeptide chain with a linker peptide bridging the two V domains. Methods for producing sFvs are described, for example, by Whitlow et al., Methods: A Companion to Methods in Enzymology, Vol. 2, page 97 (1991); Bird et al., Science, 242:423 (1988); Ladner et al., U.S. Pat. No. 4,946,778; Pack et al., Bio/Technology, 11:1271 (1993); and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., Methods: A Companion to Methods in Enzymology, Vol. 2, page 106 (1991).

In one embodiment, the invention provides a method for modulating (e.g., inhibiting) nociceptive pain in a subject by administering to a cell or subject an effective amount of a composition which contains a nociception-related polypeptide, or biologically functional fragment thereof or an agent (e.g, an antibody, ribozyme, antisense molecule, or double-stranded interfering RNA molecules) that interacts with or inhibits expression of a nociception-related polypeptide of the invention.

As used herein, an "effective amount" of a composition containing nociception-related polypeptide or a nociception-related polypeptide-modulating agent is defined as that amount that is effective in modulating nociceptive pain or a nociceptive reflex in a subject. For example, an inhibitory-effective amount would be that amount of the composition or agent sufficient to inhibit a nociceptive pain reflex. One skilled in the art can easily identify agents that modulate as well as the effective amount of an agent that modulates nociceptive reflex by using, for example, the $Drosophila$ reflex discussed below. Briefly, a determination can be made as to the effectiveness or effective concentration of an agent by contacting a $Drosophila$ larvae with the test agent or concentration and then exposing the larvae to a noxious agent (e.g., heat) and determining the larvae's reflex (e.g., roll over reflex) in the presence and absence of the agent.

In another embodiment, the present invention provides a method for modulating expression of a nociception-related polypeptide as well as methods for screening for agents which modulate nociception-related polypeptide gene expression. In this embodiment, a cell or subject is contacted with an agent suspected or known to have nociception-related polypeptide expression modulating activity. The change in nociception-related polypeptide gene expression is then measured as compared to a control or standard sample. The control or standard sample can be the baseline expression of the cell or subject prior to contact with the agent. An agent which modulates nociception-related polypeptide gene expression may be a polynucleotide, for example, the polynucleotide may be an antisense, a triplex agent, a ribozyme, or a double-stranded interfering RNA. For example, an antisense molecule may be directed to the structural gene region or to the promoter region of nociception-related polypeptide gene. The agent may be an agonist, antagonist, peptide, peptidomimetic, antibody, or chemical.

Double-stranded interfering RNA molecules are especially useful to inhibit expression of a target gene. For example, double-stranded RNA molecules can be injected into a target cell or organism to inhibit expression of a gene and the resultant gene products activity. It has been found that such double-stranded RNA molecules are more effective at inhibiting expression than either RNA strand alone. (Fire et al., Nature, 1998, 19:391(6669):806–11).

When a disorder is associated with abnormal expression of a nociception-related polypeptide (e.g., overexpression, or expression of a mutated form of the protein), a therapeutic approach which directly interferes with the translation of a nociception-related polypeptide is possible. Alternatively, similar methodology may be used to study gene activity. For example, antisense nucleic acid, double-stranded interfering RNA or ribozymes could be used to bind to the a nociception-related polypeptide mRNA sequence or to cleave it. Antisense RNA or DNA molecules bind specifically with a targeted gene's RNA message, interrupting the expression of that gene's protein product. The antisense binds to the messenger RNA forming a double stranded molecule which cannot be translated by the cell. Antisense oligonucleotides of about 15–25 nucleotides are preferred since they are easily synthesized and have an inhibitory effect just like antisense RNA molecules. In addition, chemically reactive groups, such as iron-linked ethylenediaminetetraacetic acid (EDTA-Fe) can be attached to an antisense oligonucleotide, causing cleavage of the RNA at the site of hybridization. Antisense nucleic acids are DNA or RNA molecules that are complementary to at least a portion of a specific mRNA molecule (Weintraub, Scientific American, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target nociception-related polypeptide producing cell. The use of antisense methods to inhibit the in vitro translation of genes is well known in the art (Marcus-Sakura, Anal. Biochem., 172:289, 1988).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., Antisense Res. and Dev., 1:227, 1991; Helene, Anticancer Drug Design, 6:569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, J. Amer. Med. Assn., 260:3030, 1988). A major advantage of this approach is that, because they are sequence-specific, only mRNAs with particular sequences are inactivated.

There are two basic types of ribozymes namely, tetrahymena-type (Hasselhoff, Nature, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-base recognition sequences are preferable to shorter recognition sequences.

These and other uses of antisense and ribozymes methods to inhibit the in vivo translation of genes are known in the art (e.g., De Mesmaeker, et al., Curr. Opin. Struct. Biol., 5:343, 1995; Gewirtz, A. M., el aL, Proc. Natl. Acad. Sci. U.S.A., 93:3161, 1996b; Stein, C. A., Chem. and Biol. 3:319, 1996).

Delivery of antisense, triplex agents, ribozymes, competitive inhibitors, double-stranded interfering RNA and the like can be achieved using a recombinant expression vector such as a chimeric virus or a colloidal dispersion system or by injection. Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuL V), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a polynucleotide sequence of interest into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the antisense polynucleotide.

Another targeted delivery system for polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 μm can encapsulate a substantial percentage of an aqueous buffer containing large macromolecules. RNA, DNA and intact virions can be encapsulated within the aqueous interior and be delivered to cells in a biologically active form (Fraley, et al., Trends Biochem. Sci., 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell K. cytoplasm at high efficiency; and (4) accurate and effective expression of genetic information (Mannino, et al., Biotechniques, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidyl-glycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. In general, the compounds bound to the surface of the targeted delivery system will be ligands and receptors which will allow the targeted delivery system to find and "home in" on the desired cells. A ligand may be any compound of interest which will bind to another compound, such as a receptor.

The agents useful in the method of the invention can be administered, for in vivo application, parenterally by injection or by gradual perfusion over time. Administration may be intravenously, intraperitoneally, intramuscularly, subcutaneously, intracavity, or transdermally. For in vitro studies the agents may be added or dissolved in an appropriate biologically acceptable buffer and added to a cell or tissue.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents and inert gases and the like.

It is envisioned that the invention can be used to treat pathologies associated with hyperalgesia and nociceptive pain associated disorders. Therefore, the present invention encompasses methods for ameliorating a disorder associated with nociception, including treating a subject having the disorder, at the site of the disorder, with an agent which modulates a nociception-related polypeptide. Generally, the terms "treating", "treatment" and the like are used herein to mean affecting a subject, tissue or cell to obtain a desired pharmacologic and/or physiologic effect. The effect may be prophylactic in terms of completely or partially preventing a disease or sign or symptom thereof, and/or may be therapeutic in terms of a partial or complete cure for an infection or disease and/or adverse effect attributable to the infection or disease. "Treating" as used herein covers any treatment of, or prevention of, an infection or disease in an invertebrate, a vertebrate, a mammal, particularly a human, and includes: (a) preventing the disorder from occurring in a subject that may be predisposed to the disorder, but has not yet been diagnosed as having it; (b) inhibiting the disorder, i.e., arresting its development; or (c) relieving or ameliorating the disorder, i.e., cause regression of the disorder.

The invention includes various pharmaceutical compositions useful for ameliorating symptoms attributable to a nociceptive pain-associated disorder. The pharmaceutical compositions according to the invention are prepared by bringing an antibody against nociception-related polypeptide, a polypeptide or peptide derivative of a nociception-related polypeptide, a nociception-related polypeptide mimetic, a drug, chemical or combination of chemicals or a nociception-related polypeptide-modulating agent into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co., 1405–1412, 1461–1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed.).

The pharmaceutical compositions are preferably prepared and administered in dose units. Solid dose units are tablets, capsules and suppositories. For treatment of a subject, depending on activity of the compound, manner of administration, nature and severity of the disorder, age and body weight of the subject, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention may be administered locally or systemically in a therapeutically effective dose. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of particular disorders. Various considerations are described, e.g., in Langer, Science, 249:1527, (1990); Gilman et al. (eds.) (1990), each of which is herein incorporated by reference.

In one embodiment, the invention provides a pharmaceutical composition useful for administering a nociception-related polypeptide, or nucleic acid encoding a nociception-related polypeptide, to a subject in need of such treatment. "Administering" the pharmaceutical composition of the present invention may be accomplished by any means known to the skilled artisan. Preferably a "subject" refers to a mammal, most preferably a human, but may be any organism.

A nociception-related polypeptide or antibody can be administered parenterally, enterically, by injection, rapid infusion, nasopharyngeal absorption, dermal absorption, rectally and orally. Pharmaceutically acceptable carrier preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers for occlusive dressings can be used to increase skin permeability and enhance antigen absorption. Liquid dosage forms for oral administration may generally comprise a liposome solution containing the liquid dosage form. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners and elixirs containing inert diluents commonly used in the art, such as purified water.

In another embodiment, the invention provides a method for identifying a agent which modulates nociception-related polypeptide expression or activity including incubating components comprising the agent and a nociception-related polypeptide, or a recombinant cell expressing a nociception-related polypeptide, under conditions sufficient to allow the agent to interact and determining the affect of the agent on the expression or activity of the gene or polypeptide, respectively. The term "affect", as used herein, encompasses any means by which gene expression or protein activity can be modulated. Such agents can include, for example, polypeptides, peptidomimetics, chemical compounds, small molecules and biologic agents as described below.

Incubating includes conditions which allow contact between the test agent and a nociception-related polypeptide, a cell expressing a nociception-related polypeptide or nucleic acid encoding a nociception-related polypeptide. Contacting includes in solution and in solid phase. The test agent may optionally be a combinatorial library for screening a plurality of agents. Agents identified in the method of the invention can be further evaluated, detected, cloned, sequenced, and the like, either in solution or after binding to a solid support, by any method usually applied to the detection of a specific DNA sequence such as PCR, oligomer restriction (Saiki, et al., Bio/Technology, 3:1008–1012, 1985), oligonucleotide ligation assays (OLAs) (Landegren, et al., Science, 241:1077, 1988), and the like. Molecular techniques for DNA analysis have been reviewed (Landegren, et al., Science, 242:229–237, 1988).

Thus, the method of the invention includes combinatorial chemistry methods for identifying chemical agents that bind to or affect nociception-related polypeptide expression or activity.

Areas of investigation are the development of therapeutic treatments. The screening identifies agents that provide modulation of nociception-related polypeptide function in targeted organisms. Of particular interest are screening assays for agents that have a low toxicity or a reduced number of side effects for humans.

The term "agent" as used herein describes any molecule, e.g. protein or pharmaceutical, with the capability of altering or mimicking the physiological function or expression of a nociception-related polypeptide. Generally, a plurality of assay mixtures are run in parallel with different agent concentrations to obtain a differential response to the various concentrations. Typically, one of these concentrations serves as a negative control, i.e. at zero concentration or below the level of detection.

As used herein, an agent that acts, directly or indirectly via a receptor or receptors responsible for mediating or involved in peripheral hyperalgesia, by antagonizing the activity of hyperalgesia mediating agents, such as a prostaglandin, is an agent intended for use herein, if it also does not exhibit CNS effects as defined herein. Such agent is a peripheral antihyperalgesic. The activity of antihyperalgesic agents is distinct from the activity of centrally-acting analgesic agents (e.g., agents that act by virtue of crossing the blood brain barrier). Anti-hyperalgesic agents act to block hypersensitivity. The compositions and methods of the invention are intended for prevention and/or the amelioration of the symptoms of hyperalgesia by decreasing or eliminating the hyperalgesia or by preventing its onset. An antihyperalgesic agent is distinct from a local anesthetic, which is an agent that produces numbness by abolishing sensitivity to touch and other stimuli, including pain stimuli. Local anesthetics abolish sensation, including pain, by blocking conduction in nerve axons in the peripheral nervous system. Antihyperalgesics, on the other hand, alleviate pain by elevating a patient's threshold to pain. Thus, unlike anesthetics, antihyperalgesics reduce sensation to pain during states of increased sensitivity (e.g., hyperalgesia) without substantially affecting normal sensitivity to touch and/or other stimuli.

Antihyperalgesics are agents that may reduce hypersensitivity to touch and other stimuli that would not, under normal circumstances, evoke a pain response. The hyperalgesic response is an exaggerated response, such as excessive sensitiveness or sensibility to pain from touch, slight exertion, warmth and the like. Antihyperalgesics may be identified, for example, by the Randall-Selitto method (see, e.g., Randall et al. Arch. Int. Pharmacodyn. 111:409–419, 1957), as well as the formalin, carrageenan and yeast induced inflammation methods. In addition to the antihyperalgesic effect, the antihyperalgesic agents provided herein may concurrently provide an analgesic effect.

Analgesics are agents that may reduce a patient's perception of pain evoked by stimuli that are acutely painful under normal circumstances. Thus, analgesics may be effective in reducing the acute and immediate pain associated with trauma (e.g., pinpricks, burns, or crushing wounds) as well as chronic pain, that is not normally associated with peripheral sensitization, such as cancer or headache pain.

In addition, cells or organisms which have a mutation in a nociception-related polypeptide sequence may be used as models to screen for agents which modulate disorders associated with the mutation. For example, the inventors have identified organisms (e.g., *Drosophila*) which lack normal nociceptive reflex activity. Accordingly, administration of agents to organism having such a mutation, or cells derived or recombinantly modified to have a reduced nociceptive activity may be used to determine the effect of the drug or agent on nociception.

In a further embodiment, the invention provides a method of detecting nociception-related polypeptide or polynucleotide or diagnosing a nociceptive-associated disorder in a subject including contacting a cell component containing nociception-related polypeptide or polynucleotide with a reagent which binds to the cell polypeptide or polynucleotide (herein after cell component). The cell component can be or contain a nucleic acid, such as DNA or RNA, or a protein. When the component is nucleic acid, the reagent is a nucleic acid probe or PCR primer. When the cell component is protein, the reagent is an antibody probe. The probes are detectably labeled, for example, with a radioisotope, a fluorescent compound, a bioluminescent compound, a chemiluminescent compound, a metal chelator or an enzyme. Those of ordinary skill in the art will know of other labels suitable for binding to an antibody or nucleic acid probe, or will be able to ascertain such, using routine experimentation. There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds. In addition, the antibodies, polypeptides and polynucleotide sequences of the invention can be used to diagnosis a nociceptive disorder.

A monoclonal antibody of the invention, directed toward nociception-related polypeptide is useful for the in vivo and in vitro detection of antigen. The detectably labeled monoclonal antibody is given in a dose that is diagnostically effective. The term "diagnostically effective" means that the amount of detectably labeled monoclonal antibody is administered in sufficient quantity to enable detection of nociception-related polypeptide antigen for which the monoclonal antibodies are specific.

The concentration of a detectably labeled monoclonal antibody administered to a subject should be sufficient such that the binding to those cells, body fluid, or tissue having nociception-related polypeptide that is detectable compared to the background. Further, it is desirable that the detectably labeled monoclonal antibody be rapidly cleared from the circulatory system in order to give the best target-to-background signal ratio.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is the half-life of the radioisotope which should be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 key range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (1R1) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

In another embodiment, nucleic acid probes can be used to identify a polynucleotide encoding a nociception-related polypeptide from a specimen obtained from a subject. Examples of specimens from which nucleic acid sequence encoding a nociception-related polypeptide can be derived include insect, human, swine, porcine, feline, canine, equine, murine, cervine, caprine, lupine, leporidine and bovine species.

Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., Nucl. Acid Res. 9:879, 1981).

In an embodiment of the invention, purified nucleic acid fragments containing intervening sequences or oligonucleotide sequences of 10–50 base pairs are radioactively labeled. The labeled preparations are used to probe nucleic acids from a specimen by the Southern hybridization technique. Nucleotide fragments from a specimen, before or after amplification, are separated into fragments of different molecular masses by gel electrophoresis and transferred to filters that bind nucleic acid. After exposure to the labeled probe, which will hybridize to nucleotide fragments containing target nucleic acid sequences, binding of the radioactive probe to target nucleic acid fragments is identified by autoradiography (see Genetic Engineering, 1, ed. Robert Williamson, Academic Press, (1981), 72–81). Alternatively, nucleic acid from the specimen can be bound directly to filters to which the radioactive probe selectively attaches by binding nucleic acids having the sequence of interest. Specific sequences and the degree of binding is quantitated by directly counting the radioactive emissions.

Where the target nucleic acid is not amplified, detection using an appropriate hybridization probe may be performed directly on the separated nucleic acid. In those instances where the target nucleic acid is amplified, detection with the appropriate hybridization probe would be performed after amplification.

For the most part, the probe will be detectably labeled with an atom or inorganic radical, most commonly using radionuclides, but also heavy metals can be used. Conveniently, a radioactive label may be employed. Radioactive labels include $^{32}P$, $^{125}I$, $^{3}H$, $^{14}C$, $^{111}In$, $^{99}Tc$, or the like. Any radioactive label may be employed which provides for an adequate signal and has sufficient half-life. Other labels include ligands, which can serve as a specific binding pair member for a labeled ligand, and the like. A wide variety of labels routinely employed in immunoassays can readily be employed in the present assay. The choice of the label will be governed by the effect of the label on the rate of hybridization and binding of the probe to mutant nucleotide sequence. It will be necessary that the label provide sufficient sensitivity to detect the amount of mutant nucleotide sequence available for hybridization.

The manner in which the label is bound to the probe will vary depending upon the nature of the label. For a radioactive label, a wide variety of techniques can be employed. Commonly employed is nick translation with an a $^{32}P$-dNTP or terminal phosphate hydrolysis with alkaline phosphatase followed by labeling with radioactive $^{32}P$ employing $^{32}P$-NTP and T4 polynucleotide kinase. Alternatively, nucleotides can be synthesized where one or more of the elements present are replaced with a radioactive isotope, e.g, hydrogen with tritium. If desired, complementary labeled strands can be used as probes to enhance the concentration of hybridized label.

Where other radionucleotide labels are involved, various linking groups can be employed. A terminal hydroxyl can be esterified, with inorganic acids, e.g., $^{32}P$ phosphate, or $^{14}C$ organic acids, or else esterified to provide linking groups to the label. Alternatively, intermediate bases may be substituted with activatable linking groups that can then be linked to a label.

Enzymes of interest as reporter groups will primarily be hydrolases, particularly esterases and glycosidases, or oxidoreductases, particularly peroxidases. Fluorescent compounds include fluorescein and its derivatives, rhodamine and its derivatives, dansyl, umbelliferone, and so forth. Chemiluminescers include luciferin, and 2, 3-dihydrophthalazinediones (e.g., luminol).

Standard hybridization techniques for detecting a nucleic acid sequence are known in the art. The particular hybridization technique is not essential to the invention. Other hybridization techniques are described by Gall and Pardue, Proc. Natl. Acad. Sci. 63:378, 1969); and John, et al., Nature, 223.:582, 1969). As improvements are made in hybridization techniques they can readily be applied in the method of the invention.

The amount of labeled probe present in the hybridization solution will vary widely, depending upon the nature of the label, the amount of the labeled probe that can reasonably bind to the filter, and the stringency of the hybridization. Generally, substantial excess over stoichiometric concentrations of the probe will be employed to enhance the rate of binding of the probe to the fixed target nucleic acid.

The present invention also contemplates transgenic non-human organisms, including invertebrates, vertebrates and mammals. For purposes of the subject invention, these animals are referred to as "ransgenic" when such animal has had a heterologous DNA sequence, or one or more additional DNA sequences normally endogenous to the animal (collectively referred to herein as "transgenes") chromosomally integrated into the germ cells of the animal. The transgenic animal (including its progeny) will also have the transgene integrated into the chromosomes of somatic cells.

Various methods to make the transgenic animals of the subject invention can be employed. Generally speaking, three such methods may be employed. In one such method, an embryo at the pronuclear stage (a "one cell embryo") is harvested from a female and the transgene is microinjected into the embryo, in which case the transgene will be chromosomally integrated into both the germ cells and somatic cells of the resulting mature animal. In another such method, embryonic stem cells are isolated and the transgene incorporated therein by electroporation, plasmid transfection or microinjection, followed by reintroduction of the stem cells into the embryo where they colonize and contribute to the germ line. Methods for microinjection of mammalian species is described in U.S. Pat. No. 4,873,191. In yet another such method, embryonic cells are infected with a retrovirus containing the transgene whereby the germ cells of the embryo have the transgene chromosomally integrated therein. When the animals to be made transgenic are avian, because avian fertilized ova generally go through cell division for the first twenty hours in the oviduct, microinjection into the pronucleus of the fertilized egg is problematic due to the inaccessibility of the pronucleus. Therefore, of the methods to make transgenic animals described generally above, retrovirus infection is preferred for avian species, for example as described in U.S. Pat. No. 5,162,215. If microinjection is to be used with avian species, however, a published procedure by Love et al., (Biotechnology, 12, January 1994) can be utilized whereby the embryo is obtained from a sacrificed hen approximately two and one-half hours after the laying of the previous laid egg, the transgene is microinjected into the cytoplasm of the germinal disc and the embryo is cultured in a host shell until maturity. When the animals to be made transgenic are bovine or porcine, microinjection can be hampered by the opacity of the ova thereby making the nuclei difficult to identify by traditional differential interference-contrast microscopy. To overcome this problem, the ova can first be centrifuged to segregate the pronuclei for better visualization.

The "non-human animals" of the invention include, for example, bovine, porcine, ovine and avian animals (e.g., cow, pig, sheep, chicken, turkey). The "transgenic non-human animals" of the invention are produced by introducing "transgenes" into the germline of the non-human animal. Embryonal target cells at various developmental stages can be used to introduce transgenes. Different methods are used depending on the stage of development of the embryonal target cell. The zygote is the best target for micro-injection. The use of zygotes as a target for gene transfer has a major advantage in that in most cases the injected DNA will be incorporated into the host gene before the first cleavage (Brinster et al., Proc. Natl. Acad. Sci. USA 82:4438–4442, 1985). As a consequence, all cells of the transgenic non-human animal will carry the incorporated transgene. This will in general also be reflected in the efficient transmission of the transgene to offspring of the founder since 50% of the germ cells will harbor the transgene.

The term "transgenic" is used to describe an animal which includes exogenous genetic material within all of its cells. A "transgenic" animal can be produced by cross-breeding two chimeric animals which include exogenous genetic material within cells used in reproduction. Twenty-five percent of the resulting offspring will be transgenic i.e., animals which include the exogenous genetic material within all of their cells in both alleles. 50% of the resulting animals will include the exogenous genetic material within one allele and 25% will include no exogenous genetic material.

In the microinjection method useful in the practice of the invention, the transgene is digested and purified free from any vector DNA e.g. by gel electrophoresis. It is preferred that the transgene include an operatively associated promoter which interacts with cellular proteins involved in transcription, ultimately resulting in constitutive expression. Promoters useful in this regard include those from cytomegalovirus (CMV), Moloney leukemia virus (MLV), and herpes virus, as well as those from the genes encoding metallothionin, skeletal actin, P-enolpyruvate carboxylase (PEPCK), phosphoglycerate (PGK), DHFR, and thymidine kinase. Promoters for viral long terminal repeats (LTRs) such as Rous Sarcoma Virus can also be employed. When the animals to be made transgenic are avian, preferred promoters include those for the chicken-globin gene, chicken lysozyme gene, and avian leukosis virus. Constructs useful in plasmid transfection of embryonic stem cells will employ additional regulatory elements well known in the art such as enhancer elements to stimulate transcription, splice acceptors, termination and polyadenylation signals, and ribosome binding sites to permit translation.

Retroviral infection can also be used to introduce transgene into a non-human animal, as described above. The developing non-human embryo can be cultured in vitro to the blastocyst stage. During this time, the blastomeres can be targets for retro viral infection (Jaenich, R., Proc. Natl. Acad. Sci USA 73:1260–1264, 1976). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retro virus carrying the transgene (Jahner, et al., Proc. Natl. Acad. Sci. USA 82:6927–6931, 1985; Van der Putten, et al., Proc. Natl. Acad. Sci USA 82:6148–6152, 1985). Transfection is easily and efficiently obtained by culturing the blastomeres on a monolayer of virus-producing cells (Van der Putten, supra; Stewart, et al., EMBO J. 6:383–388, 1987). Alternatively, infection can be performed at a later stage. Virus or virus-producing cells can be injected into the blastocoele (D. Jahner et al., Nature 298:623–628, 1982). Most of the founders will be mosaic for the transgene since incorporation occurs only in a subset of the cells which formed the transgenic nonhuman animal. Further, the founder may contain various retro viral insertions of the transgene at different positions in the genome which generally will segregate in the offspring. In addition, it is also possible to introduce transgenes into the germ line, albeit with low efficiency, by intrauterine retroviral infection of the midgestation embryo (D. Jahner et al., supra).

A third type of target cell for transgene introduction is the embryonal stem cell (ES). ES cells are obtained from pre-implantation embryos cultured in vitro and fused with embryos (M. J. Evans et al. Nature 292:154–156, 1981; M. O. Bradley et al., Nature 309:255–258, 1984; Gossler, et al., Proc. Natl. Acad. Sci USA 83:9065–9069, 1986; and Robertson et al., Nature 322:445–448, 1986). Transgenes can be efficiently introduced into the ES cells by DNA transfection or by retro virus-mediated transduction. Such transformed ES cells can thereafter be combined with blastocysts from a nonhuman animal. The ES cells thereafter colonize the embryo and contribute to the germ line of the resulting chimeric animal. (For review see Jaenisch, R., Science 240:1468–1474, 1988).

"Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

"Transgene" means any piece of DNA which is inserted by artifice into a cell, and becomes part of the genome of the organism (i.e., either stably integrated or as a stable extra-chromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence which is transcribed into DNA and then incorporated into the genome. The transgenes of the invention include DNA sequences which encode a nociception-related polypeptide, and include sense, antisense, dominant negative encoding polynucleotides, which may be expressed in a transgenic non-human animal. The term "transgenic" as used herein additionally includes any organism whose genome has been altered by in vitro manipulation of the early embryo or fertilized egg or by any transgenic technology to induce a specific gene knockout (i.e., knockout of a nociception-related polypeptide). The term "gene knockout" as used herein, refers to the targeted disruption of a gene in vivo with complete or partial loss of function that has been achieved by any transgenic technology familiar to those in the art (e.g., insertion of a P-element in Drosophila). In one embodiment, transgenic animals having gene knockouts are those in which the target gene has been rendered nonfunctional by an insertion targeted to the gene to be rendered non-functional by homologous recombination. As used herein, the term "transgenic" includes any transgenic technology familiar to those in the art which can produce an organism carrying an introduced transgene or one in which an endogenous gene has been rendered non-functional or "knocked out."

In one embodiment, the transgene comprises DNA antisense to the coding sequence for a nociception-related polypeptide. In another embodiment, the transgene comprises DNA encoding an antibody which is able to bind to a nociception-related polypeptide. Where appropriate, DNA sequences that encode proteins having nociceptive activity but differ in nucleic acid sequence due to the degeneracy of the genetic code may also be used herein, as may truncated forms, allelic variants and interspecies homologues.

The invention also includes animals having heterozygous mutations in or partial inhibition of function or expression of a nociception-related polypeptide. One of skill in the art would readily be able to determine if a particular mutation or if an antisense molecule was able to partially inhibit nociception-related polypeptide. For example, in vitro testing may be desirable initially by comparison with wild-type (e.g., comparison of northern blots to examine a decrease in expression).

After an embryo has been microinjected, colonized with transfected embryonic stem cells or infected with a retrovirus containing the transgene (except for practice of the subject invention in avian species which is addressed elsewhere herein) the embryo is implanted into the oviduct of a pseudopregnant female. The consequent progeny are tested for incorporation of the transgene by Southern blot analysis of blood samples using transgene specific probes. PCR is particularly useful in this regard. Positive progeny ($G_0$) are crossbred to produce offspring ($G_1$) which are analyzed for transgene expression by Northern blot analysis of tissue samples. To be able to distinguish expression of like-species transgenes from expression of the animals endogenous nociception-related polypeptide gene(s), a marker gene fragment can be included in the construct in the 3' untranslated region of the transgene and the Northern probe designed to probe for the marker gene fragment. The serum levels of nociception-related polypeptide can also be measured in the transgenic animal to establish appropriate expression. Expression of the nociceptive-related transgenes, thereby decreasing the nociception-related polypeptide in the tissue and serum levels of the transgenic animals.

Transgenic organisms of the invention are highly useful in the production of organisms for study of tumorgenesis and in identifying agents or drugs with inhibit or modulate tumorgenesis and inheritance.

It will be recognized that the method of creating a transgenic organism include methods of inserting a transgene into, for example, an embryo of an already created transgenic organism, the organism being transgenic for a different unrelated gene or gene product.

In one embodiment the transgenic organism is an insect. An insect as used herein denotes all insect species. Typically the insect is selected from the group consisting of bristletails, springtails, mayflies, dragonflies, damselflies, grasshoppers, crickets, walkingstickes, praying-mantises, cockroaches, earwigs, termites, stoneflies, lice, thrips, bed bugs, plant bugs, damsel bugs, flower bugs, assassin bugs, ambush bugs, lace bugs, stink bugs, cicadas, treehoppers, leafhoppers, spittlebugs, planthoppers, aphids, whiteflies, beetles, scropionflies, caddisflies, moths, skippers, butterlies, crane flies, sand flies, mosquitoes, horse flies, fruit flies louse flies, bees, wasps, and ants.

The transgenic insects of the invention can be produced by introducing into single cell embryos DNA disrupting expression of a nucleic acid encoding the wild type nociception-related polypeptide sequence. Transgenic insects can be generated by microinjection, which can produce P-element mediated germ line transformation. For transgenic insects, generally the transgene is introduced at an embryonic stage. For example, transgenic insects of the present invention can be produced by introducing into single cell embryos invention polynucleotides, either naked or contained in an appropriate vector, by microinjection, for example, which can produce insects by P-element mediated germ line transformation (see e.g., Rubin et al., Science 218:348–353 (1982)). Totipotent or pluripotent stem cells transformed by microinjection, calcium phosphate mediated precipitation, liposome fusion, retroviral infection or other means are then introduced into the embryo, and the polynucleotides are stably integrated into the genome. A transgenic embryo so transformed then develops into a mature transgenic insect in which the transgene is inherited in normal Mendelian fashion. Additional methods for producing transgenic insects can be found, for example, in O'Brochta et al., *Insect Biochem. Mol. Biol.* 26:739–753 (1996) and in Louleris et al., *Science* 270:2002–2005 (1995).

In a one method, developing insect embryos are infected with a virus, such as a baculovirus (e.g., *Autographa californica* AcNPV), containing a polynucleotide sequence of the invention, and transgenic insects produced from the infected embryo. The virus can be an occluded virus or a nonoccluded virus. A virus can be occluded by coinfection of cells with a helper virus which supplies polyhedrin gene function. The skilled artisan will understand how to construct recombinant viruses in which the polynucleotide is inserted into a nonessential region of the baculovirus genome. For example, in the AcNPV genome, nonessential regions include the p10 region (Adan et al., *Virology* 444:782–793, 1982), the DA26 region (O'Reily et al., *J. Gen. Virol.* 71:1029–1037, 1990), the ETL region (Crawford et al., *Virology* 62:2773–2781, 1988), the egt region (O'Reily et al., *J. Gen. Virol.* 64:1321–1328), amongst others. Significant homology exists among particular genes of different baculoviruses and therefore, one of skill in the art will understand how to insert an invention polynucleotide into similar nonessential regions of other baculoviruses. Thus, for example, a sequence encoding a nociception-related polypeptide as described herein may be placed under control of an AcNPV promoter (e.g., the polyhedrin promoter). Depending on the vector utilized, any of a number of suitable transcription and translation elements, including constitutive, inducible and conditional promoters, enhancers, transcription terminators, etc. may be used in order to transcribe invention polynucleotides or express invention polypeptides. Alternatively, a transgene containing a nucleic acid sequence disrupting expression of a nociception-related polypeptide may not contain a promoter as the nucleic acid sequence need not be transcribed or translated to obtain a transgenic insect having disrupted nociception-related polypeptide.

Thus, the invention provides methods for producing transgenic insects having a disrupted nucleic acid sequence encoding a nociception-related polypeptide. The methods include introducing into the genome of an insect a nucleic acid construct, including a disrupted or mutated nociception-related polynucleotide sequence, and obtaining a transgenic insect having a disrupted nucleic acid sequence encoding nociception-related polypeptide. The invention further provides methods for producing transgenic insects having a nucleic acid encoding nociception-related polypeptide or functional fragment thereof.

Without further elaboration, it is believed that one skilled in the art can, using the preceding description, utilize the present invention to its fullest extent. The following examples are to be considered illustrative and thus are not limiting of the remainder of the disclosure in any way whatsoever.

EXAMPLE 1

Forward Genetic Analysis Of Nociception

To identify genes important for nociception, a genetic screen for mutations that cause sensitivity to noxious heat was performed. A collection of fly lines that carry P-elements randomly inserted within the genome (Rorth et al (1998) Development 125, 1049–57) was screened. The advantage of screening this particular collection of P-element insertions is that most of the lines have had their insertion site precisely determined by the Berkeley *Drosophila* Genome Project (BDGP). In addition, the P-elements used to generate these lines, called EP elements, contain gal4 binding upstream activation sequences (UAS) on their 3' end. Thus, EP elements inserted in the proper orientation can be used to drive tissue-specific expression of the gene downstream of the insertion site when the cell line containing the identified P-element is crossed to a gal4 driver expressing line (Rorth, et al., 1998, supra).

Third instar larvae homozygous for insertions on the second chromosome or third chromosome were examined. Larvae were from vials seeded for seven days at room temperature. To remove the larvae from the vials as gently as possible, water was added to soften the food, and the larvae and food were poured into 35 mm diameter petri dishes. A noxious heat probe was set to maintain a temperature in the range of 42–46° C. as measured by a fine thermocouple, and the stimulus was delivered by gently touching the homozygous mutant larvae laterally in abdominal segments five, six or seven. At this temperature, wild type larvae performed the rolling avoidance behavior within less than one second from the initiation of contact (average response time, 0.4 sec±0.06 sec). This temperature does not result in melanization at the site of stimulation implying little tissue damage. Upon removal of the probe, the response ceases immediately, but can be evoked by repeat stimulation. Adult viability of the stimulated larvae is unimpaired. A line was considered to have impaired insensitivity to noxious heat if longer than three seconds of stimulation was required to produce the rolling response.

Approximately 1500 EP lines were screened to identify forty nine lines in which there was a reproducible decrease in sensitivity to noxious heat. A line carrying an insertion on the second chromosome, EP(2)2451, which was among the most insensitive, EP(2)2451, was chosen for further study. Larvae homozygous for EP(2)2451 showed delayed response to noxious heat, some failing to respond even after 10 seconds, at which point the stimulus was withdrawn. To reflect this phenotype, the mutant was named painless[1]. Although painless[1] larvae show a defect in nociception, they still show a normal response to innocuous touch. Indeed, the initial response of a mutant larva to the touch of a noxious heat probe resembles the response of a wild type larva to the touch of an unheated probe, peristaltic locomotor behavior occurs. However, after several seconds of maintained stimulation, rolling may ensue.

EXAMPLE 2

Painless Encodes a Putative Ion Channel

To determine the precise location of the EP(2)2451 insertion, the genomic DNA flanking the EP-element was cloned and sequenced by plasmid rescue. The nucleic acid sequence obtained for the flanking region is the same as the sequence previously determined for this insertion by the Berkeley *Drosophila* Genome Project. The insertion is located 3.6 kilobases upstream of the predicted gene CG15860 (painless) (SEQ ID NO:1; predicted amino acid sequence is the sequence set forth in SEQ ID NO:2 (Accession Number AAF47293; FIG. 5)). Using the predicted amino acid sequence of CG15860 to probe the protein databases with BLAST, the closest protein relatives of known function were found to be ion channels of the transient receptor potential (TRP)/vanilloid receptor family. Consistent with this, the predicted painless protein contains ankryin repeats at its N-terminus and a TRP like ion channel domain near its C-terminus.

Figure 9:
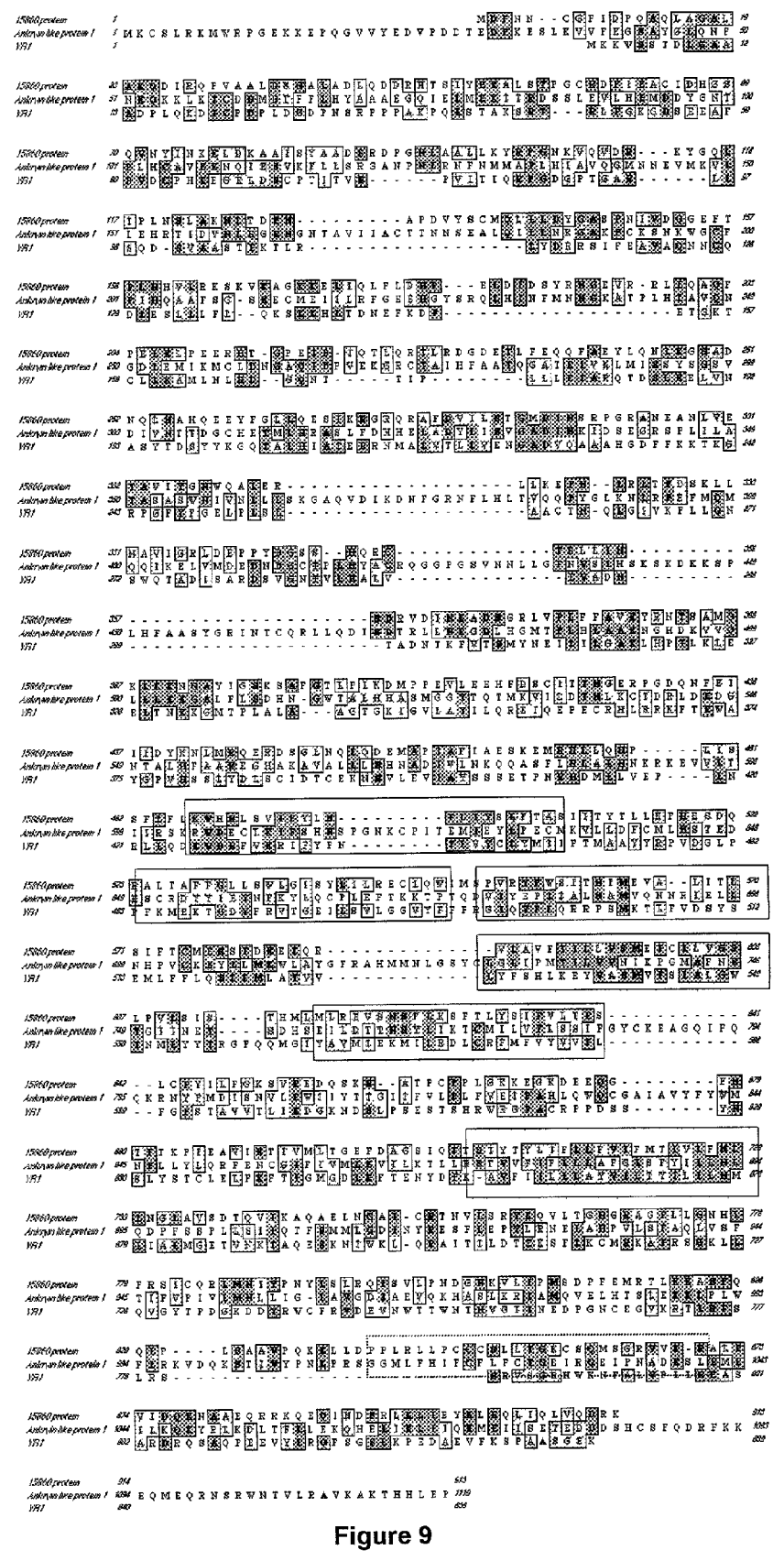

Interestingly, the vanilloid receptor has been demonstrated to be a pain-sensing molecule in vertebrates (Caterina et al. (1997) Nature 389, 816–24) and is essential for sensing a subset of noxious temperatures in a mouse model for nociception (Caterina et al. (2000) Science 288, 306–13) as well as for inflammatory hyperalgesia (Davis et al. (2000) Nature 405, 183–7). However, CG15860 does not encode a fly orthologue of the vanilloid receptor, but instead represents a distinct member of this ion channel family. When the channel region is used for the purpose of comparison, the closest vertebrate homologue found is the human ankryin-like protein (Jaquemar et al. (1999). J Biol Chem 274, 7325–33), which the present study has determined contains a transient receptor potential-like (TRP) channel domain in addition to its ankryin repeats. (See FIG. 9). The painless protein has six putative mtransmembrane regions (indicated by boxed regions in FIG. 9. A putative hydrophobic ligand binding pocket is from about residue 844 to about residue 870 (indicated by a dashed box in FIG. 9). Amino acids that are conserved or conversative variants between proteins are also boxed.

Mammalian homologues of the *Drosophila* TRP channel gene encode a family of at least 20 ion channel proteins. They are widely distributed in mammalian tissues, but their specific physiological functions are largely unknown. A common functional theme that links the TRP channels is their activation or modulation by phosphatidylinositol signal transduction pathways. The channel subunits have six transmembrane domains that most probably assemble into tetramers to form non-selective cationic channels, which allow for the influx of calcium ions into cells. Three subgroups comprise the TRP channel family; the best understood of these mediates responses to painful stimuli. Other proposed functions include repletion of intracellular calcium stores, receptor-mediated excitation and modulation of the cell cycle.

To determine whether or not the insensitivity of painless[1] was due to the presence of the EP-element insertion, painless[1] was crossed to a transposase line to mobilize the EP-element. The progeny of this cross were then crossed to flies mutant for white, and excision alleles of the EP-element were selected based on loss of the white[+] marker present on the insertion. Of 36 excision alleles obtained, 34 were homozygous viable and were tested as larvae for the painless phenotype. Among these, several alleles showed reversion to a normal larval response to noxious heat. On molecular analysis, revertion of the phenotype was found to be correlated with precise excision of the P-element demonstrating that the painless phenotype is associated with the presence of the EP(2)2451 insertion. Additional insensitive mutant alleles of the painless locus were also present among these lines. As expected, excision alleles retained the painless phenotype to varying degree and were found to represent various imprecise excisions of the P-element.

In addition to EP(2)2451, three independent P-element insertions have been within six base pair of EP(2)2451 by BDGP. Larvae homozygous for EP(2)2621 (painless) and EP(2)2251 (painless[3]) were found to be strongly insensitive to noxious heat in the nociception paradigm.

These independent alleles also fail to complement of the nociceptions defect when tested in trans, indicating that the behavioral defects of the lines are due to mutations in the same gene. A fourth insertion, EP(2)2464 (painless[4]), was not tested in the paradigm as few larvae survived to third instar.

Northern analysis was performed on RNA extracted from painless[+] and painless mutant larvae. Total RNA was extracted from first and second instar larvae and 30 μg of total RNA was analyzed by techniques known in the art using an anti-sense riboprobe derived from base pairs 1742 to 2478 of the predicted painless cDNA (CG15860). The antisense riboprobe detects transcripts of 3.0 Kb, 2.0 Kb and 1.0 Kb in painless[+] strains. Using RT-PCR and primers designed across the region, the 3.0 Kb transcript was amplified and its structure was determined. The predicted amino acid sequence of this transcript is identical to that predicted by BDGP for CG15860 (SEQ ID NO:2). However several features of the cDNA's that have been sequenced were not predicted by BDGP. A small untranslated region 3.6 Kb upstream (5') of the CG15860 protein and a 3' untranslated region were identified. The 5' UTR is 63 base pairs in length, 51 of which come from the upstream exon (exon 1) Thus, the 5' UTR is exon 1 (SEQ ID NO:4) and nucleotides 1 to 12 of exon 2 (SEQ ID NO:5). The 3' UTR is 260 base pairs.

All four P-elements disrupt the 5' non-coding exon of the 3.0 Kb transcript. Consistent with this, an increase in size of the 3.0 Kb transcript on a Northern Blot was seen in painless[1] mutant RNA. The size and expression levels of the two smaller painless transcripts were unaffected by the insertion. To determine the structure of the altered transcript produced in painless[1], the 5'end was isolated with RT-PCR, and cloned and sequenced. In the mutant, 510 base pairs of P-element sequence are spliced to the second exon of the painless 3.0 Kb transcript, leaving the wild type start methionine of the protein intact. The additional P-element-derived 5'untranslated region likely interferes with translation of the painless message.

Nucleotide sequences of painless exons are shown in FIG. 11. Additional to the sequence predictd by the Berkeley *Drosophilia* Genome Project are upstream and downstream sequences. The 5' UTR includes the upstream non-coding exon (51 base pairs), and 12 nucleotides from exon 2. Exon 4 includes a poly A tail. The painless genomic sequence has 13482 base pairs. The 3.0 Kb transcript TATA signal is at base pairs 3838 to 3849. The start ATG codon is at 7535. Four exons are identified: exon 1 from base pair 3868 to 3916; exon 2 from base pair 7529 to 7750; exon 3 from base pair 7821 to 9809; and exon 4 from base pair 9883 to 10659.

EXAMPLE 3

Neuronal Circuitry Essential to Nociception

In vertebrates, the cell bodies of nociceptors are located in sensory ganglia, such as the dorsal root ganglia. These cells have projections to the periphery where profuse branching of naked dendrites occurs beneath the skin. In contrast to other sensory modalities (i.e. thermal receptors and touch receptors) which utilize specialized receptor cells to transduce signals, the naked dendrites of nociceptors themselves are thought to contain transducing machinery for noxious stimuli. Similar distinctions prevail in the peripheral nervous system of *Drosophila*. Type I sensory neurons, e.g., chordotolnal neurons and mechanoreceptors, have a single dendrite as part of a specialized sensillum such as a hair (Hartenstein (1988). Development 102, 869–886). Type II or multi-dendritic (md) sensory neurons, do not appear to be associated with a specialized receptor cell but utilize naked dendrites. Others are assoicated with muscles, contain a simple bipolar dendrite (md-bp) and are proposed to function as stretch or proprioceptors. A third class of md neurons send dendrites to trachea (md-td). The group on interest here have dendritic arborizations (md-da) which branch profusely beneath the cuticle (Bodmer, and Jan (1987) Roux's Arch Dev Biol 196, 69–77; Brewster and Bodmer (1995) Development 121, 2923–36).

Since the md-da neurons beneath the cuticle project a plexus of naked dendrites similar to the pain-sensing neurons in mammalian skin, they may include cells that function as *Drosophila* nociceptors. This function was assessed by making use of a cell specific "driver" strain to selectively disrupt the function of md neurons. The tetanus toxin light chain (TeTxLC) blocks calcium dependent evoked synaptic vesicle release through proteolytic cleavage of the v-snare, synaptobrevin (Sweeney et al., (1995) Neuron 14, 341–51). To create larvae expressing TeTxLC in md neurons but not in other cells of the peripheral nervous system the enhancer trap driver strain, gal4 (2)80 was used (md-gal4) (Gao et al. (1999) Genes Dev 13, 2549–61) in which the yeast transcription factor gal4 is expressed in all md-da neurons of the larval peripheral nervous system, along with a small number of cells of the larval CNS, and in oenocytes. When crossed to lines bearing UAS binding sites for gal4 upstream of a gene of interest (Brand and Perrimon (1993) Development 118, 401–15), md-gal4 causes expression of this gene specifically in the above pattern (Gao et al., 1999, supra). In the experiments described herein, md-gal4 was crossed to lines containing either UAS-TeTxLC, or a control line containing UAS-IMPTNT-V, which contains a point mutation that inactivates the catalytic domain of the tetanus toxin protein (Sweeney et al., (1995) supra.

Strikingly, larvae expressing the tetanus toxin light chain in the expression pattern of md-gal4 were unresponsive to noxious heat. Under stimuli where larvae containing the driver alone typically rolled within 0.4 seconds, the majority of md-gal4/UAS-TeTxLC larvae did not respond at all, even after ten seconds of stimulation. Control larvae expressing the tetanus toxin with the mutated catalytic domain or larvae lacking the gal4 driver showed a normal rolling response. Therefore, the neurons and circuitry marked by the md-gal4 enhancer trap include components that are essential to nociception. General motor pathways are not abolished in the md-gal41UAS-TeTxLC larvae, as they responded normally to touch of the anterior segments. Md-da neurons are thus inessential for response to innocuous touch. Consistent with this, the NompA protein, essential for mechanoreception, is expressed specifically in type I sensory neurons and is not detected in type II sensory neurons (Chung et al. (2001). Neuron 29, 415–28). the md-gal4/UAS-TeTxLc larvae did show some behavioral defects. They were somewhat uncoordinated, and would occasionally drag their mouthooks, initiating the peristaltic muscular wave of motion prior to moving their mouthooks forward. Also, while feeding, the larvae sometimes folded into a U-shape, with the head in contact with the posterior, a quirk not seen in normal larvae. In pupae and young adults, md-gal4 is more broadly expressed than in larvae, md-gal4[UAS-TeTxLc thus formed pupae but did not eclose as adult flies.

These observations suggest that the expression of the md-gal4 driver may affect cells other than those involved in nociception.

EXAMPLE 4

A Dominant painless Phenotype

The fact that md-gal4 is able to drive gene expression in cells essential to nociception allows the performance of a separate genetic screen for genes which block nociception when overexpressed. A "gain of function" genetic screen was performed by crossing md-gal4 with the collection of EP lines described above. In theory, gal4 binding to the UAS sites on the EP element should result in increased expression of the gene downstream of the EP element site of insertion, specifically in multi-dendritic neurons. Among approximately 1300 EP lines, fourteen were identified which, when crossed to md-gal4, caused a reproducible and robust decrease in sensitivity to noxious heat. One of them was painless[1].

At first glance, this result might appear to be consistent with a model where excessive painless activity inhibits nociception. However, painless[3] (described herein) also has in insertion in the painless gene which is in the correct orientation and position to drive expression of the 3.0 Kb painless transcript, but did not interfere with nociception when crossed to md-gal4. Since the insertion sites of these two P-elements differ by only sixteen base pairs, this dichotomy was investigated. Using RT-PCR and in situ hybridization, it can be shown that both insertions do show md-gal4 induced transcription from within the EP-element. However, consistent with the insertion sites, the transcript produced from painless[1] is slightly larger than painless[3]. The 5' ends of these RT-PCR products were cloned and sequenced. Both transcripts utilize the same 3' splice donor as in the wild type transcript but differ from each other 5' to the donor site by the expected sixteen base pairs of sequence. This difference dramatically changes the structure of the predicted proteins encoded by the md-gal4 driven transcripts of painless[1] and painless[3].

Figure 4A:
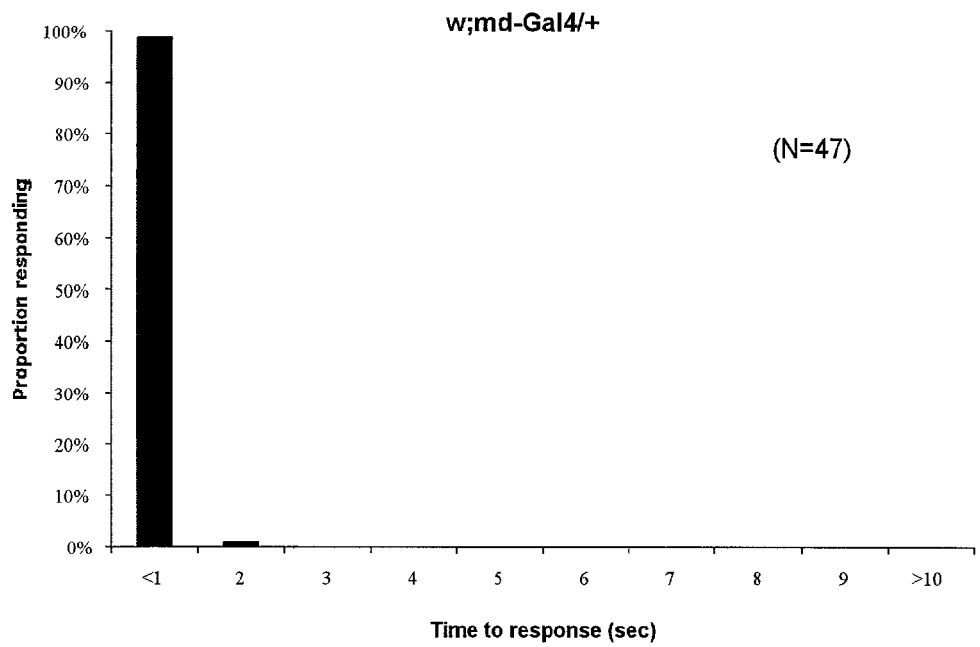
FIG. 4A shows larvae heterozygous for the md-Gal4 driver alone, in a background of white and a normal painless gene.
Figure 4B:
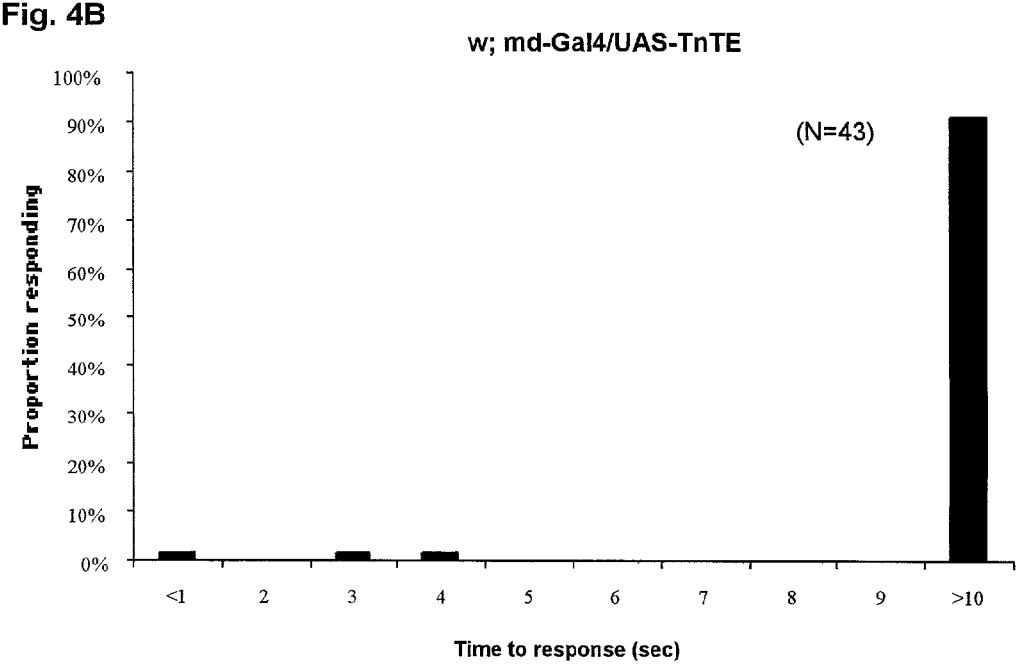
FIG. 4B shows that the same driver as in 3A activating tetanus toxin in md-neurons blocked the response. Since tetanus toxin prevents evoked synaptic activity in a cell autonomous manner through cleavatge of sybaptobrevin, this result deomnstrates that the neurons an circuitry targeted by the drivedr are essential for nociception.

Unexpectedly, both Gal4 induced transcripts contain in-frame start methionines upstream of the normal start methionine. These upstream methionines are encoded by sequences from within the 3' end of the EP-element. Indeed, methionines are present in all three reading frames at the 3' end of the EP-element. These are such that all EP elements have the potential to generate Gal4 dependent, N-terminal fusion proteins with downstream genes in the absence of an in frame stop codon. In painless[1] the P-element encoded, Gal4 dependent, start methionine is predicted to add 65 amino acids to the N-terminus of painless to encode a protein that will be referred to as painless$^{N65}$. In painless[3], the Gal4 dependent methionine is in a different reading frame and adds 24 amino acids, distinct from those of painless$^{N65}$, to produce a protein that will be referred to as painless$^{N24}$. Thus, over-expression of painless$^{N65}$ creates a dominant negative phenotype while the painless$^{N24}$ protein has no effect when over-expressed. The dominant phenotype conferred by painless[1] is Gal4 dependent as painless[1]/+ larvae show a normal response (FIG. 4G). Therefore, this phenotype is due to effects in the neurons targeted by md-gal4 suggesting the possibility that painless normally functions in these cells.

The phenotype of painless[1]/md-gal4 larvae could conceivably be due to a genetic interaction between the two P-element insertions which does not depend on gal4 expression. Therefore, painless[1] was crossed to a different driver, pan-neuronal ELAV-gal4, and the response of the resulting larvae was examined. Larvae containing a single copy of ELAV-gal4 and painless[1] showed the same painless phenotype as was seen with the md-gal4 driver (FIG. 4H).

Nociceptors in vertebrates have been found to be divisible into several classes. Low threshold, polymodal nociceptors respond to noxious heat in the range of 42–48° C., while high threshold nociceptors respond at higher temperatures. To test whether the gal4-dependent effect in painless] blocks all nociception, painless[1] was again crossed it to the pan-neuronal ELAV-gal4 driver and examined the response of the resulting larvae over a range of temperatures. The larvae also failed to respond to a 48° C. stimulus (FIG. 4I). However, 52° C. or higher elicited a rapid response which was similar to that of normal larvae (FIG. 4J). Similar results were obtained using md-gal4 driver to drive painless$^{N65}$ or in loss of function homozygous mutant painless[1] larvae. These results suggest that, as in vertebrates, distinct pathways for detecting high and low level noxious heat stimuli exist in *Drosophila*. Furthermore, the motor system needed for the response is not abolished by mutations in painless, the defect is at the sensory level.

EXAMPLE 5

Altered Gene Expression in Painless1/md-gal4

To test whether the dominant insensitivity of painless[1]/md-gal4 larvae might be due to developmental defects in neural patterning, the expression pattern of UAS-Green Fluorescent Protein (GFP) under control of md-gal4 as compared with the driver alone was examined. In second instar larvae the number, positions, and branching patterns of md neurons were unaffected by the presence of painless[1] suggesting that embryonic development of md-neurons is not changed. However, in third instar, the stage used in the genetic screen, reduced or abolished expression of GFP occurred in a subset of md-da neurons.

There is a remarkable specificity of this late loss of GFP expression. In larvae heterozygous for md-gal4 and UAS-GFP, five cells of the dorsal cluster are clearly marked by GFP; but, in painless[1]/md-gal4 UAS-GFP there are only four. In the ventral cluster, five cells are positive in normal larvae, but only three in the mutant. Thus, one dorsal md-da neuron, and two ventral ones no longer show the GFP fluorescence as they had in second instar. Interestingly, these neurons which become negative for GFP are morphologically distinct from those which remain GFP positive; they have significantly larger cell bodies. Differences in GFP expression within these cells relative to other md-neurons, may occur because the md neuron specific enhancer of the driver line is negatively regulated in response to painless $^{N65}$. Alternatively, the cells might degenerate or undergo apoptosis.

First, it was shown that GFP negative neurons in painless[1]/md-gal4 larvae are present and intact by immunostaining them with an antibody detecting a pan-neuronal antigen. None of the neurons in the dorsal cluster of painless[1]/md-gal4 larvae stained with vital dies acridine orange or nile blue which would stain apoptic corpses. To see how these cells would look in apoptosis, apoptotic death was forced in them by crossing md-gal4 UAS-GFP to the death promoting genes reaper and Hid under UAS control (UAS-rpr/UAS-Hid). The apoptotic neuronal corpses glowed brightly as green spherical blobs devoid of dendrites and axons before eventually losing fluorescence. In contrast, in painless[1]/md-gal4 UAS-GFP larvae, the GFP fluorescence faded gradually with neuronal morphology apparently intact. Thus, the loss of GFP in these latter cells is not as a result of apoptosis.

To test whether the cells were indeed capable of producing GFP, painless[1] was croosed to the pan-neuronal driver, ELAV-Gal4; UAS-GFP. As mentioned above, the resulting larvae were insensitive to noxious heat as in painless[1]/md-gal4 larvae. However, all of the type II sensory neurons of the peripheral nervous system remained positive for GFP although the basal intensity of GFP epifluorescence driven by ELAV-Gal4 was lower than when driven by md-Gal. These results suggest that the loss of GFP in painless[15]/md-gal4 UAS-GFP larvae is not due to degeneration of those cells in the third instar but occurs by negative regulation specific to the md-gal4 enhancer.

EXAMPLE 6

Subclasses of Type II Sensory Neurons

The md-da neurons thus include at least two classes, one showing negative regulation of the md-gal4 reporter in response to alterations in painless expression, while the other does not. Identified in the present study are additional differences in gene expression between these two cell classes. C161(smid-gal4) a Gal4 enhancer trap in the small-minded gene is reportedly expressed in md-neurons during embryogenesis (Long et al. (1998) Gene 208, 191–9). Upon examination of the expression of UAS-GFP driven by C161 in third instar painless+ larvae, it was found that while widely expressed in md neurons, it lacked expression in precisely the same neuronal subset that negatively regulated md-gal4 in response to painless$^{N65}$ (FIGS. 3A–D).

Figure 3A:
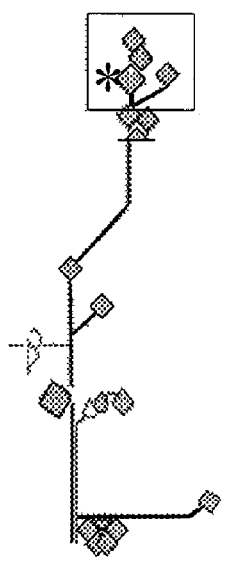
FIG. 3A shows a schematic diagram of the md neurons of an abdominal hemi-segment; expression pattern of md-Gal4 is shown as filled cells. Diamond shapes indicate md-da neurons, half diamonds indicate md-bp neurons and tear shaped cells indicate md-td neurons.
Figure 3B:
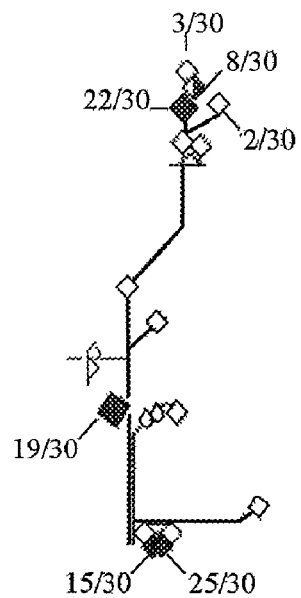
FIG. 3B shows negative regulation of the md-Gal4 reporter in third instar md-Gal4/painless[1] larvae. Cells that show consistent negative regulation of the md-Gal4 reporter are indicated by a dark shape. The number of cells that inactivated Green Fluorescent Protein (GFP) out of a total of 30 cells (in hemi-segments from 15 larvae; abdominal segments 6 and 7) is shown as a ratio. Unlabelled white cells were always GFP positive.
Figure 3C:
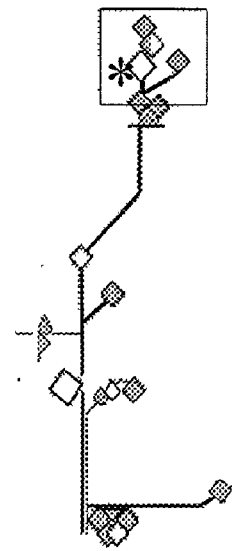
FIG. 3C shows cells that express smid-(gray shapes). One cell in the dorsal cluster which is variable for GFP expression driven by smid-Gal4 is indicated as half gray.
Figure 3D:
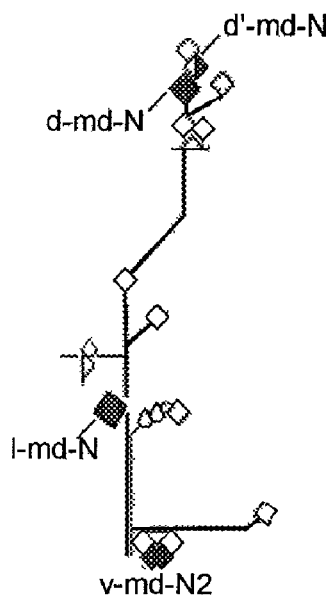
FIG. 3D shows the cells that are proposed herein to be larval nociceptors (indicated by filled shape); there are 2 dorsally (d-md-N and d'-md-N), one laterally (1-md-N), and two ventrally (v-md-N2).
Figure 3E:
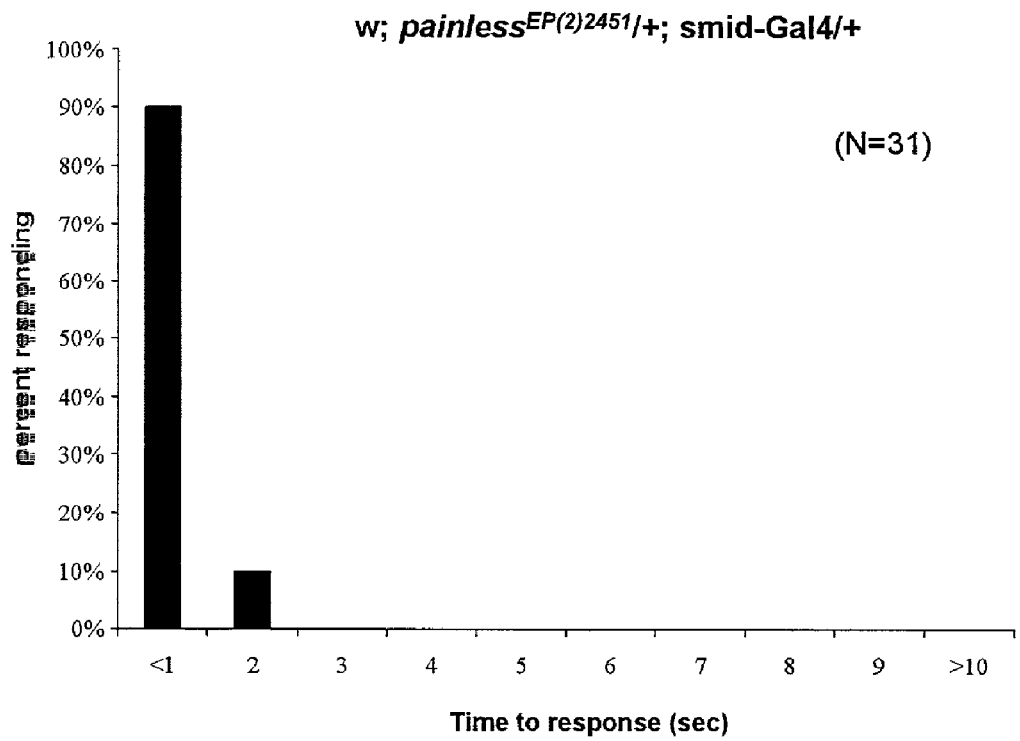
FIG. 3E shows that the expression of painless[N65] in the pattern of smid-Gal4 has no effect on nociceptive behavior.
Figure 3F:
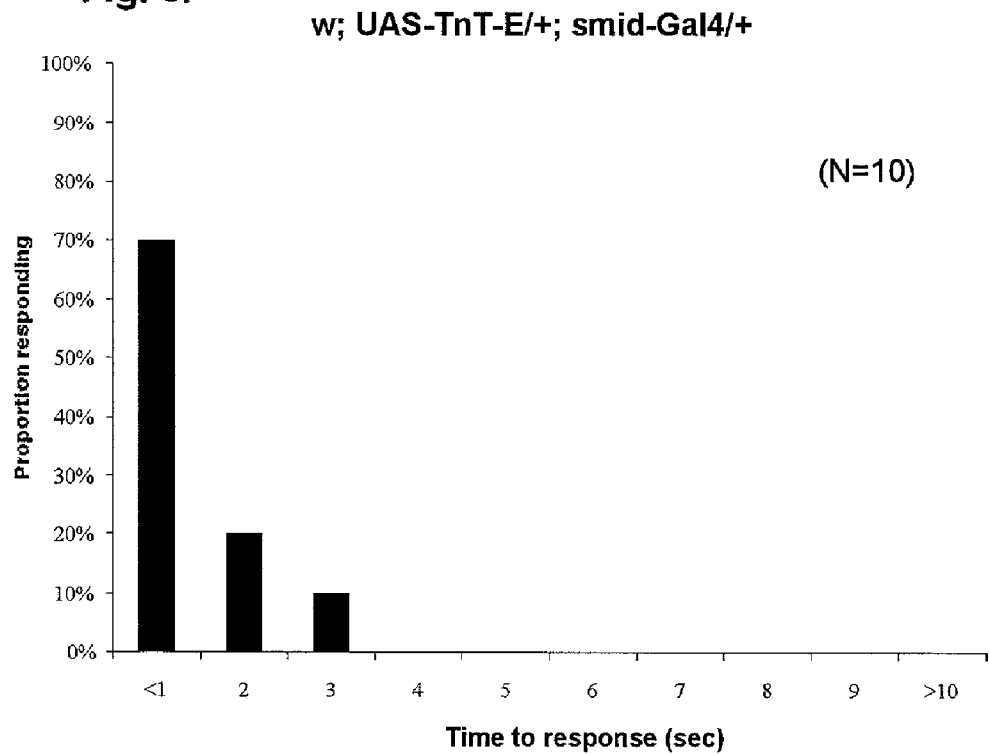
FIG. 3F shows that the expression of tetanus toxin in the pattern of smid-Gal4 does not abolish the response of larvae to noxious heat.

Because smid-gal4 was expressed in the "other" neurons, one could test whether those are necessary for nociception. smid-gal4 flies were crossed with UAS-TetLx, and painless[1] and the response of the resulting larvae was measured in the noxious heat paradigm. The larvae resulting from these crosses show a normal response to noxious heat (FIGS. 3E and 3F). This is in contrast to the result of driving TetLx and painless[1] with md-gal4 which inactivates the response. Combined, these results suggest that the md-da neurons defined by their late onset, negative regulation of the md-gal4 reporter, as well as by lack of expression of smid-gal4, are both necessary and sufficient for transmission of nociceptive information to the CNS. Therefore, these cells are designated as md-n for multi-dendritic nociceptors (FIG. 3D).

The products of the painless gene may control the membrane potential in a temperature-dependent fashion similar to the vertebrate vanilloid receptor. As such, painless and the vanilloid receptor may have each descended from a molecule utilized for nociception in a common ancestor of insects and mammals. Although painless is related to the vanilloid receptor, it may not be a Drosophila orthologue to VR1. In heterologous expression systems such as Xenopus oocytes and HEK cells VR1 shows a heat activated current in the 42–48° C. range. However, mice mutant for VR1 show a normal behavioral output to noxious heat in this temperature range, precisely the heat range in which painless mutant larvae fail to respond. It will be interesting to investigate the possibility that vertebrate a gene more closely related to painless will play an important role in sensing these temperatures.

In conclusion, described herein is a novel and sensitive paradigm for studying nociception in Drosophila. This system can be used as a model to uncover novel molecules homologous to ones important to vertebrate pain pathways. Indeed, mutations in a fly locus encoding a molecule related to the human pain processing vanilloid receptor in the screen for mutants insensitive to noxious heat have been identied. Thus, this paradigm is a model for pain. To use the term in respect to an insect, is not meant to imply that the higher order processes in human perception of pain are operating here. Nociception is to pain as phototransduction is to vision. painless is the first of the genes from this screen to be analyzed in detail, others may lead to a genetic dissection of the pathways involved.

EXAMPLE 7

A Reproducible Noxious Heat Stimulus

The probe used consisted of a soldering iron attached to a variac which was used to indirectly adjust the temperature through the voltage to the iron. The tip of the probe was 0.6 mm wide. The probe was adjusted to maintain a temperature in the range of 42–48° C. by measurement with a fine thermocouple. Those of skill in the art can identify other methods that can be used for delivering a noxious heat stimulus, e.g., a laser, or intense light. To deliver the stimulus, the probe is lightly touched to the larva and the voltage triggered. The resistance provided by the larval cuticle should prevent direct depolarization of neurons by the electrical current itself.

The exact temperature of probes produced by the different voltage regimes is determined empirically. Using untreated wild type larvae, a scale is developed and used in quantifying the qualitative behavioral output produced by a given probe. This allows a probe to be calibrated according to the average response it produces. A sample version of such a scale is as follows: no response=0, move away without rolling=1, roll once then move away=2, roll two to four times then move away=3, roll greater than four times=4 etc. To show that the score is related to the intensity of the stimulus, probes of different known temperatures are tested to determine the effects of stronger and weaker stimuli. A calibrated scale will allow the comparison of a similar stimulus in different populations of larvae. For example, with a given probe wild type larvae might have an average response of 3 but larvae of a different genotype might have a lower average score or a higher average score.

Existing mutations have been found in a number of interesting candidate genes. Visible markers scorable during larval stages can be used to unambiguously identify mutant larvae and they will be tested for their response to noxious heat. Mutations thought to affect the developmental biology of multi-dendritic neurons will be tested (e.g., viable alleles of cut and numb). Testing of larvae containing null mutations in the vanilloid receptor homologues trp and trpl will also be performed. Interestingly, trp and trpl were first identified due to their involvement in photo transduction. This suggests the possibility that the pathways of nociception and phototransduction may utilize common molecular machinery. Therefore other Drosophila mutants that affect phototransduction pathways will also be assayed in the noxious heat nociception paradigm. These mutations include, but are not limited to, norpA, inaC, and inaD. A negative result in these experiments will not exclude the possibility that other Drosophila genes related to these phototransduction molecules function in nociception.

Functional characterization of type II sensory neurons in Drosophila. It is believed that md neurons function as nociceptors in Drosophila. Accordingly, ablation of md neurons or interfering with md neurons or interfering with md neuron function will eliminate or reduce nocifensive behavior in larvae. Two lacZ enhancer traps (E7–2-36 and E6–2-11) have been identified which specifically drive expression of lacZ in the majority of md neurons and not in other neurons or in cells outside the nervous system. These lines will be used to identify cis-acting elements responsible for generating the md neuron specific expression pattern. These cis-acting elements will be used to create transgenic fly lines that drive expression of the yeast transcription factor gal4 specifically in md-neurons (md-gal4). The md-gal4 line can then be used to drive expression of interesting target genes specifically in md-neurons utilizing the gal4/UAS system.

To isolate flanking genomic DNA from the E7-2-36 and E6-2-11 insertion sites, inverse PCR or plasmid rescue will be used. P1 clones containing this DNA will then be identified. DNA fragments containing putative md neuron specific cis acting elements will be cloned and placed upstream of gal4 in the p-element vector pGATB. Stable transgenic fly lines containing insertion of this p-element will be generated by standard techniques and crossed to UAS-GFP or UAS-lacZ. Embryos from this cross will be examined for GFP or lacZ expression in md-neurons. Lines containing specific expression of GFP or lacZ in all md neurons or in small subsets of md-neurons (md-gal4 lines) will be utilized in experiments described below. If sufficient cis-acting elements are not located in the initially attempted DNA fragments larger fragments or fragments located further upstream and downstream of the insertion site will be utilized in similar experiments.

Genetic interference with type II sensory neuron function. To test for effects of specific ablation of md-neurons on nociception. Homozygous md-gal4 adults are crossed to a UAS-hid UAS-reaper stock. This cross results in apoptosis of md neurons. Apoptosis in the md-neurons of the md-gal4/UAS-hid/UAS-reaper embryos is verified by labeling apoptotic cells with TUNEL staining. The resulting larvae are tested for normal nocifensive behavior. If md-neurons function as nociceptors these larvae should fail to respond to noxious stimuli. To be certain that a lack of response is specific to nociceptive behavior and not to non-specific effects on the nervous system, these larvae will be subjected to other tests for normal behavior. For example, larvae are observed for gross defects in normal movement. Also a normal response to a light mechanical touch, which is thought to require type I neurons and not type II neurons, is tested. It is possible or even likely that genetic ablation of all md neurons will severely reduce viability. Therefore, complementary strategies will be taken such that md-gal4 will be used to drive expression of genes expected to have lower levels of toxicity which are likely to specifically block neuronal function. UAS-TeTxLC is used for this purpose. This line drives expression of the light chain of tetanus toxin and blocks synaptic vesicle fusion through cleavage of synaptobrevin, and thus blocks evoked synaptic vesicle release.

Electrophysiology of md neurons. Experiments utilizing md-gal4 that result in effects to nocifensive behavior suggest an involvement for md-neurons in nociception, however, these experiments will not prove that these cells function as nociceptors. To prove nociceptive function it will be necessary to develop a technique for electrophysiological recording from these cells. It will then be possible to demonstrate that md neurons fire in response to noxious thermal, mechanical, and/or chemical stimuli. The nocifensive behavioral response of Drosophila larvae can be broken down into several components: transduction, central processing, and behavioral output. In the genetic screen described herein, mutations that cause an enhanced or decreased behavioral response could do so by affecting the nociceptive pathway at several levels. Therefore it is important to have an independent method to classify mutations according to different steps of the pathway affected. Electrophysiological techniques can be used to separate mutants into classes that affect the transduction step as opposed to steps downstream of transduction. Existing lines expressing GFP in the PNS line are used to correctly identify md neurons using fluorescence microscopy in the electrophysiological preparation. Multi-dendritic neurons can be identified according to their consistent location in the hemisegment relative to other neurons as well as their branching morphology. Both intracellular and extracellular recording techniques can be performed. To be certain that the md-neurons are disturbed as little as possible during the dissection, the procedure is performed using a stereo dissecting microscope equipped with GFP epifluorescence. This allows visualization of the target cells throughout the procedure. Once access to the md-neuron of interest is gained, the remaining shell of the larvae is transferred to a suitable recording chamber and oriented cuticle side down. The md-neurons are then impaled and characterized according to their electrophysiological response to noxious stimuli.

A genetic screen for defects in nocifensive behavior. A forward genetic screen of the third chromosome is undertaken to identify mutations that affect the nocifensive response of Drosophila larvae. Although pilot screens such as this have traditionally utilized the X-chromosome due to the fewer number of generations required for analysis of recessive traits, the third chromosome was chosen for this study for several reasons. Most importantly, the development of p-element mediated male recombination allows rapid genetic mapping of autosomal mutations to precise intervals. Using this technique a mutation can be mapped to an interval as small as 50 kilobases in several generations.

To generate lines containing a mutation induced by a chemical, radiation, or insertion of an exogenous polynucleotide sequence, genetic crosses are performed using methods known to those of skill in the art.

The isogenic third chromosome used in the screen will contain the visible recessive markers roughoid and claret. These markers were chosen due to their location near the end of the left arm and right arm of chromosome III and will greatly facilitate p-element mediated mapping by male recombination. The other recessive markers are present to allow for removal of the mutagenized X and II chromosome respectively.

In the $G_0$ generation males of the indicated genotype are fed the mutagen ethylmethane sulfonate (ems) using standard techniques. The $F_2$ crosses will be generated and maintained at 25° for one week. At this point, the vials will be cleared of the $F_2$ parents and half of the larvae of a vial will be scooped from the media and transferred to small agar plated petri-dishes. Tubby+ larvae are tested for nocifensive behavior, and the response scored. As an initial test, five to ten Tubby+ larvae of each stock are tested. Stocks which contain significantly lower or higher scores than the average score seen for the unmutagenized stock are propagated and retested. In the screen two probes are used. One probe is heated to a temperature which is at the lower threshold for eliciting nocifensive behavior. Use of a probe such as this results in the ability to detect mutations that cause an increased sensitivity to the stimulus. The second probe is heated to a temperature that reproducibly elicits the rolling behavior described above. This probe is used to test for mutations that cause insensitivity to the noxious heat stimulus.

It is possible that stocks that are weak due to generally deleterious mutations might have a reduced response to the stimulus. Of course, this is not the type of mutation which is desired in this screen. Therefore, to minimize the number of stocks that need to be maintained for further retesting, counterscreens are performed on stocks that show a low response in the first round of screening. As a test for the general ability of larvae to roll they will be turned onto their backs. Wild type larvae right themselves in this situation using a motion similar to that seen in the response to a noxious stimulus. Stocks that fail these secondary tests are not analyzed further. Initially, a limited number of lines are chosen for molecular analysis based on their developmental and physiological phenotypes.

Mutagenesis and screen. Drosophilia lines carrying P(lacZ, w+) were screened for mutations causing reduced nociceptive reflexes (e.g., roll over) in response to a hot tipped probe. Candidate "painless" flies showing reduced reflexes compared with the parent strain were examined.

To identify the affected gene in these painless flies, genomic DNA was extracted from E7-2-36 flies using standard techniques. To clone DNA flanking the P-element plasmid rescue (Hamilton and Zinn, Methods in Cell Biology 44: 90-91, 1994) was performed using EcoRI as the restriction enzyme to clone the 5' end of the P-element. Several independent isolates were obtained and sequenced with a P-element specific primer. The sequence shown below contains 142 base pairs of P-element sequence up to the junction of Drosophila genomic DNA. To identify the site of insertion in the fly genome the DNA above was used in a blast search at the Berkeley Drosophila Genome Database (http://www.fruitfly.org). A highly significant match was found beginning at base 134,209 of BACR48K04 (Genbank Accession No. AC007451, which is incorporated herein by reference in its entirety). Sequence flanking the E7-2-36 insertion site (SEQ ID NO:11): GGTTAATCAA-CAATCATATCGCTGTCTCACTCAGNCTCAATACGAC ACTCAGAATACTATTCCTTTCACTCGCACTTAGTG CAAGCATACGNTAAGTGGATGTCTCTTGCCGAC GGGACCACCTTATGTTATTTCATCATGGTTTGCG CCAAGTTTTCTGATTTCATNCGGTGTTTTGGACTC GGCGAGACTGGAAGTTGATGCTGCCGCGTGAATG CCATCGTCGGTCAGGTATTAAAACGTGACNCTTCT ANTTCGCGTGTGANTCCCCCGAGTNTGCAGTCG ATTTGTGCNCAGAAAACATTCAAGATGCCTTGTNTA CTTTGTGAAAAGATCTAATAACACTATGAAACTT AAATCAATGTGCAAGTGACGGTTATATAAATTAAT TATNTTAATTCAAAGCNTAANTAATGCGAAGAGCC TGNAAATAAAGTACNCTAAAANTATTCCCNGGAN ACNTAATTTNTGTCGACATAACTCGAACAACTNATA GTTGAATAATCACCGGGGCCCGACATTTTGGCTG NAGAATACNA ATTTTCCT This insertion occurs between two putative transcription units. The genescan sequence predicts proteins from these transcription units that are highly similar to each other. Both genes encode proteins with high similarity to the yeast gene RIB2P also known as DRAP deaminase. Yeast mutants in RIB2P are reported to be auxotrophic for riboflavin. However, a direct biochemical demonstration of a role of this protein in riboflavin biosynthesis, per se is lacking. Domains present in these predicted proteins include a double stranded RNA binding domain, a pseudouridine synthase domain, and a deaminase domain. It is thus possible that these proteins play a role in RNA editing. There is a third transcription unit in the vicinity of E7-2-36 (Accession Number CG13143; see FIGS. 10A (SEQ ID NO:9) and 10B (SEQ ID NO:10).

The painless insertion is about 900 base pairs from the putative transcriptional start site of a transcript tentatively named DRAP deaminase 1 and approximately 2000 base pairs from a putative transcript named DRAP deaminase 2. Several EST's exist in the region of DRAP deaminase 2, LD40728, GM07410, LD19773 and GM09695, all of which are incorporated herein by reference.

Molecular cloning of the painless gene. Genomic DNA sequences adjacent to the P-element insertion were identified via data from the Drosophila Berkeley genome project. A cDNA clone containing the painless gene can be purchased or derived by known molecular biology techniques. A single insertion of the P-element can be confirmed by genomic Southern blots and it is expected that precise excision of the P-element from the mutant will restored the normal phenotype.

Antibody Staining. Third instar larvae were dissected with a longitudinal incision along the ventral cuticle. Internal organs were removed and the resulting shell of the larvae containing muscle, peripheral nervous system, epidermis and cuticle was fixed for 5 minutes in buffer containing 4% formaldehyde. This was followed by 0.5% NP40 for 5 minutes, then 5% goat serum for one hour. Rabbit anti-lomTK-1 (Reviewed in Nassel, Peptides 20:141–158, 1999) (a gift from Dick Nassel, Stockholm University) diluted was incubated overnight with the specimen, followed by a one hour wash in buffer. The specimen was then incubated in combination of CY3 labelled anti-rabbit antibody and anti-horseradish peroxidase conjugated to FITC (this antibody labels all neurons in Drosophila). The secondary antibody incubation was also overnight followed by a one hour wash in buffer, mounting in glycerol.

In addition, genetic abalation of the md-neurons in larvae completely abolishes the nocifensive behavior. When the nocifensive behavior of UAS-RPR/UAS-Hid; mid-gal/+larvae was examined, they were found to be unresponsive to noxious heat.

While the invention has been described in detail with reference to certain preferred embodiments thereof, it will be understood that modifications and variations are within the spirit and scope of that which is described and claimed.

What is claimed is:

1. A method of identifying an agent that modulates a nociceptive reflex response comprising:
   (a) contacting a *Drosophila melanogaster* organism having an endogenous polynucleotide encoding a polypeptide as set forth in SEQ ID NO:2 with an agent suspected of having nociceptive pain reflex modulating activity; and
   (b) comparing the expression of the polynucleotide in the presence of the agent to the expression of the polynucleotide in the absence of the agent, wherein a difference in expression is indicative of an agent that modulates a nociceptive pain reflex response.

2. The method of claim 1, wherein the agent is selected from the group consisting of a peptide, a peptidomimetic, a chemical, and a nucleic acid sequence.

3. The method of claim 1, further comprising applying a nociceptive stimulus to the organism following contacting the organism with the agent, and measuring a change in a nociceptive pain reflex response in the presence of the agent as compared to the nociceptive pain reflex response in the absence of the agent.

4. The method of claim 3, wherein the nociceptive stimulus is heat.

5. The method of claim 3, wherein the stimulus is mechanical or chemical.

* * * * *

SEQUENCE LISTING

<160> NUMBER OF SEQ ID NOS: 13

<210> SEQ ID NO 1
<211> LENGTH: 2742
<212> TYPE: DNA
<213> ORGANISM: Drosophila melanogaster

<400> SEQUENCE: 1

| | | | | | |
|---|---|---|---|---|---|
| atggacttta | acaactgcgg | cttcattgat | ccgcaggccc | agctagctgg | agctttggcc | 60 |
| aagcaggaca | tccgacagtt | cgttgctgcc | ctggacagcg | gtgccctggc | cgatctacaa | 120 |
| gacgaccgcc | ataccagtat | ctacgagaag | gcactctcaa | caccaggttg | tcgtgacttc | 180 |
| attgaagcct | gcatcgacca | cggcagccag | gtgaactaca | tcaacaagaa | gctggacaag | 240 |
| gccgcaatca | gctatgcggc | tgactctagg | gatccaggaa | acctggcggc | tctccttaag | 300 |
| taccgccccg | gaaacaaagt | ccaggttgat | agaaaatatg | ggcagcttac | tccacttaac | 360 |
| tcacttgcca | gaatctcac | ggatgaaaat | gccccagacg | tgtactcctg | catgcaactc | 420 |
| ttgctggact | acgcgcctc | gccgaatatc | gtagaccagg | gcgagttcac | acccttgcac | 480 |
| catgtgctga | aaagagcaa | ggtgaaggct | gggaagaagg | aactgattca | gctctttctg | 540 |
| gaccatccgg | agctggatat | cgatagttac | gaaacggggg | aggtgcgcag | actgctgcag | 600 |
| gcgcaatttc | cggagcttaa | gctgccggaa | gagcgtcata | ccgggccgga | gattgacatc | 660 |
| caaactcttc | aaaggactct | acgggacggg | gacgaaacac | tgtttgagca | gcagttcgct | 720 |
| gagtacttgc | agaatctcaa | aggcggagcg | gataaccaac | taaatgccca | ccaggaggaa | 780 |
| tacttcggac | tgctgcagga | gagcatcaag | aggggcaggc | agcgagcctt | cgatgtcatt | 840 |
| ttgtccactg | gcatggatat | caactcgaga | ccaggcaggg | ccaacgaggc | caatctcgta | 900 |
| gagacggccg | tgatatacgg | taactggcag | gcgttggagc | gactgcttaa | ggagccaaac | 960 |
| ctgcgactta | ctccagactc | caagctacta | aatgcagtaa | tcggccgtct | ggatgagcca | 1020 |
| ccgtatgatg | gctccagcca | ccagcgctgc | tttgaattgc | tcattaacag | cgatcgcgta | 1080 |
| gacatcaacg | aagctgattc | cggacgcctg | gtgcctctgt | tcttcgctgt | taagtaccgc | 1140 |
| aacacgagtg | cgatgcaaaa | actcctgaag | aacggtgcct | acattggttc | taagagcgca | 1200 |
| tttggcacac | tacccatcaa | ggacatgcca | cccgaggttc | tcgaagagca | cttcgactcg | 1260 |
| tgtatcacca | caaacggaga | gaggcctggt | gaccagaact | ttgagatcat | catcgattat | 1320 |
| aagaacctaa | tgcgccagga | gagagactcc | ggactcaacc | agctgcaaga | cgaaatggcc | 1380 |
| ccgatcgcat | tcatcgccga | gtcgaaggag | atgcgccacc | tgctccagca | cccgctgatc | 1440 |
| tcgagctttc | tattcctcaa | gtggcaccga | ctttccgtga | tattctacct | gaacttcctg | 1500 |
| atatactcgc | tttttaccgc | ctccataatt | acctacacgc | tcctcaagtt | ccacgaaagc | 1560 |
| gatcaaaggg | ctcttactgc | attttcgga | ttgctttcct | ggctgggaat | cagctaccct | 1620 |
| atattacggg | agtgcatcca | gtggataatg | tctccagttc | ggtacttttg | gtctataacg | 1680 |
| aatattatgg | aggtggctct | tattacacta | tctatcttta | cctgcatgga | atccagcttc | 1740 |
| gacaaggaga | cgcagcgcgt | cttagccgta | tttaccatcc | tactcgtctc | catggagttt | 1800 |
| tgtttactag | tgggctccct | gccagtgctc | tcaatttcga | cgcacatgct | gatgctgcga | 1860 |
| gaggtgtcaa | acagcttctt | aaagagcttt | accctctact | cgatcttcgt | gctcaccttc | 1920 |
| agcctgtgtt | tctatatcct | cttcggcaag | tcagtggagg | aagaccagtc | taaaagcgct | 1980 |
| acgccatgtc | cacctctggg | gaagaaggag | gggaaggacg | aggaacaggg | cttcaacaca | 2040 |

-continued

```
tttaccaagc ctatcgaggc cgtgatcaag accattgtga tgctgacagg cgagtttgac      2100
gccggaagca tccagtttac cagcatctac acctacctga ttttcctgct cttcgtgatc      2160
tttatgacga tagtgctgtt caaccttttg aacggtcttg cagtgagcga cacccaagtt      2220
attaaggctc aggcggaact gaacggagcc atttgcagaa ccaacgtcct tagtcggtac      2280
gagcaggttc tcactggcca cggacgcgct gggttttttgt tgggcaacca tctcttccgc     2340
agcatctgcc aacgtttgat gaacatctac ccgaactact aagtctgcg tcagatttcc       2400 gtgctgccga acgatggaaa caaagtgctt attccaatga cgatcccctt cgaaatgagg      2460
acccttaaga aggctagctt tcagcaattg ccctgagtg ctgcagtgcc ccagaagaag       2520
ctgttggatc caccgcttag acttctgccc tgctgctgtt ccctgctcac cggaaagtgc      2580
tcccagatga gcggccgggt ggtcaaacgg gccctcgagg taatcgatca gaagaacgcg      2640
gcggagcaga ggcggaaaca ggaacagatc aacgacagtc gactgaagct gatcgagtac      2700
aagctggagc aattaataca gctggtccag gaccggaagt ga                        2742
```

<210> SEQ ID NO 2
<211> LENGTH: 913
<212> TYPE: PRT
<213> ORGANISM: Drosophila melanogaster

<400> SEQUENCE: 2

```
Met Asp Phe Asn Asn Cys Gly Phe Ile Asp Pro Gln Ala Gln Leu Ala
1               5                   10                  15

Gly Ala Leu Ala Lys Gln Asp Ile Arg Gln Phe Val Ala Ala Leu Asp
            20                  25                  30

Ser Gly Ala Leu Ala Asp Leu Gln Asp Asp Arg His Thr Ser Ile Tyr
        35                  40                  45

Glu Lys Ala Leu Ser Thr Pro Gly Cys Arg Asp Phe Ile Glu Ala Cys
    50                  55                  60

Ile Asp His Gly Ser Gln Val Asn Tyr Ile Asn Lys Lys Leu Asp Lys
65                  70                  75                  80

Ala Ala Ile Ser Tyr Ala Ala Asp Ser Arg Asp Pro Gly Asn Leu Ala
                85                  90                  95

Ala Leu Leu Lys Tyr Arg Pro Gly Asn Lys Val Gln Val Asp Arg Lys
            100                 105                 110

Tyr Gly Gln Leu Thr Pro Leu Asn Ser Leu Ala Lys Asn Leu Thr Asp
        115                 120                 125

Glu Asn Ala Pro Asp Val Tyr Ser Cys Met Gln Leu Leu Leu Asp Tyr
    130                 135                 140

Gly Ala Ser Pro Asn Ile Val Asp Gln Gly Glu Phe Thr Pro Leu His
145                 150                 155                 160

His Val Leu Arg Lys Ser Lys Val Lys Ala Gly Lys Lys Glu Leu Ile
                165                 170                 175

Gln Leu Phe Leu Asp His Pro Glu Leu Asp Ile Asp Ser Tyr Arg Asn
            180                 185                 190

Gly Glu Val Arg Arg Leu Leu Gln Ala Gln Phe Pro Glu Leu Lys Leu
        195                 200                 205

Pro Glu Glu Arg His Thr Gly Pro Glu Ile Asp Ile Gln Thr Leu Gln
    210                 215                 220

Arg Thr Leu Arg Asp Gly Asp Glu Thr Leu Phe Glu Gln Gln Phe Ala
225                 230                 235                 240

Glu Tyr Leu Gln Asn Leu Lys Gly Gly Ala Asp Asn Gln Leu Asn Ala
```

-continued

```
                    245                 250                 255
His Gln Glu Glu Tyr Phe Gly Leu Leu Gln Glu Ser Ile Lys Arg Gly
                260                 265                 270

Arg Gln Arg Ala Phe Asp Val Ile Leu Ser Thr Gly Met Asp Ile Asn
            275                 280                 285

Ser Arg Pro Gly Arg Ala Asn Glu Ala Asn Leu Val Glu Thr Ala Val
        290                 295                 300

Ile Tyr Gly Asn Trp Gln Ala Leu Glu Arg Leu Leu Lys Glu Pro Asn
305                 310                 315                 320

Leu Arg Leu Thr Pro Asp Ser Lys Leu Leu Asn Ala Val Ile Gly Arg
                325                 330                 335

Leu Asp Glu Pro Pro Tyr Asp Gly Ser Ser His Gln Arg Cys Phe Glu
            340                 345                 350

Leu Leu Ile Asn Ser Asp Arg Val Asp Ile Asn Glu Ala Asp Ser Gly
        355                 360                 365

Arg Leu Val Pro Leu Phe Phe Ala Val Lys Tyr Arg Asn Thr Ser Ala
    370                 375                 380

Met Gln Lys Leu Leu Lys Asn Gly Ala Tyr Ile Gly Ser Lys Ser Ala
385                 390                 395                 400

Phe Gly Thr Leu Pro Ile Lys Asp Met Pro Pro Glu Val Leu Glu Glu
                405                 410                 415

His Phe Asp Ser Cys Ile Thr Thr Asn Gly Glu Arg Pro Gly Asp Gln
            420                 425                 430

Asn Phe Glu Ile Ile Ile Asp Tyr Lys Asn Leu Met Arg Gln Glu Arg
        435                 440                 445

Asp Ser Gly Leu Asn Gln Leu Gln Asp Glu Met Ala Pro Ile Ala Phe
    450                 455                 460

Ile Ala Glu Ser Lys Glu Met Arg His Leu Leu Gln His Pro Leu Ile
465                 470                 475                 480

Ser Ser Phe Leu Phe Leu Lys Trp His Arg Leu Ser Val Ile Phe Tyr
                485                 490                 495

Leu Asn Phe Leu Ile Tyr Ser Leu Phe Thr Ala Ser Ile Ile Thr Tyr
            500                 505                 510

Thr Leu Leu Lys Phe His Glu Ser Asp Gln Arg Ala Leu Thr Ala Phe
        515                 520                 525

Phe Gly Leu Leu Ser Trp Leu Gly Ile Ser Tyr Leu Ile Leu Arg Glu
    530                 535                 540

Cys Ile Gln Trp Ile Met Ser Pro Val Arg Tyr Phe Trp Ser Ile Thr
545                 550                 555                 560

Asn Ile Met Glu Val Ala Leu Ile Thr Leu Ser Ile Phe Thr Cys Met
                565                 570                 575

Glu Ser Ser Phe Asp Lys Glu Thr Gln Arg Val Leu Ala Val Phe Thr
            580                 585                 590

Ile Leu Leu Val Ser Met Glu Phe Cys Leu Leu Val Gly Ser Leu Pro
        595                 600                 605

Val Leu Ser Ile Ser Thr His Met Leu Met Leu Arg Glu Val Ser Asn
    610                 615                 620

Ser Phe Leu Lys Ser Phe Thr Leu Tyr Ser Ile Phe Val Leu Thr Phe
625                 630                 635                 640

Ser Leu Cys Phe Tyr Ile Leu Phe Gly Lys Ser Val Glu Glu Asp Gln
                645                 650                 655

Ser Lys Ser Ala Thr Pro Cys Pro Pro Leu Gly Lys Lys Glu Gly Lys
            660                 665                 670
```

-continued

```
Asp Glu Glu Gln Gly Phe Asn Thr Phe Thr Lys Pro Ile Glu Ala Val
            675                 680                 685
Ile Lys Thr Ile Val Met Leu Thr Gly Glu Phe Asp Ala Gly Ser Ile
690                 695                 700
Gln Phe Thr Ser Ile Tyr Thr Tyr Leu Ile Phe Leu Leu Phe Val Ile
705                 710                 715                 720
Phe Met Thr Ile Val Leu Phe Asn Leu Leu Asn Gly Leu Ala Val Ser
            725                 730                 735
Asp Thr Gln Val Ile Lys Ala Gln Ala Glu Leu Asn Gly Ala Ile Cys
            740                 745                 750
Arg Thr Asn Val Leu Ser Arg Tyr Glu Gln Val Leu Thr Gly His Gly
            755                 760                 765
Arg Ala Gly Phe Leu Leu Gly Asn His Leu Phe Arg Ser Ile Cys Gln
            770                 775                 780
Arg Leu Met Asn Ile Tyr Pro Asn Tyr Leu Ser Leu Arg Gln Ile Ser
785                 790                 795                 800
Val Leu Pro Asn Asp Gly Asn Lys Val Leu Ile Pro Met Ser Asp Pro
            805                 810                 815
Phe Glu Met Arg Thr Leu Lys Lys Ala Ser Phe Gln Gln Leu Pro Leu
            820                 825                 830
Ser Ala Ala Val Pro Gln Lys Lys Leu Leu Asp Pro Pro Leu Arg Leu
            835                 840                 845
Leu Pro Cys Cys Cys Ser Leu Leu Thr Gly Lys Cys Ser Gln Met Ser
850                 855                 860
Gly Arg Val Val Lys Arg Ala Leu Glu Val Ile Asp Gln Lys Asn Ala
865                 870                 875                 880
Ala Glu Gln Arg Arg Lys Gln Glu Gln Ile Asn Asp Ser Arg Leu Lys
            885                 890                 895
Leu Ile Glu Tyr Lys Leu Glu Gln Leu Ile Gln Leu Val Gln Asp Arg
            900                 905                 910
Lys

<210> SEQ ID NO 3
<211> LENGTH: 3078
<212> TYPE: DNA
<213> ORGANISM: Drosophila melanogaster

<400> SEQUENCE: 3
tgcggtcgct ttcacggatc agattagtcg ttgtctggat attaacgagg aagaccaaac      60
caatggactt taacaactgc ggcttcattg atccgcaggc ccagctagct ggagctttgg     120
ccaagcagga catccgacag ttcgttgctg ccctggacag cggtgccctg ccgatctac      180 aagacgaccg ccataccagt atctacgaga aggcactctc aacaccaggt tgtcgtgact     240
tcattgaagc ctgcatcgac cacggcagcc aggtgaacta catcaacaag aagctggaca     300
aggccgcaat cagctatgcg gctgactcta gggatccagg aaacctggcg gctctcctta     360
agtaccgccc cggaaacaaa gtccaggttg atagaaaata tgggcagctt actccactta     420
actcacttgc caagaatctc acggatgaaa atgccccaga cgtgtactcc tgcatgcaac     480
tcttgctgga ctacgcgcc tcgccgaata tcgtagacca gggcgagttc acacccttgc     540
accatgtgct gagaaagagc aaggtgaagg ctgggaagaa ggaactgatt cagctctttc     600
tggaccatcc ggagctggat atcgatagtt accgaaacgg ggaggtgcgc agactgctgc     660
aggcgcaatt tccggagctt aagctgccgg aagagcgtca taccgggccg gagattgaca     720
```

-continued

```
tccaaactct tcaaaggact ctacgggacg gggacgaaac actgtttgag cagcagttcg      780
ctgagtactt gcagaatctc aaaggcggag cggataacca actaaatgcc caccaggagg      840
aatacttcgg actgctgcag gagagcatca agaggggcag gcagcgagcc ttcgatgtca      900
ttttgtccac tggcatggat atcaactcga gaccaggcag ggccaacgag gccaatctcg      960
tagagacggc cgtgatatac ggtaactggc aggcgttgga gcgactgctt aaggagccaa     1020
acctgcgact tactccagac tccaagctac taaatgcagt aatcggccgt ctggatgagc     1080
caccgtatga tggctccagc caccagcgct gctttgaatt gctcattaac agcgatcgcg     1140
tagacatcaa cgaagctgat tccggacgcc tggtgcctct gttcttcgct gttaagtacc     1200
gcaacacgag tgcgatgcaa aaactcctga agaacggtgc ctacattggt tctaagagcg     1260
catttggcac actacccatc aaggacatgc cacccgaggt tctcgaagag cacttcgact     1320
cgtgtatcac cacaaacgga gagaggcctg gtgaccagaa ctttgagatc atcatcgatt     1380
ataagaacct aatgcgccag gagagagact ccggactcaa ccagctgcaa gacgaaatgg     1440
ccccgatcgc attcatcgcc gagtcgaagg agatgcgcca cctgctccag cacccgctga     1500
tctcgagctt tctattcctc aagtggcacc gactttccgt gatattctac ctgaacttcc     1560
tgatatactc gcttttttacc gcctccataa ttacctacac gctcctcaag ttccacgaaa     1620
gcgatcaaag ggctcttact gcattttttcg gattgctttc ctggctggga atcagctacc     1680
ttatattacg ggagtgcatc cagtggataa tgtctccagt tcggtacttt tggtctataa     1740
cgaatattat ggaggtggct cttattacac tatctatctt tacctgcatg gaatccagct     1800
tcgacaagga gacgcagcgc gtcttagccg tatttaccat cctactcgtc tccatggagt     1860
tttgtttact agtgggctcc ctgccagtgc tctcaatttc gacgcacatg ctgatgctgc     1920
gagaggtgtc aaacagcttc ttaaagagct ttaccctcta ctcgatcttc gtgctcacct     1980
tcagcctgtg tttctatatc ctcttcggca agtcagtgga ggaagaccag tctaaaagcg     2040
ctacgccatg tccacctctg gggaagaagg agggaaggga cgaggaacag ggcttcaaca     2100
catttaccaa gcctatcgag gccgtgatca agaccattgt gatgctgaca ggcgagtttg     2160
acgccggaag catccagttt accagcatct acacctacct gattttcctg ctcttcgtga     2220
tctttatgac gatagtgctg ttcaacccttt tgaacggtct tgcagtgagc gacacccaag     2280
ttattaaggc tcaggcggaa ctgaacggag ccatttgcag aaccaacgtc cttagtcggt     2340
acgagcaggt tctcactggc cacggacgcg ctgggttttt gttgggcaac catctcttcc     2400
gcagcatctg ccaacgtttg atgaacatct acccgaacta cttaagtctg cgtcagattt     2460
ccgtgctgcc gaacgatgga aacaaagtgc ttattccaat gagcgatccc ttcgaaatga     2520
ggacccttaa gaaggctagc tttcagcaat gcccctgag tgctgcagtg ccccagaaga     2580
agctgttgga tccaccgctt agacttctgc cctgctgctg ttccctgctc accgaaaagt     2640
gctcccagat gagcggccgg gtggtcaaac gggccctcga ggtaatcgat cagaagaacg     2700
cggcggagca gaggcggaaa caggaacaga tcaacgacag tcgactgaag ctgatcgagt     2760
acaagctgga gcaattaata cagctggtcc aggaccggaa gtgaggagaa tgtatttttgg     2820 tagctttagt atttatgaga ctaatcagcc ttttagaacg atttgcattt aacattcagt     2880
ttaaagagcc gagttagtcg gaaattgttt ttattaacat acgagtaatg aaattgaaca     2940
aaacccttaa taattgtcag taagtaagta gtatataatg gttatataga cagtaaatat     3000
tgtataaacg aatatcatta ctgtactatt tgtacccgag taaatattta atttcaaatg     3060
```

| ttaaaaaaaa aaaaaaaa | 3078 |

<210> SEQ ID NO 4
<211> LENGTH: 50
<212> TYPE: DNA
<213> ORGANISM: Drosophila melanogaster

<400> SEQUENCE: 4

| tgcggtcgct ttcacggatc agattagtcg ttgtctggat attaacgagg | 50 |

<210> SEQ ID NO 5
<211> LENGTH: 231
<212> TYPE: DNA
<213> ORGANISM: Drosophila melanogaster

<400> SEQUENCE: 5

| aagaccaaac caatggactt taacaactgc ggcttcattg atccgcaggc ccagctagct | 60 |
| ggagctttgg ccaagcagga catccgacag ttcgttgctg ccctggacag cggtgccctg | 120 |
| gccgatctac aagacgaccg ccataccagt atctacgaga aggcactctc aacaccaggt | 180 |
| tgtcgtgact tcattgaagc ctgcatcgac cacggcagcc aggtgaacta c | 231 |

<210> SEQ ID NO 6
<211> LENGTH: 1999
<212> TYPE: DNA
<213> ORGANISM: Drosophila melanogaster

<400> SEQUENCE: 6

| atcaacaaga agctggacaa ggccgcaatc agctatgcgg ctgactctag ggatccagga | 60 |
| aacctggcgg ctctccttaa gtaccgcccc ggaaacaaag tccaggttga tagaaaatat | 120 |
| gggcagctta ctccacttaa ctcacttgcc aagaatctca cggatgaaaa tgccccagac | 180 |
| gtgtactcct gcatgcaact cttgctggac tacggcgcct cgccgaatat cgtagaccag | 240 |
| ggcgagttca caccccttgca ccatgtgctg agaaagagca aggtgaaggc tgggaagaag | 300 |
| gaactgattc agctctttct ggaccatccg gagctggata tcgatagtta ccgaaacggg | 360 |
| gaggtgcgca gactgctgca ggcgcaattt ccggagctta agctgccgga agagcgtcat | 420 |
| accgggccgg agattgacat ccaaactctt caaaggactc tacgggacgg ggacgaaaca | 480 |
| ctgtttgagc agcagttcgc tgagtacttg cagaatctca aggcggagc ggataaccaa | 540 |
| ctaaatgccc accaggagga atacttcgga ctgctgcagg agagcatcaa gaggggcagg | 600 |
| cagcgagcct tcgatgtcat tttgtccact ggcatggata tcaactcgag accaggcagg | 660 |
| gccaacgagg ccaatctcgt agagacggcc gtgatatacg gtaactggca ggcgttggag | 720 |
| cgactgctta aggagccaaa cctgcgactt actccagact ccaagctact aaatgcagta | 780 |
| atcggccgtc tggatgagcc accgtatgat ggctccagcc accagcgctg ctttgaattg | 840 |
| ctcattaaca gcgatcgcgt agacatcaac gaagctgatt ccggacgcct ggtgcctctg | 900 |
| ttcttcgctg ttaagtaccg caacacgagt gcgatgcaaa aactcctgaa gaacggtgcc | 960 |
| tacattggtt ctaagagcgc atttggcaca ctacccatca aggacatgcc acccgaggtt | 1020 |
| ctcgaagagc acttcgactc gtgtatcacc acaaacggag agaggcctgg tgaccagaac | 1080 |
| tttgagatca tcatcgatta taagaaccta atgcgccagg agagagactc cggactcaac | 1140 |
| cagctgcaag acgaaatggc cccgatcgca ttcatcgccg agtcgaagga gatgcgccac | 1200 |
| ctgctccagc acccgctgat ctcgagcttt ctattcctca gtggcaccg actttccgtg | 1260 |
| atattctacc tgaacttcct gatatactcg ctttttaccg cctccataat tacctacacg | 1320 |

-continued

```
ctcctcaagt tccacgaaag cgatcaaagg gctcttactg cattttttcgg attgctttcc   1380 tggctgggaa tcagctacct tatattacgg gagtgcatcc agtggataat gtctccagtt   1440
cggtactttt ggtctataac gaatattatg gaggtggctc ttattacact atctatcttt   1500
acctgcatgg aatccagctt cgacaaggag acgcagcgcg tcttagccgt atttaccatc   1560
ctactcgtct ccatggagtt tgtttacta gtgggctccc tgccagtgct ctcaatttcg   1620
acgcacatgc tgatgctgcg agaggtgtca acagcttct taaagagctt taccctctac   1680
tcgatcttcg tgctcacctt cagcctgtgt ttctatatcc tcttcggcaa gtcagtggag   1740
gaagaccagt ctaaaagcgc tacgccatgt ccacctctgg ggaagaagga ggggaaggac   1800
gaggaacagg gcttcaacac atttaccaag cctatcgagg ccgtgatcaa gaccattgtg   1860
atgctgacag gcgagtttga cgccggaagc atccagttta ccagcatcta cacctacctg   1920
attttcctgc tcttcgtgat ctttatgacg atagtgctgt tcaaccttt gaacggtctt   1980 gcagtgagcg acacccaag                                                 1999
```

<210> SEQ ID NO 7
<211> LENGTH: 798
<212> TYPE: DNA
<213> ORGANISM: Drosophila melanogaster

<400> SEQUENCE: 7

```
ttattaaggc tcaggcggaa ctgaacggag ccatttgcag aaccaacgtc cttagtcggt     60
acgagcaggt tctcactggc cacggacgcg ctgggttttt gttgggcaac catctcttcc    120
gcagcatctg ccaacgtttg atgaacatct acccgaacta cttaagtctg cgtcagattt    180
ccgtgctgcc gaacgatgga aacaaagtgc ttattccaat gagcgatccc ttcgaaatga    240
ggacccttaa gaaggctagc tttcagcaat tgcccctgag tgctgcagtg ccccagaaga    300
agctgttgga tccaccgctt agacttctgc cctgctgctg ttccctgctc accgaaagt    360 gctcccagat gagcggccgg gtggtcaaac gggccctcga ggtaatcgat cagaagaacg    420
cggcggagca gaggcggaaa caggaacaga tcaacgacag tcgactgaag ctgatcgagt    480
acaagctgga gcaattaata cagctggtcc aggaccggaa gtgaggagaa tgtatttttgg   540 tagctttagt atttatgaga ctaatcagcc ttttagaacg atttgcattt aacattcagt    600
ttaaagagcc gagttagtcg gaaattgttt ttattaacat acgagtaatg aaattgaaca    660
aaacccttaa taattgtcag taagtaagta gtatataatg gttatataga cagtaaatat    720
tgtataaacg aatatcatta ctgtactatt tgtacccgag taaatattta atttcaaatg    780
ttaaaaaaaa aaaaaaaa                                                  798
```

<210> SEQ ID NO 8
<211> LENGTH: 13482
<212> TYPE: DNA
<213> ORGANISM: Drosophila melanogaster

<400> SEQUENCE: 8

```
tcgaggtgct gcagttcttc acgatgcgcg cctggttctt taagtcggat gcctattcct     60
cgctgtgggc catgctaaac gagtcggaca ggaaaaagta cgtagcgcga gcgtagaagg    120
gtactgagtt cacttaatcc gaaacacctg atcccaccca aaagcttcaa tatggacatg    180
gatcccgagg agactgtccc catgtacatt gagtcgtgtg tccagggagg gcgacagtac    240
ctgatgaagg agtcgcccga tagtttgccc cgcgcccggc tccagctgaa gctgtaagcg    300
```

-continued

```
agactcgccc acagggacat aagccctgag cccgatctct aagcacggtc ttcctttcat    360
ttatagaatg tacatcctgg accgcgcttg caagacgctc atcgtgggca ccctgtgcta    420
ctggacctac ggtttggtgg cacgcctgct cggcgtctaa tacgacggcc acccgggaca    480
ttttcaatcc attcgcgcgc ttttctcaat caatctctgc ttaggttcgc ttgggggcat    540
aacttcgagc cactcgacga gtggcctcga atctggtttt catttctact ttaagtgatt    600
atctatgttt cgtgtcaaaa taaaaaatct gtgtactgag tttatgtgtc tgtgcttcaa    660
gtgtacaagt gttgatccag aggactcgcg cgacaacacg aacaacacaa acaaacccca    720
caaaacccac tgaacacaca gatcacacag gacaaagagc acaatgatat tttccccgat    780
tgcgcactat ttcccacctt ctaaattccc acacttatcc ttggcggaaa catagtccaa    840
aacatacaac tacactactc acacccacac catacacaca ttcacacatt cacacataat    900
acggcttcgg tgaccatcat cttgggctcg tggtatgtag actggtttca tgcgctgagc    960
agattagacg cccccttagta aacatctatt ccttccgccc tgtagtgtcg ccggctgcct   1020
acgagccgtt gcccggatgg gtggacaacc tgaatggacc gactggcctg atgatcggat   1080
gcggcaaggg cgtgatccgg tccgttctgg tgaatcagca gaacaaggcc gaggtgattc   1140
ccgtcgacta cgctatcaac gggctgatcg tcattcccta cgagttcaac aagcaggcca   1200
agcggcctac caatgtgccc gtttataata taaccaatgc ggaccacagg aagatgacca   1260
tgggcaccgt tgtggagatg agcaaacgca tcaacaagca gttcccattt aacgcgggtc   1320
tatggtaccc ggacccttgc gttaccacca accaattata ccacaacttc aacgtggctc   1380
tgtttcattg gttgcccgct tacttcctgg acttcctgat gctgatatta ggtcagaagc   1440
gattgtaagt tgccccgcac tgaattaccc caaatggagc ttatgtgcca tttccctccc   1500
tagcatgttg agagttcagg agaagatatc cacaggtctg ggcgtcctcc agttctttac   1560
cctcaatgcc tggtgcttcc gatctgataa ctacgcctcc ctctggaaca aactcaacga   1620
ggaagacaag gcgatgtaag tgctgctatt gaatattaac atattaacat atcaatatca   1680
atttcccatt cagttttaac atgaacatga acacggagaa caccgaggag gagtacatga   1740
ttgagtgtgc taagggcgct cgaaagttta tcctcaagga aaaggaggag gatctgccca   1800
ctgcgcgcgt gcacatgaag atgtaagtta ggcaagagcc tgtgctaccc actatgactc   1860
actcatcttc acttccagcc aacgagtcgt agacgttgtg tgcaagacgg tgattgtggg   1920
actgttcttc tactacctcc ttaagtggac gggggtgctg gctatattct gattctagtt   1980
ctccgtggac ttgcattggt ttggtggtca caggcattta tttagtcaat tagcttagtt   2040
gtagttacgc atattcgagg ttttgaatcc aaataaatat gattgtaggt tgttgaatat   2100
acacatttcg ccaactgcgc cgtgtttctc tttcccaatc cagtcactaa agcagacttt   2160
gtgtctaacc atactgacct gtactttgtt ctccagtaac tccagctgtc gctgagcctc   2220
tgccaggttg ggtggacaat atgaacggac ctacgggagt tctcattggc gccggcaaag   2280
gagttatccg atccatgatc tgcaacgggg agctaaaatc tgaagtgata cctgtggaca   2340
tcgccattaa cggtcttatc ttattaccat atcataacag tcttgcggag aagaggtaaa   2400
ttttttcagac gcctcccatg tcaatgtgat gtataacttc tgccacagac ctcttcagat   2460
cccagtctac aacttgaccg tggacgatgc caaaaagcgc acatggaaat ggataatgga   2520
tgtgggtcgc gacttgggca ttaagtaccc cttcgaagtg ggactctggt atcccgacgg   2580
caacatgacg tccagcaaat tctatcacac catctgtacc attctgttta tgtggctgcc   2640
agcctacctt atcgacttcc tactcctgat cttttggaca cgtcgcttgt aaaaccttca   2700
```

```
aaagaatttg tcagttccga ataagaatct aacccaaaac ttttctgttt gtctagcatg    2760
attcgggttc aaaccaaaat cgctgtgggt ttggaagttt tgcagttctt taccacgcga    2820
agctgggact ttaaatccac acacttcgag cagatctaca aggaattagg atccacagat    2880
cggaggatgt aagcaatata tatcatatgc attcaataga tgaattcatg cattaaatgg    2940
atttataacg taactttatt tacgacagat ttaagattaa caccgacgat gtcgacgatt    3000
atgagtacat gaaagtcagt attttgggtg gccgtcagta tgtgatgaag gaacctttaa    3060
cttcgttgcc gaaatcacgc atacaattga gattgtaagt aatttgttat ttccatctat    3120
agtgtttaac caatgctctt gttttccagc atgtatgtcc tggaccgtat ttgcaaaacg    3180
atgataattt caggccttct atattgggtt tcccaaaaac tgagagtagt tgacctattt    3240
agaagcgtat tccattctag tacataacat tcttcttcag ttgcttttt aacattttgt     3300 acctttatt tcatgtgcct ttgaaagggt tgtaagaaa atcttgttaa aaatattcag      3360
gtgttttgta tacgtaaact tgttattgca agtcgttgat aataaaaatt tttaaacatt    3420
aggctatttg atttcaattt actgttactg tgagttactg ttgtataggt tattttatt     3480 agcactatct tgaagttata caaatttgta aaaatacaga tgagacgagg aatccaactc    3540
gagtcccaaa ctctacagat ctgaatcggt tttgtaccaa attaaggatg atgttccatt    3600
gccgacagat gtagtggaat gaatagaata tttagtatct taaatcactt gtagccgttt    3660
gttattagtt ggctattcgg cacacattta actgcgaaaa atttaccatt attttttaat    3720
gcgcccggag agtctccaca agtgtgccca tatatctgcc attcaaattc taagctcacg    3780
agacaaaaga gttatcgatc gatatgcagg ctctgtgtgg cccctgttag ctttctgtta    3840
aatttaaatt tctgtaaagt gcccgccact gcggtcgctt tcacggatca gattagtcgt    3900
tgtctggata ttaacgagga aggtagtgat cgcgcattag tgtcatgcgt tatttgcttc    3960
ggcgctgaga agtgttttga aaacagtttt tgaaagcccg aggaagatct caatgggtca    4020
atgagtcatc tcattcacta tgcaaataag accggggttg cgccaaacct ttacttaaag    4080
acgatgactc gcggggaagt taagacgttt tattagttac tgcgaatgaa tcatgtgtaa    4140
tgcagatctg aaaccgcagt tgcaaagtga tctcgacatc aacccacaca acaaaaacat    4200
aagcagtgaa acaagttttt aaaacattta acgaagcaag gttaagaaac tgcagaaaac    4260
ggcgcccacg gcgcaatcga aaaaaatttt aaaaaaaagc tttgttttaa tgacgccaga    4320
acagctaata aattgattga attgcatttg acaaatgatt aatttgaaat ctacatatat    4380
gcgacctgtg acgtcatcga agtttttaaa aaaactattt taaaatgcct ggtgggcaga    4440
taatgaatat gccctaaaag gcaactcccg ccgtgtccac ttttctgtga agtgctcgga    4500
ttgtgatacc attcccaaat acgaattaaa cgtatagttt tattgctgac ccggcgagtt    4560
tagaaaatgt cgtgtaagac gagccgatag aggcccatgt ttacccaact cggaactggg    4620
ttggcgacag tttcccccaa gcacagacat ttgcatcgaa tttaggcgta cagggcttcc    4680
gttcccctcc agaagcgctt aatatgcgtt ttttattgcc aattacaatt aagtaatcca    4740
tcgattaggc gttatgcggc atgttaggac cctcctctgg agcccgcgct ccagcctact    4800
tacgactgca aaaccgtgc ggctgaattc attcgctcgc tgatttggct ccgcccatct     4860 aattttgta ttcgttttct actgttcgtg ggacacaggg gcgtgggcgc agagggcttt     4920
gagttgcttg gaccgattgg taggtggtga ttccttcggt tcaggaatcc gtccatctag    4980
cacacgaatt agctttcgtg tgtgtttctg agttgatctc acacatgtac tacgtacgtc    5040
```

-continued

```
cgagtgtgtt taattaaatt atttgaaatt actgaatcgt gcggagcgga gactctgtct    5100
ccccactccg gacacccctc ccaaatcttt tgttgtgcac acgatgtggg ccagtcaatt    5160
gtttatgaag tgcacagtgg gtatatagag cactgatctc catgtggcag gggtatccac    5220
tttcgtgttt tcgctattgc tcatgtgtct gtgggctgtt cgcttaaaca ttttttccga    5280
atacaactaa attctggcgc tgttgttttt tcgcggatgc ttcacaagct cacttcacca    5340
tgaagtcagc ccccatccac atctatatcc acatctgcag acccatctcc gcacgcatcc    5400
atcttaatta tgactttttt acgatgacaa tttcgggctg agctttgcaa agttgattac    5460
acaaaaaaaa acttcagttg tggactgttg tccccaatca cgatcgctgt ttttctgcca    5520
ctcctaagca ttttcaaaga atttgtgttt ctggctattt ccttgtttt tccagcctcc     5580
aattcaagtg taaacacagc cgaacgatcg tctgttattc attaagtgca gagagagcat    5640
taaatttagc gaacaaagtc tttcgttgcc aataaacgga ctttatggac aagtaaatta    5700
gtttattgta tttcaaaatc gcccactcca tgaaaatcta taaggtcact atatagccga    5760
aatgttggca ctccattcgt tctggcacgt acgtatacaa catgataaac aaggaacacg    5820
cgatttaat attcctcaga tatttgtttg aatccgaagc gactataatt atctgcgctg     5880
ttgcatatcc agctgtcggt gtcgcgaact cccttctttc cgacattttc cagactatcc    5940
ctccgatccc ctcttgttgg gtttaatttg gattaagtga caggcagaag agaaagcgag    6000
aaagaatgtt atcggcgagc cgaagtttat ctaccctctt gtgaaaatca gaatatattc    6060
tcgactaata tttgactggc atgtcaattg taagctgaag ctctgtaact tctctattct    6120
attgtgttgt attgagttat atattgagtt gtatgaaccc aatatggtat ttttcattta    6180
taccatttta acattttgc taagagctgt gcacttcttc cgttaaatgt tagtctttgc     6240
ttgcttgttg tttttcctgt gcaaacctga tcgacgggtt ttcttttggc agtctctaag    6300
tgcattccac atcccgggga catcggtccc ccggttcact cggctctttc tgaatggcgg    6360
ttctgctaag tttgattacg ccattctgtc aactgtcgcc taagactttg ggcctgagca    6420
gggcaaacaa taaagttgtt tgtcaattgg ttttacaaat agcctagtgg ccaaatacgc    6480
aacacaaaca gagggccaa acagtaagcc aattagagaa gatgattgtg cgattctgtt     6540
tatcttatca ggccgacctt cccacctggg gggggtcatt tacaaaaccc aattttttgc    6600
caagccaaaa aacttggact gattagccgt tttcaacgga tgggtcgggt atatgtttcc    6660
tgaataccaa ttcttcggct gttgataaat aatcagaagt ggcgtattca aattagccag    6720
gtcttgagtg tgattagcag atttctcaca catttcaagt atcacagcgg tcagtatcac    6780
tgtggaaacg agaatccccc agaagaagcc gccttgaaat ttacgaacaa agccgcctat    6840
aaatctcaca atttcggcgc ccccattgcc tgagtcgccc ccaggctcca ttcgagcccc    6900
atctagaaga gttatcaaag cgtaaagcgc aacaaattga ttgctaattg atactgatgt    6960
gtcgattatt ttatgattat tctttatgat cgttagacgt tgatacccgc accaaacctg    7020
attcaaattt agtggatcac tccgaccgcc gccactgctg gtactggggg ctccagtacc    7080
cacgtccacc gccgaccttg tcttgtcttc gcatggattg taataattta ataactacac    7140
ggaggagcaa attaagaccg aattcggtac cacagaaacc acttaagacg ctttctttaa    7200
ttgcccccaa aacggagatt tggctgtgaa gaaacctgta gggcagcttt tttctctcgc    7260
tccgttccag cctcatgtcc actccatgtg aaaaccatcg tagcatgaag cgatgtcaaa    7320
tgccgttttt cgagagcttc caattccaac ctattgtttt tgacttccaa ggccctaagg    7380
tctagtgggg tcacaaagtg gcctgagtga gcaatgcggg ttcttgcttc attttcagct    7440
```

```
tacgttactc attcgacgcg aattacctga agtccagccc acatagacat tgctcatccg    7500
atccgtggct gctctttctt tgcagaccaa accaatggac tttaacaact gcggcttcat    7560
tgatccgcag gcccagctag ctggagcttt ggccaagcag gacatccgac agttcgttgc    7620
tgccctggac agcggtgccc tggccgatct acaagacgac cgccatacca gtatctacga    7680
gaaggcactc tcaacaccag gttgtcgtga cttcattgaa gcctgcatcg accacggcag    7740
ccaggtgaac tacgtgagta gagcaacaag gagtagaggt cggacaccat ctaaccacag    7800
ttcatcttca cagatcaaca agaagctgga caaggccgca atcagctatg cggctgactc    7860
tagggatcca ggaaacctgg cggctctcct taagtaccgc cccggaaaca agtccaggt    7920 tgatagaaaa tatgggcagc ttactccact taactcactt gccaagaatc tcacggatga    7980
aaatgcccca gacgtgtact cctgcatgca actcttgctg gactacggcg cctcgccgaa    8040
tatcgtagac cagggcgagt tcacacccct tgcaccatgt gctgagaaga gcaaggtgaa    8100
ggctgggaag aaggaactga ttcagctctt tctggaccat ccggagctgg atatcgatag    8160
ttaccgaaac ggggaggtgc gcagactgct gcaggcgcaa tttccggagc ttaagctgcc    8220
ggaagagcgt cataccgggc cggagattga catccaaact cttcaaagga ctctacggga    8280
cggggacgaa acactgtttg agcagcagtt cgctgagtac ttgcagaatc tcaaaggcgg    8340
agcggataac caactaaatg cccaccagga ggaatacttc ggactgctgc aggagagcat    8400
caagaggggc aggcagcgag ccttcgatgt cattttgtcc actggcatgg atatcaactc    8460
gagaccaggc agggccaacg aggccaatct cgtagagacg gccgtgatat acggtaactg    8520
gcaggcgttg gagcgactgc ttaaggagcc aaacctgcga cttactccag actccaagct    8580
actaaatgca gtaatcggcc gtctggatga gccaccgtat gatggctcca gccaccagcg    8640
ctgctttgaa ttgctcatta acagcgatcg cgtagacatc aacgaagctg attccggacg    8700
cctggtgcct ctgttcttcg ctgttaagta ccgcaacacg agtgcgatgc aaaaactcct    8760
gaagaacggt gcctacattg gttctaagag cgcatttggc acactaccca tcaaggacat    8820
gccacccgag gttctcgaag agcacttcga ctcgtgtatc accacaaacg gagagaggcc    8880
tggtgaccag aactttgaga tcatcatcga ttataagaac ctaatgcgcc aggagagaga    8940
ctccggactc aaccagctgc aagacgaaat ggccccgatc gcattcatcg ccgagtcgaa    9000
ggagatgcgc cacctgctcc agcacccgct gatctcgagc tttctattcc tcaagtggca    9060
ccgactttcc gtgatattct acctgaactt cctgatatac tcgcttttta ccgcctccat    9120
aattacctac acgctcctca gttccacga aagcgatcaa agggctctta ctgcattttt    9180
cggattgctt tcctggctgg gaatcagcta ccttatatta cgggagtgca tccagtggat    9240
aatgtctcca gttcggtact tttggtctat aacgaatatt atggaggtgg ctcttattac    9300
actatctatc tttacctgca tggaatccag cttcgacaag gagacgcagc gcgtcttagc    9360
cgtatttacc atcctactcg tctccatgga gttttgttta ctagtgggct ccctgccagt    9420
gctctcaatt tcgacgcaca tgctgatgct gcgagaggtg tcaaacagct tcttaaagag    9480
ctttaccctc tactcgatct tcgtgctcac cttcagcctg tgtttctata tcctcttcgg    9540
caagtcagtg gaggaagacc agtctaaaag cgctacgcca gtccacctc tggggaagaa    9600 ggaggggaag gacgaggaac agggcttcaa cacatttacc aagcctatcg aggccgtgat    9660
caagaccatt gtgatgctga caggcgagtt tgacgccgga agcatccagt ttaccagcat    9720
ctacacctac ctgattttcc tgctcttcgt gatctttatg acgatagtgc tgttcaacct    9780
```

```
tttgaacggt cttgcagtga gcgacaccca agtaggtcta tcgccattcg tattatttcc   9840
cttcgctaat cccatttccg gcgttattca ttatctaggt tattaaggct caggcggaac   9900
tgaacggagc catttgcaga accaacgtcc ttagtcggta cgagcaggtt ctcactggcc   9960
acggacgcgc tgggtttttg ttgggcaacc atctcttccg cagcatctgc caacgtttga  10020
tgaacatcta cccgaactac ttaagtctgc gtcagatttc cgtgctgccg aacgatggaa  10080
acaaagtgct tattccaatg agcgatccct tcgaaatgag gacccttaag aaggctagct  10140
ttcagcaatt gccctgagt gctgcagtgc cccagaagaa gctgttggat ccaccgctta   10200
gacttctgcc ctgctgctgt tccctgctca ccggaaagtc ctcccagatg agcggccggg  10260
tggtcaaacg ggccctcgag gtaatcgatc agaagaacgc ggcggagcag aggcggaaac  10320
aggaacagat caacgacagt cgactgaagc tgatcgagta caagctggag caattaatac  10380
agctggtcca ggaccggaag tgatggagaa tgtattttgg tagctttagt atttatgaga  10440
ctaatcaacc ttttagaacg atttgcattt aacattcagt ttaaagagcc gagttagtcg  10500
gaaattgttt ttattaacat acgagtaatg aaattgaaca aaaccccttaa taattgtcag  10560 taagtaagta gtatataatg gttatataga cagtaaaatat tgtataaacg aatatcatta  10620
ctgtactatt tgtacccgag taaatattta atttcaaatg ttagatgtac gcttttaga   10680 gttttcattt agttattcgc tttacttaac catcttttat tttgatttga tatgattcgg  10740
ttcaaaatgt gtgttagtca catattatgg ttaatgagct cttaatcttt aacttttttg  10800
tcttccttgt ctgtaataat tcctttgttt aagccagagc tgaactgagc gtagcggacc  10860
aaatcgaatt acacgggcgt aaagagctaa cgaggcaatc aatggcaatg gaaaaccgac  10920
tggaaactta tgcaagctgt gcggtcataa tttgttaaca attttcagcc taattatttg  10980 tttttatga tttccgacag caaggagtaa aaagcttcag gccgttttat ggagtgagtg   11040
aagcgcatgc atcgattaag ctaagctaga atacaaatta ctactgggcc ttagtttggt  11100
tactcgactt gataacgctc ttgattagct gtggctgtta ttgttattgt tagaggacta  11160
ggactaggac ctttaaagcg gcaaatcaaa ataattgact tagttcttgg agcgttttgg  11220
acaattgtac gacttgttat tcggtttaag tggtgttatg cgacttattc tgcttctagt  11280
agcgtggccg atgaaacatt aactcctatc tttcgtatat actttaatct caacaatgta  11340
tatatataaa taaaatcgtg tattctgtaa ggcatgccta attaaaccag ccgtattgct  11400
aactataggt gtatatttgt gtacttcatg tggttttact tcctgcatcc tgcatccacc  11460
tatctctccc aagtccggga gattgtctta atgtcttgtc tgtgttgcgt gagctctaaa  11520
tgcataggat tcggttctgt cttcgcctcc aattcaggtt cgcttgcttc gtactgctat  11580
cgacttgact gacttgagtg ggaccaaagc ctcatctact gcgattacga ttatctaaga  11640
gttaagtttg tccttgtatt cccagattct gtgtgagtgg cctgcctgct gttattttga  11700
gtattggttt cggtaacgat gactcgaact tgcgtctcta taattgaata tgcatcattt  11760
tttttattgt cgttatactc tatgactaaa ttaaacatcc cacatcatag catcgctccg  11820
actggtctcg cctcgctctg taatctggtt aatcgatttc tgttgaagaa aactaaaata  11880
aaagcatttc tcttttttt tgagcttttta gttttttgt ggttggaatc aggttctatt   11940
gctatttcgt taccattatc ataatcgttt ttcgttatg tacaatcgaa tacgagtacg   12000
taccaatatt aaatatcact taattgacga gtgtttggtt tctgtctgtt tttggttttg  12060
tttccttgtt aacaattcta attaaaatta tgacccttatt ttttgtatt tctgtgtaaa  12120 aattgcagtt aaaatcacaa ttaagttgtt gtgtgttcat ttggttgttt gtttctggaa  12180
```

-continued

```
aaaacgtttt agttggtacc atagaatttc aacttactat caatcgctgt ctgattgtct    12240
gttgttaagt tatgaaagta gagttagagt agcaaagtgc cctgaatggc gcggggtgc    12300 ataagttatt cggatttgt taatattttc ccactcggag tgtacgttat tcacttctta    12360 actttttcc tgttcgatgt tttaacttaa tgcgatcaca atggagactt aaaagagaga    12420
acaacactta aaagtaaca aaacaaggcg agtttcttgg aaacttggcc cgtcctaacc    12480
attcttagtc gtacaataaa gtgagtgtaa attgtaaatt attttgctaa aatagagttc    12540
atgtggaagc ttgttggttg ttcattgtat aggagaccaa aattgttacg tcctgctttt    12600
gatttgctat tttcgactgt acttatcgaa aataaactta aaaacttcat cttcgtaaac    12660
ttcttctgac tggtacttat gtggactgct gattgattac ggattaattt gggtctcgat    12720
aagagtgcag tgtagtgtgt taatcccgac tgggattagg attgatataa atatgtaagt    12780
gcgttgagta caaaatcact tgacattgtt tttggcttag ttattaccaa agaccaatat    12840
aatctctaag atgcgtatcg gccatgcatt ggggatgcaa aaaaaaaaa aaaaaatggt    12900 atggcgctac gcatcttcgt attttaacgt ctttgttatt accgttggat gcacacgaga    12960
aagggagatg tggatgaggg aggagccata agatatgtac aatacaatat aataataatc    13020
aaatctacta atacttcgct tttgtacttc gaacaatcgg taatggataa tattcgctat    13080
cgtaatcgca tttgtaatcg gcaatctttg cgctatcgta acgaaaaacc tttataatta    13140
cttcaataaa ttgtatctaa ctaacgtcat agtctgtaac tatagtatta gctcattaat    13200
ttaaaatact tcctttggca tatgtacaaa atgtatttag atactattca catataccct    13260
ccgtatatgc aagtcgataa ttacgaaaca aacactacag ttatgagcct agatctaacc    13320
gcgatagtta gttacacatg taatgtatgc atgtgatgca aacctctacg tattgtatag    13380
ttcaaaaaca accttcgaaa atgtggcaga aagttggccc acggcaggag aatagaaggc    13440
cgtgccttgc cttcattgcc tcacttgtgg gtcaggcatt ct                       13482
```

<210> SEQ ID NO 9
<211> LENGTH: 759
<212> TYPE: DNA
<213> ORGANISM: Drosophila melanogaster

<400> SEQUENCE: 9

```
atgcagaatt ctccggctcc gtgtgcctgg tacttgccct ggtccctggc cgcccagcag     60
caccagcaaa agatgctgca aatgcagtcg ccgtttctgg acaagatggg cgccacatcg    120
gtgggcggca tcttcgctgg ccagccgcag atgcagcaac aattgtcgcc caatacggca    180
gcagcaccgc cggcaaacta tcagcagccc gctttgcatc caagcgccgc accaggcgca    240
ccacacttcc acatgggatc cccgtatagc catctggcac cgcagctcct caacgccgga    300
cagctgaacc agaacgcact gatgcactcc gccatgttct cttccctgcc acttggtgcg    360
tactatgcac ccgccgccgg cgcaggtcac tcggcctttg gtggcgttcc cctgaccacg    420
gctgcccagc aatctctatt ggccgccacc ggaggagcaa ctgctggcca tttggccaac    480
cagcagacga cggctcaagt gcccgtccag gtgcccgtgc aaatggccca acggacagct    540
ccggccgcct gctccatggt ccagccactt aactgcctgc cgcaccagga actgaatcac    600
ctgtcgtcca tcaatctcaa cctgctgcgc agtccggcgc ctccgctccc agccattcag    660
gtcttgccaa gtgccgaggt gccgattaat aagaaggtga gttgcagttt gcttagtact    720
tgtaatgata ggcactattc gtacttgagc gaaggctag                             759
```

<210> SEQ ID NO 10
<211> LENGTH: 252
<212> TYPE: PRT
<213> ORGANISM: Drosophila melanogaster

<400> SEQUENCE: 10

Met Gln Asn Ser Pro Ala Pro Cys Ala Trp Tyr Leu Pro Trp Ser Leu
1               5                   10                  15

Ala Ala Gln Gln His Gln Gln Lys Met Leu Gln Met Gln Ser Pro Phe
            20                  25                  30

Leu Asp Lys Met Gly Ala Thr Ser Val Gly Gly Ile Phe Ala Gly Gln
        35                  40                  45

Pro Gln Met Gln Gln Gln Leu Ser Pro Asn Thr Ala Ala Ala Pro Pro
    50                  55                  60

Ala Asn Tyr Gln Gln Pro Ala Leu His Pro Ser Ala Ala Pro Gly Ala
65                  70                  75                  80

Pro His Phe His Met Gly Ser Pro Tyr Ser His Leu Ala Pro Gln Leu
                85                  90                  95

Leu Asn Ala Gly Gln Leu Asn Gln Asn Ala Leu Met His Ser Ala Met
            100                 105                 110

Phe Ser Ser Leu Pro Leu Gly Ala Tyr Tyr Ala Pro Ala Ala Gly Ala
        115                 120                 125

Gly His Ser Ala Phe Gly Gly Val Pro Leu Thr Thr Ala Ala Gln Gln
    130                 135                 140

Ser Leu Leu Ala Ala Thr Gly Gly Ala Thr Ala Gly His Leu Ala Asn
145                 150                 155                 160

Gln Gln Thr Thr Ala Gln Val Pro Val Gln Val Pro Val Gln Met Ala
                165                 170                 175

Gln Arg Thr Ala Pro Ala Ala Cys Ser Met Val Gln Pro Leu Asn Cys
            180                 185                 190

Leu Pro His Gln Glu Leu Asn His Leu Ser Ser Ile Asn Leu Asn Leu
        195                 200                 205

Leu Arg Ser Pro Ala Pro Pro Leu Pro Ala Ile Gln Val Leu Pro Ser
    210                 215                 220

Ala Glu Val Pro Ile Asn Lys Lys Val Ser Cys Ser Leu Leu Ser Thr
225                 230                 235                 240

Cys Asn Asp Arg His Tyr Ser Tyr Leu Ser Glu Gly
                245                 250

<210> SEQ ID NO 11
<211> LENGTH: 547
<212> TYPE: DNA
<213> ORGANISM: Artificial sequence
<220> FEATURE:
<223> OTHER INFORMATION: Insertion site
<220> FEATURE:
<221> NAME/KEY: misc_feature
<222> LOCATION: (1)..(547)
<223> OTHER INFORMATION: n is any nucleotide

<400> SEQUENCE: 11
ggttaatcaa caatcatatc gctgtctcac tcagnctcaa tacgacactc agaatactat      60
tcctttcact cgcacttagt gcaagcatac gntaagtgga tgtctcttgc cgacgggacc    120
accttatgtt atttcatcat ggtttgcgcc aagttttctg atttcatncg gtgttttgga    180
ctcggcgaga ctggaagttg atgctgccgc gtgaatgcca tcgtcggtca ggtattaaaa    240
cgtgacnctt ctanttcgcg tgtgantccc ccgagtntgc agtcgatttg tgcncagaaa    300

-continued

```
acattcaaga tgccttgtnt actttgtgaa aagatctaat aacactatga aacttaaatc    360
aatgtgcaag tgacggttat ataaattaat tatnttaatt caaagcntaa ntaatgcgaa    420
gagcctgnaa ataaagtacn ctaaaantat tcccnggana cntaattttnt gtcgacataa    480 ctcgaacaac tnatagttga ataatcaccg gggcccgaca ttttggctgn agaatacnaa    540
ttttcct                                                               547
```

<210> SEQ ID NO 12
<211> LENGTH: 1119
<212> TYPE: PRT
<213> ORGANISM: Homo sapiens

<400> SEQUENCE: 12

| | | | | | | | | | | | | | | |
|---|---|---|---|---|---|---|---|---|---|---|---|---|---|---|
| Met | Lys | Cys | Ser | Leu | Arg | Lys | Met | Trp | Arg | Pro | Gly | Glu | Lys | Lys | Glu |
| 1 | | | | 5 | | | | | 10 | | | | | 15 | |
| Pro | Gln | Gly | Val | Val | Tyr | Glu | Asp | Val | Pro | Asp | Asp | Thr | Glu | Asp | Phe |
| | | | 20 | | | | 25 | | | | | 30 | | | |
| Lys | Glu | Ser | Leu | Lys | Val | Val | Phe | Glu | Gly | Ser | Ala | Tyr | Gly | Leu | Gln |
| | | | 35 | | | | 40 | | | | | 45 | | | |
| Asn | Phe | Asn | Lys | Gln | Lys | Lys | Leu | Lys | Thr | Cys | Asp | Asp | Met | Asp | Thr |
| | 50 | | | | | 55 | | | | | 60 | | | | |
| Phe | Phe | Leu | His | Tyr | Ala | Ala | Glu | Gly | Gln | Ile | Glu | Leu | Met | Glu |
| 65 | | | | 70 | | | | 75 | | | | | 80 | |
| Lys | Ile | Thr | Arg | Asp | Ser | Ser | Leu | Glu | Val | Leu | His | Glu | Met | Asp | Asp |
| | | | | 85 | | | | 90 | | | | | 95 | | |
| Tyr | Gly | Asn | Thr | Pro | Leu | His | Cys | Ala | Val | Glu | Lys | Asn | Gln | Ile | Glu |
| | | | 100 | | | | 105 | | | | | 110 | | | |
| Ser | Val | Lys | Phe | Leu | Leu | Ser | Arg | Gly | Ala | Asn | Pro | Asn | Leu | Arg | Asn |
| | | | 115 | | | | 120 | | | | | 125 | | | |
| Phe | Asn | Met | Met | Ala | Pro | Leu | His | Ile | Ala | Val | Gln | Gly | Met | Asn | Asn |
| | 130 | | | | | 135 | | | | | 140 | | | | |
| Glu | Val | Met | Lys | Val | Leu | Leu | Glu | His | Arg | Thr | Ile | Asp | Val | Asn | Leu |
| 145 | | | | | 150 | | | | | 155 | | | | | 160 |
| Glu | Gly | Glu | Asn | Gly | Asn | Thr | Ala | Val | Ile | Ile | Ala | Cys | Thr | Thr | Asn |
| | | | | 165 | | | | | 170 | | | | | 175 | |
| Asn | Ser | Glu | Ala | Leu | Gln | Ile | Leu | Leu | Asn | Lys | Gly | Ala | Lys | Pro | Cys |
| | | | 180 | | | | 185 | | | | | 190 | | | |
| Lys | Ser | Asn | Lys | Trp | Gly | Cys | Phe | Pro | Ile | His | Gln | Ala | Ala | Phe | Ser |
| | | | 195 | | | | 200 | | | | | 205 | | | |
| Gly | Ser | Lys | Glu | Cys | Met | Glu | Ile | Ile | Leu | Arg | Phe | Gly | Glu | Glu | His |
| | 210 | | | | | 215 | | | | | 220 | | | | |
| Gly | Tyr | Ser | Arg | Gln | Leu | His | Ile | Asn | Phe | Met | Asn | Asn | Gly | Lys | Ala |
| 225 | | | | | 230 | | | | | 235 | | | | | 240 |
| Thr | Pro | Leu | His | Leu | Ala | Val | Gln | Asn | Gly | Asp | Leu | Glu | Met | Ile | Lys |
| | | | | 245 | | | | | 250 | | | | | 255 | |
| Met | Cys | Leu | Asp | Asn | Gly | Ala | Gln | Ile | Asp | Pro | Val | Glu | Lys | Gly | Arg |
| | | | 260 | | | | 265 | | | | | 270 | | | |
| Cys | Thr | Ala | Ile | His | Phe | Ala | Ala | Thr | Gln | Gly | Ala | Thr | Glu | Ile | Val |
| | | | 275 | | | | 280 | | | | | 285 | | | |
| Lys | Leu | Met | Ile | Ser | Ser | Tyr | Ser | Gly | Ser | Val | Asp | Ile | Val | Asn | Thr |
| | 290 | | | | | 295 | | | | | 300 | | | | |
| Thr | Asp | Gly | Cys | His | Glu | Thr | Met | Leu | His | Arg | Ala | Ser | Leu | Phe | Asp |
| 305 | | | | | 310 | | | | | 315 | | | | | 320 |

```
His His Glu Leu Ala Asp Tyr Leu Ile Ser Val Gly Ala Asp Ile Asn
            325                 330                 335

Lys Ile Asp Ser Glu Gly Arg Ser Pro Leu Ile Leu Ala Thr Ala Ser
            340                 345                 350

Ala Ser Trp Asn Ile Val Asn Leu Leu Leu Ser Lys Gly Ala Gln Val
        355                 360                 365

Asp Ile Lys Asp Asn Phe Gly Arg Asn Phe Leu His Leu Thr Val Gln
    370                 375                 380

Gln Pro Tyr Gly Leu Lys Asn Leu Arg Pro Glu Phe Met Gln Met Gln
385                 390                 395                 400

Gln Ile Lys Glu Leu Val Met Asp Glu Asp Asn Asp Gly Cys Thr Pro
                405                 410                 415

Leu His Tyr Ala Cys Arg Gln Gly Gly Pro Gly Ser Val Asn Asn Leu
                420                 425                 430

Leu Gly Phe Asn Val Ser Ile His Ser Lys Ser Lys Asp Lys Lys Ser
            435                 440                 445

Pro Leu His Phe Ala Ala Ser Tyr Gly Arg Ile Asn Thr Cys Gln Arg
        450                 455                 460

Leu Leu Gln Asp Ile Ser Asp Thr Arg Leu Leu Asn Glu Gly Asp Leu
465                 470                 475                 480

His Gly Met Thr Pro Leu His Leu Ala Ala Lys Asn Gly His Asp Lys
                485                 490                 495

Val Val Gln Leu Leu Leu Lys Lys Gly Ala Leu Phe Leu Ser Asp His
            500                 505                 510

Asn Gly Trp Thr Ala Leu His His Ala Ser Met Gly Gly Tyr Thr Gln
        515                 520                 525

Thr Met Lys Val Ile Leu Asp Thr Asn Leu Lys Cys Thr Asp Arg Leu
    530                 535                 540

Asp Glu Asp Gly Asn Thr Ala Leu His Phe Ala Ala Arg Glu Gly His
545                 550                 555                 560

Ala Lys Ala Val Ala Leu Leu Leu Ser His Asn Ala Asp Ile Val Leu
                565                 570                 575

Asn Lys Gln Gln Ala Ser Phe Leu His Leu Ala Leu His Asn Lys Arg
            580                 585                 590

Lys Glu Val Val Leu Thr Ile Ile Arg Ser Lys Arg Trp Asp Glu Cys
        595                 600                 605

Leu Lys Ile Phe Ser His Asn Ser Pro Gly Asn Lys Cys Pro Ile Thr
    610                 615                 620

Glu Met Ile Glu Tyr Leu Pro Glu Cys Met Lys Val Leu Leu Asp Phe
625                 630                 635                 640

Cys Met Leu His Ser Thr Glu Asp Lys Ser Cys Arg Asp Tyr Tyr Ile
                645                 650                 655

Glu Tyr Asn Phe Lys Tyr Leu Gln Cys Pro Leu Glu Phe Thr Lys Lys
            660                 665                 670

Thr Pro Thr Gln Asp Val Ile Tyr Glu Pro Leu Thr Ala Leu Asn Ala
        675                 680                 685

Met Val Gln Asn Asn Arg Ile Glu Leu Leu Asn His Pro Val Cys Lys
    690                 695                 700

Glu Tyr Leu Leu Met Lys Trp Leu Ala Tyr Gly Phe Arg Ala His Met
705                 710                 715                 720

Met Asn Leu Gly Ser Tyr Cys Leu Gly Leu Ile Pro Met Thr Ile Leu
                725                 730                 735

Val Val Asn Ile Lys Pro Gly Met Ala Phe Asn Ser Thr Gly Ile Ile
```

```
                  740              745              750
Asn Glu Thr Ser Asp His Ser Glu Ile Leu Asp Thr Asn Ser Tyr
        755              760              765
Leu Ile Lys Thr Cys Met Ile Leu Val Phe Leu Ser Ser Ile Phe Gly
770              775              780
Tyr Cys Lys Glu Ala Gly Gln Ile Phe Gln Gln Lys Arg Asn Tyr Phe
785              790              795              800
Met Asp Ile Ser Asn Val Leu Glu Trp Ile Ile Tyr Thr Thr Gly Ile
                805              810              815
Ile Phe Val Leu Pro Leu Phe Val Glu Ile Pro Ala His Leu Gln Trp
            820              825              830
Gln Cys Gly Ala Ile Ala Val Tyr Phe Tyr Trp Met Asn Phe Leu Leu
            835              840              845
Tyr Leu Gln Arg Phe Glu Asn Cys Gly Ile Phe Ile Val Met Leu Glu
    850              855              860
Val Ile Leu Lys Thr Leu Arg Ser Thr Val Phe Ile Phe Leu
865              870              875              880
Leu Leu Ala Phe Gly Leu Ser Phe Tyr Ile Leu Asn Leu Gln Asp
            885              890              895
Pro Phe Ser Ser Pro Leu Leu Ser Ile Ile Gln Thr Phe Ser Met Met
                900              905              910
Leu Gly Asp Ile Asn Tyr Arg Glu Ser Phe Leu Glu Pro Tyr Leu Arg
            915              920              925
Asn Glu Leu Ala His Pro Val Leu Ser Phe Ala Gln Leu Val Ser Phe
    930              935              940
Thr Ile Phe Val Pro Ile Val Leu Met Asn Leu Leu Ile Gly Leu Ala
945              950              955              960
Val Gly Asp Ile Ala Glu Val Gln Lys His Ala Ser Leu Lys Arg Ile
            965              970              975
Ala Met Gln Val Glu Leu His Thr Ser Leu Glu Lys Lys Leu Pro Leu
                980              985              990
Trp Phe Leu Arg Lys Val Asp Gln  Lys Ser Thr Ile Val  Tyr Pro Asn
            995              1000              1005
Lys Pro  Arg Ser Gly Gly Met  Leu Phe His Ile Phe  Cys Phe Leu
    1010              1015              1020
Phe Cys  Thr Gly Glu Ile Arg  Gln Glu Ile Pro Asn  Ala Asp Lys
    1025              1030              1035
Ser Leu  Glu Met Glu Ile Leu  Lys Gln Lys Tyr Arg  Leu Lys Asp
    1040              1045              1050
Leu Thr  Phe Leu Leu Glu Lys  Gln His Glu Leu Ile  Lys Leu Ile
    1055              1060              1065
Ile Gln  Lys Met Glu Ile Ile  Ser Glu Thr Glu Asp  Asp Asp Ser
    1070              1075              1080
His Cys  Ser Phe Gln Asp Arg  Phe Lys Lys Glu Gln  Met Glu Gln
    1085              1090              1095
Arg Asn  Ser Arg Trp Asn Thr  Val Leu Arg Ala Val  Lys Ala Lys
    1100              1105              1110
Thr His  His Leu Glu Pro
    1115

<210> SEQ ID NO 13
<211> LENGTH: 839
<212> TYPE: PRT
<213> ORGANISM: Homo sapiens
```

<400> SEQUENCE: 13

| Met | Lys | Lys | Trp | Ser | Ser | Thr | Asp | Leu | Gly | Ala | Ala | Asp | Pro | Leu |
|---|---|---|---|---|---|---|---|---|---|---|---|---|---|---|
| 1 | | | | 5 | | | | | 10 | | | | | 15 |

Gln Lys Asp Thr Cys Pro Asp Pro Leu Asp Gly Asp Pro Asn Ser Arg
                20                  25                  30

Pro Pro Pro Ala Lys Pro Gln Leu Ser Thr Ala Lys Ser Arg Thr Arg
                35                  40                  45

Leu Phe Gly Lys Gly Asp Ser Glu Glu Ala Phe Pro Val Asp Cys Pro
    50                  55                  60

His Glu Glu Gly Glu Leu Asp Ser Cys Pro Thr Ile Thr Val Ser Pro
65                  70                  75                  80

Val Ile Thr Ile Gln Arg Pro Gly Asp Gly Ser Thr Gly Ala Arg Leu
                85                  90                  95

Leu Ser Gln Asp Ser Val Ala Ala Ser Thr Glu Lys Thr Leu Arg Leu
                100                 105                 110

Tyr Asp Arg Arg Ser Ile Phe Glu Ala Val Ala Gln Asn Asn Cys Gln
                115                 120                 125

Asp Leu Glu Ser Leu Leu Leu Phe Leu Gln Lys Ser Lys Lys His Leu
130                 135                 140

Thr Asp Asn Glu Phe Lys Asp Pro Glu Thr Gly Lys Thr Cys Leu Leu
145                 150                 155                 160

Lys Ala Met Leu Asn Leu His Asp Gly Gln Asn Thr Thr Ile Pro Leu
                165                 170                 175

Leu Leu Glu Ile Ala Arg Gln Thr Asp Ser Leu Lys Glu Leu Val Asn
                180                 185                 190

Ala Ser Tyr Thr Asp Ser Tyr Tyr Lys Gly Gln Thr Ala Leu His Ile
                195                 200                 205

Ala Ile Glu Arg Arg Asn Met Ala Leu Val Thr Leu Leu Val Glu Asn
210                 215                 220

Gly Ala Asp Val Gln Ala Ala His Gly Asp Phe Phe Lys Lys Thr
225                 230                 235                 240

Lys Gly Arg Pro Gly Phe Tyr Phe Gly Glu Leu Pro Leu Ser Leu Ala
                245                 250                 255

Ala Cys Thr Asn Gln Leu Gly Ile Val Lys Phe Leu Leu Gln Asn Ser
                260                 265                 270

Trp Gln Thr Ala Asp Ile Ser Ala Arg Asp Ser Val Gly Asn Thr Val
            275                 280                 285

Leu His Ala Leu Val Glu Val Ala Asp Asn Thr Ala Asp Asn Thr Lys
    290                 295                 300

Phe Val Thr Ser Met Tyr Asn Glu Ile Leu Ile Leu Gly Ala Lys Leu
305                 310                 315                 320

His Pro Thr Leu Lys Leu Glu Glu Leu Thr Asn Lys Lys Gly Met Thr
                325                 330                 335

Pro Leu Ala Leu Ala Ala Gly Thr Gly Lys Ile Gly Val Leu Ala Tyr
                340                 345                 350

Ile Leu Gln Arg Glu Ile Gln Glu Pro Glu Cys Arg His Leu Ser Arg
                355                 360                 365

Lys Phe Thr Glu Trp Ala Tyr Gly Pro Val His Ser Ser Leu Tyr Asp
    370                 375                 380

Leu Ser Cys Ile Asp Thr Cys Glu Lys Asn Ser Val Leu Glu Val Ile
385                 390                 395                 400

Ala Tyr Ser Ser Ser Glu Thr Pro Asn Arg His Asp Met Leu Leu Val

-continued

```
                405                 410                 415
Glu Pro Leu Asn Arg Leu Leu Gln Asp Lys Trp Asp Arg Phe Val Lys
            420                 425                 430
Arg Ile Phe Tyr Phe Asn Phe Leu Val Tyr Cys Leu Tyr Met Ile Ile
            435                 440                 445
Phe Thr Met Ala Ala Tyr Tyr Arg Pro Val Asp Gly Leu Pro Pro Phe
            450                 455                 460
Lys Met Glu Lys Ile Gly Asp Tyr Phe Arg Val Thr Gly Glu Ile Leu
465                 470                 475                 480
Ser Val Leu Gly Gly Val Tyr Phe Phe Arg Gly Ile Gln Tyr Phe
                485                 490                 495
Leu Gln Arg Arg Pro Ser Met Lys Thr Leu Phe Val Asp Ser Tyr Ser
            500                 505                 510
Glu Met Leu Phe Phe Leu Gln Ser Leu Phe Met Leu Ala Thr Val Val
            515                 520                 525
Leu Tyr Phe Ser His Leu Lys Glu Tyr Val Ala Ser Met Val Phe Ser
            530                 535                 540
Leu Ala Leu Gly Trp Thr Asn Met Leu Tyr Tyr Thr Arg Gly Phe Gln
545                 550                 555                 560
Gln Met Gly Ile Tyr Ala Val Met Ile Glu Lys Met Ile Leu Arg Asp
                565                 570                 575
Leu Cys Arg Phe Met Phe Val Tyr Ile Val Phe Leu Phe Gly Phe Ser
            580                 585                 590
Thr Ala Val Val Thr Leu Ile Glu Asp Gly Lys Asn Asp Ser Leu Pro
            595                 600                 605
Ser Glu Ser Thr Ser His Arg Trp Arg Gly Pro Ala Cys Arg Pro Pro
            610                 615                 620
Asp Ser Ser Tyr Asn Ser Leu Tyr Ser Thr Cys Leu Glu Leu Phe Lys
625                 630                 635                 640
Phe Thr Ile Gly Met Gly Asp Leu Glu Phe Thr Glu Asn Tyr Asp Phe
                645                 650                 655
Lys Ala Val Phe Ile Ile Leu Leu Leu Ala Tyr Val Ile Leu Thr Tyr
            660                 665                 670
Ile Leu Leu Leu Asn Met Leu Ile Ala Leu Met Gly Glu Thr Val Asn
            675                 680                 685
Lys Ile Ala Gln Glu Ser Lys Asn Ile Trp Lys Leu Gln Arg Ala Ile
            690                 695                 700
Thr Ile Leu Asp Thr Glu Lys Ser Phe Leu Lys Cys Met Arg Lys Ala
705                 710                 715                 720
Phe Arg Ser Gly Lys Leu Leu Gln Val Gly Tyr Thr Pro Asp Gly Lys
                725                 730                 735
Asp Asp Tyr Arg Trp Cys Phe Arg Val Asp Glu Val Asn Trp Thr Thr
            740                 745                 750
Trp Asn Thr Asn Val Gly Ile Ile Asn Glu Asp Pro Gly Asn Cys Glu
            755                 760                 765
Gly Val Lys Arg Thr Leu Ser Phe Ser Leu Arg Ser Ser Arg Val Ser
            770                 775                 780
Gly Arg His Trp Lys Asn Phe Ala Leu Val Pro Leu Leu Arg Glu Ala
785                 790                 795                 800
```

-continued

```
Ser Ala Arg Asp Arg Gln Ser Ala Gln Pro Glu Glu Val Tyr Leu Arg
                805                 810                 815

Gln Phe Ser Gly Ser Leu Lys Pro Glu Asp Ala Glu Val Phe Lys Ser
                820                 825                 830

Pro Ala Ala Ser Gly Glu Lys
            835
```